US011633554B1

(12) United States Patent
Puviani et al.

(10) Patent No.: US 11,633,554 B1
(45) Date of Patent: Apr. 25, 2023

(54) ADAPTIVE SYSTEMS AND METHODS FOR DELIVERY OF A MEDICAMENT

(71) Applicants: Luca Puviani, Rubiera (IT); Sidita Rama, Rubiera (IT)

(72) Inventors: Luca Puviani, Rubiera (IT); Sidita Rama, Rubiera (IT)

(*) Notice: Subject to any disclaimer, the term of this patent is extended or adjusted under 35 U.S.C. 154(b) by 422 days.

(21) Appl. No.: 16/892,312

(22) Filed: Jun. 4, 2020

Related U.S. Application Data

(60) Provisional application No. 62/859,759, filed on Jun. 11, 2019.

(51) Int. Cl.
*A61M 15/00* (2006.01)
*A24F 40/51* (2020.01)
(Continued)

(52) U.S. Cl.
CPC ......... *A61M 15/0065* (2013.01); *A24F 40/10* (2020.01); *A24F 40/51* (2020.01);
(Continued)

(58) Field of Classification Search
CPC .............. A61M 15/0065; A61M 15/06; A61M 2205/33; A61M 2205/3334; A61M 2205/3368; A61M 2205/3653; A61M 2205/52; A61M 2205/8206; G16H 20/13; A24F 40/10; A24F 40/51; A24F 47/00; A61K 31/137; A61K 31/138; A61K 31/192; A61K 31/357; A61K 31/404; A61K 31/4045; A61K 31/439; A61K 31/44; A61K 31/4402; A61K 31/4439; A61K 31/47; A61K 31/495; A61K 31/522; A61K 31/56; A61K 31/58; A61K 36/185

See application file for complete search history.

(56) References Cited

U.S. PATENT DOCUMENTS

| 5,605,930 A | * | 2/1997 | Samid .................... A61P 13/08 514/513 |
| 2012/0006342 A1 | | 1/2012 | Rose et al. |

(Continued)

OTHER PUBLICATIONS

Luca Puviani, Placebo Response is Driven by UCS Revaluation: Evidence, Neurophysiological Consequences and a Quantitative Model, Scientific Reports, Jul. 2016, No. 28991.

(Continued)

*Primary Examiner* — Steven O Douglas

(57) ABSTRACT

Methods and apparatuses for the therapeutic delivery of nicotine for smoking cessation, harm reduction and/or substitution. Furthermore, the devices and methods herein are useful as an alternative, general nicotine delivery system in place of tobacco combustion or high temperature (over 150 degrees C.) products. In addition, the methods and devices herein are useful for the therapeutic delivery of a drug, for reducing the cumulative drug dose and hence its potential toxic side effects, while increasing its neurophysiological and/or physiological effects. Moreover, the devices and methods herein are useful for addiction treatment or reduction. In certain embodiments, the methods are adaptable to a medicament delivery device that determines a sequence of drug doses to be delivered. Dose information may be used to control operation of the device.

20 Claims, 11 Drawing Sheets

(51) Int. Cl.
| | |
|---|---|
| A24F 47/00 | (2020.01) |
| A61M 15/06 | (2006.01) |
| A61K 36/185 | (2006.01) |
| A61K 31/495 | (2006.01) |
| A61K 31/192 | (2006.01) |
| A61K 31/4439 | (2006.01) |
| A61K 31/4402 | (2006.01) |
| A61K 31/138 | (2006.01) |
| A61K 31/4045 | (2006.01) |
| A61K 31/137 | (2006.01) |
| A61K 31/44 | (2006.01) |
| A61K 31/439 | (2006.01) |
| A61K 31/56 | (2006.01) |
| A61K 31/357 | (2006.01) |
| A61K 31/58 | (2006.01) |
| A61K 31/47 | (2006.01) |
| A61K 31/404 | (2006.01) |
| A61K 31/522 | (2006.01) |
| A24F 40/10 | (2020.01) |
| G16H 20/13 | (2018.01) |

(52) U.S. Cl.
CPC ............ *A24F 47/00* (2013.01); *A61K 31/137* (2013.01); *A61K 31/138* (2013.01); *A61K 31/192* (2013.01); *A61K 31/357* (2013.01); *A61K 31/404* (2013.01); *A61K 31/4045* (2013.01); *A61K 31/439* (2013.01); *A61K 31/44* (2013.01); *A61K 31/4402* (2013.01); *A61K 31/4439* (2013.01); *A61K 31/47* (2013.01); *A61K 31/495* (2013.01); *A61K 31/522* (2013.01); *A61K 31/56* (2013.01); *A61K 31/58* (2013.01); *A61K 36/185* (2013.01); *A61M 15/06* (2013.01); *G16H 20/13* (2018.01); *A61M 2205/33* (2013.01); *A61M 2205/3334* (2013.01); *A61M 2205/3368* (2013.01); *A61M 2205/3653* (2013.01); *A61M 2205/52* (2013.01); *A61M 2205/8206* (2013.01)

(56) References Cited

U.S. PATENT DOCUMENTS

| | | | |
|---|---|---|---|
| 2012/0077808 A1* | 3/2012 | Bachovchin | A61K 31/397 544/82 |
| 2013/0340750 A1 | 12/2013 | Thorens et al. | |
| 2016/0157524 A1 | 6/2016 | Bowen | |
| 2017/0143712 A1* | 5/2017 | Lannutti | A61K 9/5084 |

OTHER PUBLICATIONS

Siu Tsinau Yeung, Partial reinforcement, extinction, and placebo analgesia, Pain, Jun. 2014, pp. 1110-1117, vol. 155.
Robert Ader, Conditioned Pharmacotherapeutic Effects: A Preliminary Study, Psychosomatic Medicine, Feb.-Mar. 2010, p. 192-197,vol. 72, Issue 2.
Laura Luckemanna, Applications and limitations of behaviorally conditioned immunopharmacological responses, Neurobiology of Learning and Memory, Jul. 2017, p. 91-98, vol. 142.
Luca Puviani, Understanding and exploiting prediction errors minimization within the brain in pharmacological treatments. Behavioural Brain Research, Feb. 2019, p. 223-233.

* cited by examiner

ADAPTIVE SYSTEMS AND METHODS FOR DELIVERY OF A MEDICAMENT

CROSS-REFERENCE TO RELATED APPLICATIONS

This application claims the benefit of provisional patent application Ser. No. 62/859,759, filed 2019 Jun. 11 by the present inventors, which is incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FEDERALLY SPONSORED RESEARCH

None.

SEQUENCE LISTING

None.

BACKGROUND

Nowadays, electronic medicament delivery devices are widely adopted for their practical and safe utilization, for calibrated dose delivery, and for improving the medicament delivery for patients. For example, patient-controlled analgesia (PCA) devices and methods, such as, for instance, patient-controlled epidural analgesia (PCEA) devices, allow users to self-administer pre-computed and programmed doses of drugs (e.g., opioids, analgesic drugs, etc.) safely and effectively.

Other examples of electronic medicament delivery devices are pulmonary drug delivery systems: they have been used for long time to deliver medicaments for the treatment of respiratory disorders. The principle behind pulmonary drug delivery is aerosolization of drug compounds to be delivered to bronchioles and alveoli. Despite facing challenges like particle size optimization and degradation, a number of companies have developed technologies to deliver treatments for diabetes, migraine, osteoporosis, asthma, cancer and others.

Many preclinical and clinical studies have demonstrated that pulmonary delivery of medicaments is an efficient method for the treatment of both respiratory and systemic diseases. The many advantages of pulmonary delivery are well recognized and include rapid onset, patient self-administration, reduced side-effects, ease of delivery by inhalation, and the elimination of needles.

Nowadays, vaporizing devices, including electronic vaporizer devices or e-vaporizer devices, allow the delivery of vapor containing one or more active ingredient by inhalation of the vapor. Electronic vaporizer devices are adopted both for prescriptive medical use, in delivering medicaments, and for consumption of tobacco and other plant-based smokeable materials. Nevertheless, administered and/or self-administered drugs often present toxic side effects which increase with the cumulative administered dose. In the scientific literature, more specifically in the field of behavioral sciences, it has been shown that partial reinforcement administration protocols can increase drugs therapeutic effects while keeping low the toxic side effects.

On the basis of such administration protocols, in some administration trials a full dose of active drug is administered, while in the majority (or at least in the half) of trials, a placebo is administered (for instance, only 25% of the trials are reinforced with a full dose of active drug, while in the remaining 75% of the trials an inactive placebo is administered, typically in pseudo-random order). In general, the following procedure is adopted: first, associative learning is used to establish pharmacotherapeutic conditioning in the baseline period where each trial is reinforced; after such an initial learning phase, a partial schedule is provided with full active dose versus placebo or low dosages altering from trial to trial. Nevertheless, such described protocols present different drawbacks: a) for some diseases it can be dangerous to administer (almost) completely empty doses in the majority of the trials (i.e., to administer a pure placebo in the majority of the trials) and relatively high doses in few trials; b) it is not clear which rules or algorithms have to be adopted in the computation of the doses and about their relative frequencies, so that attempts and experiments have to be made in order to know if a specific administration schedule can be effective for the treatment of the given specific disease; c) a schedule consisting of some trials at a full dose administration versus some trials with placebo administration can determine a low patient experience about the treatment; d) the disclosed schedules or administration methods in the prior art can be improved and generalized for a broad spectrum of treatments.

What is needed, is a method and apparatus (e.g., system and/or device) for enhancing the positive/therapeutic or the desired drug effects while reducing the cumulative drug dose, and hence, the related toxic side effects. Further, it would be helpful to provide such methods and apparatuses applicable for a broad range of diseases and treatments. In particular, it would be helpful to provide methods and apparatuses for deliver varying doses of active drug (including active ingredients, even vapor or substances to be inhaled) in successive administration/inhalation trials, such that, the desired drug effects are enhanced while the cumulative drug dose is decreased or kept constant or even decreased.

For example, medicament delivery devices and vaporizer electronic devices may take advantage of the features listed above. In fact, it is well known that nicotine self-administration by conventional cigarettes is harmful and causes chronic diseases and cancer. For this reason, some companies have developed a range of products that have the potential to present less risk of harm to individuals than continued smoking conventional cigarettes (CCs) and reduce population harm compared to CCs. Some of the abovementioned products are represented by electronic vaporizer devices, e-cigarettes and, in general, by electronic devices which produce vapor or aerosol to be delivered to the user by heating liquid or solid material (or powder or loose-leaf material) containing nicotine. Such electronic devices can deliver nicotine with pharmacokinetic profiles which are similar to those obtained with CCs. This suggests that such devices can satisfy smokers and be a viable alternative to cigarettes for adult smokers who want to continue using tobacco. Nevertheless, only a small fraction of cigarettes smokers effectively switch from CCs to vaporizing devices; this is due to the fact that some aspects of smoking CC cannot be effectively reproduced by electronic vaporizers. For instance, specific features related to smoking CC, such as rituals, flavors, chemosensory characteristics, and others, represent rewarding and appetitive cues per se for heavy smokers, and they cannot be reproduced by electronic vaporizers and e-cigarettes. For this reason, some companies have developed specific electronic devices known as Tobacco Heating System (THS), which are designed to reduce the production of harmful and potentially harmful constituents (HPHCs) in comparison to a conventional cigarette where tobacco is burned. In THS a tobacco product is heated, but is not burned, so that an aerosol which contains nicotine but reduced levels of HPHC is produced and inhaled by the user. Despite the fact that such THS devices reproduce some aspects of the CC smoking, such as tobacco flavors, rituals, and some of the chemosensory cues, only a small fraction of CC smokers are able to switch from CC to THS. In fact, burned tobacco in CC releases more than 5000 chemical compounds other than nicotine, and such substances contribute to determine specific chemosensory characteristics and cues which have been strongly reinforced over time in heavy CC smokers. Such chemosensory cues represent rewarding cues for heavy smokers, so that they make CCs more rewarding and appetitive with respect to THS devices. Furthermore, recent research papers have raised concerns about the fact that burned tobacco can be harmful at the same level of CCs. Hence, what is needed is a method and/or apparatus (e.g., system and/or device) for enhancing the product acceptance (subjective reinforcing effects and sensorial experience, including satisfaction and pleasantness) and for improving user experience, while decreasing the cumulative substance(s) administration. In particular, it would be helpful to provide methods and apparatuses for enhancing the neuropsychophysiological and/or the physiological rewarding effects of using electronic vaporizers or THS devices, and/or of their associated cues (e.g., effects on the central nervous system, rewarding effects, flavors, perception of chemosensory features, etc.). Further, it would be helpful to provide such methods and apparatuses to decrease (or keep at the same level) the cumulative drug or substances/compounds (e.g., nicotine) delivered dose. Further, it would be helpful to provide such methods and apparatuses to deliver predetermined or pre-computed varying doses, and/or real-time or quasi-real-time computed varying doses of vapor or material (including active ingredients), over successive puffs/trials. Further, as far as THS and some vaporizer devices are concerned, in which the delivered or inhaled dose (also) depends on the user behavior (e.g., it depends on the puffing topography features), it may also be helpful to provide a method and apparatus for predicting the actual and/or the next user puff characteristics or inhalation characteristics and features (e.g., puff duration) since, without such a knowledge it would be more difficult (or even impossible in certain devices) to deliver a given computed dose of material (including active ingredients); moreover, such a knowledge or prediction, may help in counteracting users compensation (i.e., changing their puffing behavior to compensate for lower nicotine levels and/or lower chemosensory characteristics in mainstream smoke, such as making increased and more intense puffing) which is generally observed in users that are switching from CCs to electronic vaporizers or THS devices. Further, it would be helpful to provide and electronic record of the delivered doses, and of the related puffing features.

The methods disclosed herein are adaptable to the delivery of nicotine for therapeutic effect in various diseases, in particular nicotine for tobacco product use cessation, substitution and/or harm reduction. Because the requirements for a cigarette substitute are particularly difficult to satisfy, the present invention is herein described primarily with reference to nicotine delivery, but it will be understood that the invention is more generally applicable and addresses the general need for methods and apparatuses (e.g., systems and/or devices) for enhancing the desired physiological effects of a given active drug (e.g., immunosuppression, analgesia, rewarding effects, pleasantness, etc.), while decreasing (or maintaining the same) the cumulative drug dose or adjusting it as desired, over time. In particular, the present invention may be applicable for electronic medicament delivery devices and systems.

INCORPORATION BY REFERENCE

All publications and patent applications mentioned in this specification are herein incorporated by reference in their entirety to the same extent as if each individual publication or patent application was specifically and individually indicated to be incorporated by reference.

SUMMARY OF THE DISCLOSURE

Described herein are electronic delivery devices which deliver substances (for example electronic medicament delivery devices), or systems and methods of operating them. In particular, described herein, are methods for computing, controlling and delivering varying doses of substance (including active ingredients and drugs) over successive administration trials, in a pre-determined order or in a random order or in a pseudo-random order.

In certain embodiments, described herein are vaporization devices and methods of operating them. In particular, described herein, are methods for computing, controlling and delivering computed doses, in a predetermined order or in random order, or in pseudo-random order, of vapor and/or material (including active ingredients) in the vapor that can be delivered to a user.

More specifically, in certain embodiments, described herein are electronic vaporizers and methods of using them that determine and deliver a succession of doses/amounts of vapor and/or material in the vapor, based primarily, or exclusively, on the previous delivered dose(s)/amount(s) of inhaled vapor or material (including active ingredients) and based on the desired average cumulative delivered dose (i.e., the cumulative dose delivered, or to be delivered, in sequential puffs/trials divided by the considered number of puffs/trials), also based on the constraint that each dose can take only values within a given settable range (e.g., a range delimited by a maximum and a minimum value) and/or based on the constraint that each dose difference can assume only values within predetermined ranges, wherein a dose difference represents the difference between the dose delivered in a given trial and the dose delivered in the trial immediately before, or the difference between the dose delivered in a given trial and a liner combination of the doses delivered sequentially in some of the trials immediately before.

In particular, in some embodiments, described herein are methods and devices that compute and deliver successive and sequential varying doses/amounts of vapor or material, for each of the sequential puffs/trials or administration trials, in deterministic or random or pseudo-random order, such that, starting from a given or predetermined trial, the average positive dose difference is greater in magnitude than the average negative dose difference, subject to the constraint that the average cumulative administered or inhaled dose (i.e., the sum of the doses delivered over successive puffs/ trials divided by the number of trials) is kept constant over time (or over successive puffs/trials) or it is reduced (or it is varied and set as desired), and subject to the constraint that each dose can take only values within a given/settable (or predetermined) range, and/or subject to the constraint that a dose difference can assume values within predetermined ranges, wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

In certain embodiments, described herein are electronic vaporizers and methods of using them that compute, deliver, control, and determine a succession of doses/amounts of vapor and/or material in the vapor based primarily or exclusively on: a) the previous delivered dose(s)/amount(s) of inhaled vapor or material (including active ingredients); b) the predetermined (or desired) average or cumulative dose to deliver; the constraint that each dose can take only values within a given range and/or the constraint that each dose difference can take only values within predetermined ranges; c) the predicted puff duration of the actual puff, and the puff flow rate (or a related quantity such as the puff pressure or the puff volume); d) the temperature of the material as it is vaporized. In some variations the temperature of the material as it is vaporized may be estimated based on the electrical properties, e.g., the temperature coefficient of resistance or TCR, of the vaporizing element. In particular, in some embodiments, described herein are methods and devices that compute and deliver successive varying doses/amounts of vapor or material, in deterministic or random or in pseudo-random order, such that, starting from a given or predetermined puff/trial, the average positive dose difference is greater in magnitude than the average negative dose difference, wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

In certain embodiments, the computation, the delivery and the control of a succession of doses/amounts of vapor and/or material in the vapor is based primarily or exclusively on: a) the previous delivered dose(s)/amount(s) of inhaled vapor or material (including active ingredients); b) the desired or predetermined average or cumulative dose to deliver; the constraint that each dose can take only values within a given (or predetermined) range and/or the constraint that each dose difference can take only values within predetermined ranges; c) the predicted puff duration of the actual puff, and the puff flow rate (or a related quantity such as the puff pressure or the puff volume); d) the temperature of the material as it is vaporized, or an its estimation based on the electrical properties, e.g., the temperature coefficient of resistance or TCR, of the vaporizing element.

Although many of the examples described herein are directed to compute and determining dosage of nicotine or other tobacco-related materials, it should be understood that these methods and apparatuses may be used for dosage computation, determination and delivery of any vaporizable material, including therapeutic drugs, for enhancing their primary and desired (e.g., therapeutic, physiological) effects. Examples of active ingredients that may be used as described herein are provided below, and may include botanicals, nutraceuticals, pharmaceuticals, and the like, including combinations of these. The methods and apparatuses described herein may provide relatively pure material directly to the lungs, which may speed the action in the body, including both the time of onset and the off-time.

In some embodiments, disclosed herein are methods and devices that allow an improved ability to substitute for the nicotine delivery subjects experience while smoking cigarettes and similar tobacco combustion products. With improved nicotine delivery profiles, subjects applying the methods described herein will be provided with superior nicotine replacement therapy during attempts at smoking cessation, harm reduction and/or substitution. The methods of this disclosure can be implemented using any electronic vaporizer device or vaporizing device configured as specified herein.

For example, the present disclosure provides a method for delivering successive doses (e.g., material, vapor, active ingredients) in computed (e.g., in real time, or pre-computed) amounts and orders, for increasing the neurophysiological and/or physiological drug effects while reducing or setting as desired the average delivered dose, through dose computation, dose control, dose delivery and calibration of electronic vaporizer devices. These methods and apparatuses may include a) a dose computation system, which may compute the actual and the successive dose(s) to be delivered based on the previous delivered dose(s) and a set of constraints (e.g., constraints related to the average cumulative dose to deliver, the values that each dose can take, and/or the values that each dose difference can take, etc.); b) a puff duration predictor system which may construct a relationship of the actual (or next) puff duration as a function of previous puff topography features and/or patterns (e.g., the puff durations, average flow rates, average pressure drops, puff volumes, etc. of few of the previous puffs), the related previous delivered doses and, optionally, the actual dose to be delivered; c) a dose delivery system comprising setting-up: 1) a relationship of total particulate matter (TPM) or active ingredient vaporization or release as a function of temperature, time, power consumption of the vaporizing element(s) and the puff flow rate (which may be determined by a puff sensor or by a flow sensor); 2) a relationship of the power to be delivered to the vaporizing element (e.g., coil) as a function of the temperature (which may be determined by electrical resistivity or otherwise measured by a temperature-proportionate property), time, puff flow rate (which may be determined by a puff sensor or by a suitable sensor), the partial dose (e.g., material) which has to be delivered. In some embodiments, the present disclosure provides a method of metered dose control, dose computation, dose delivery and calibration of electronic vaporizer devices comprising measuring the amount of material vaporized from a vaporizable material from an electronic vaporizer device or vaporizing device relative to power, temperature and flow rate; particularly, a method comprising a) a dose computation system, which may compute the actual and the successive dose(s) to be delivered based on the previous delivered dose(s) and a set of constraints (e.g., constraints related to the average cumulative dose to deliver, the range of values that each dose can take, the range of values that each dose difference can take, etc.); b) a puff duration predictor system which may predict the actual (or next) puff duration as a function of previous puff topography features and/or patterns (e.g., the puff durations, average flow rates, average pressure drops, puff volumes, etc. of few of the previous puffs), the related previous delivered doses and, optionally, the actual dose to be delivered; c) a dose delivery system comprising setting-up: 1) a relationship of total particulate matter (TPM) or active ingredient vaporization or release as a function of temperature (which may be determined by electrical resistivity or otherwise measured by a temperature-proportionate property), time (which may be associated with detection of puffing/inhalation by the user), power consumption of the vaporizing element(s) and the puff flow rate (which may be determined by a puff sensor or by a flow sensor); 2) a relationship of the power to be delivered to the vaporizing element (e.g., coil) as a function of the temperature (which may be determined by electrical resistivity or otherwise measured by a temperature-proportionate property), time, puff flow rate (which may be determined by a puff sensor or by a suitable sensor), the partial dose (e.g., material) which has to be delivered.

Thus, described herein are methods of computing and delivering successive varying doses of a vaporizable material to a user of a vaporizing device over a time period (e.g., a single puff) and/or over a "stage", wherein a stage involves a predetermined number of puffs, which may be set in the factory. The time period typically comprises a plurality of sequential time intervals. In any of these methods and apparatuses the vaporizing device may include a heater controller, a heater, a dose computation unit, a puff duration predictor unit, a dose delivery unit, a source of the vaporizable material, a puff sensor detecting a user puff and measuring the puff flow rate and eventually measuring some puffing features (e.g., the puff duration, the pressure drop, etc.; a puff sensor may be any sensor which can detect airflow indicative of a user taking a puff. The sensor may be an electro-mechanical device; alternatively, the sensor may be any of a mechanical device, an optical device, an opto-mechanical device, a micro electro mechanical systems (MEMS) based sensor and an acoustic sensor), a puff duration predictor unit, a dose computation unit and a dose delivery unit. For example, a method may include: a) computing or estimating the puff duration of the given (e.g., the next or the incoming) puff/trial, from the puff duration and other puffing features related to some puffs/trials occurred immediately before, wherein the puff features (or puffing features) are computed in the puff duration predictor unit from the data received from the puff sensor; b) predicting for a given puff or inhalation trial (e.g., the actual or the next/incoming puff) the puff duration, wherein the puff duration is computed/predicted from the previous puff topography features (e.g., from the puffing features at the previous puff(s)/trial(s)) and the related delivered doses; wherein such prediction is performed in the puff duration predictor unit; c) calculating a dose/amount of material/vapor (e.g., active ingredients or TPM) to be delivered in a given puff/trial, wherein the doses to be delivered in successive puffs/trials are computed on the basis of the previous delivered dose(s), in the dose computation unit, and on the basis of some constraints (which will be described in a greater detail below); d) delivering a computed dose in a given puff/trial or time period, by the delivery of the sequence of the partial doses that form the dose to be delivered in that puff/trial or time period, during each time interval of the puff/trial or time period; wherein the partial dose is calculated in the dose delivery unit from the dose value computed by the dose computation unit and from the predicted puff duration transmitted from the puff duration predictor unit; wherein the partial dose is delivered by applying the power computed in the dose delivery unit, to the heater by the heater controller to vaporize the vaporizable material during a partial dose time interval; wherein the power to be delivered by the heater controller to the heater to vaporize the vaporizable material during a partial dose time interval is calculated in the dose delivery unit from a temperature of the vaporizable material being vaporized before the partial dose time interval, a flow rate before the partial dose time interval and the computed partial dose to be delivered in the time interval; e) storing or computing, for each of the sequential time intervals, a partial dose, wherein the partial dose is stored in the dose delivery unit; and summing the stored (or estimated) partial doses in the dose delivery unit to determine a total dose of vapor delivered during the time period (e.g., the puff) and transmitting such a computed dose to the dose computation unit.

Any of the calculation, prediction, or summing steps may be performed in the device (e.g., locally, e.g., within a controller which may include or be part of: the puff duration predictor unit, the dose computation unit, the dose delivery unit that are within the same housing as other portions of the device such as the heater control), and/or they may be performed remotely, e.g., in a processor that receives, such as wirelessly, the temperature(s), and/or partial dose information, and/or the puff flow rate(s), and/or other puffing features, and, optionally, other information (e.g., the power). Each of the following units may be located remotely from other portions of the device, including in a remote server (e.g., cloud-based server, smartphone or wearable apparatus, etc.) and may receive the information wirelessly: the puff duration predictor unit (which may be referred to herein as a puff duration predictor or puff duration predictor circuitry, or puff duration predictor control logic); the dose computation unit (which may be referred to herein as a dose computer or dose computer circuitry, or dose computer control logic); the dose delivery unit (which may be referred to herein as a vapor doser or vapor doser circuitry, or vapor doser control logic).

In general, any of these methods may also include computing and/or determining and delivering an amount of active ingredient. This may be performed using the concentration of active material within the source of vaporizable material, for example (e.g., giving the amount of active ingredient/unit mass or unit volume or the vaporizable material in the source of vaporizable material).

Any of these methods may also include determining a change in temperature ($\Delta T$) of the vaporizable material being vaporized for each of the sequential time intervals relative the temperature of the vaporizable material being vaporized.

Any appropriate time interval (dose time interval), which may be sequential (e.g., sequential time intervals) may be used, and may be based on or reflective of the sampling rate of the apparatus for determining the dose. For example, the time interval may be between about 200 msec and about 5 msec.

In general, delivering and/or estimating a partial dose may use the temperature of the vaporizable material being vaporized before the partial dose time interval comprises using an electrical property of the heater that is proportional to the temperature of the heater as the temperature of the vaporizable material being vaporized during a given partial dose time interval. Thus, the temperature referred to in any of the calculation steps described herein (e.g., the temperature of the vaporizable material being vaporized before the partial dose time interval) may refer to any value that is proportional to the actual temperature (e.g., using a temperature coefficient of resistance value to determine a value proportionally related to temperature, without requiring the conversion (using constants determined from the system to convert to C. or ° F.).

In general, the methods and apparatuses described herein may implement the resulting dose information (or partial, running or summed dose information), e.g., to report and/or control operation of the apparatus or transmit to a secondary (e.g., remote) apparatus. For example, any of these methods may also include real-time re-computing or re-estimation of the partial dose to be delivered by the (predicted) end of a given puff/trial or time period. Any of these methods (or devices configured to implement them) may further include calculating a cumulative total dose of vapor delivered over a session period that includes the time period. Thus, the total running dose over multiple puffs (each puff may be considered a time period, or the time period may be an entire session in which the apparatus is turned on for vaporizing the material, or multiple on periods until reset by the user, or a stage comprising a given number of puffs/trials).

In some embodiments, the time period may correspond to a duration of the user's puff.

Any appropriate material to be vaporized (vaporizable material) may be used. In general, the vaporizable material may be a liquid, or may be a solid, or may be a powder, or may be in the form of loose-leaf material, or it may be a combination of the abovementioned cases. The vaporizable material may comprise any active ingredient(s). For example, the vaporizable material may comprise a tobacco-based material. The vaporizable material may comprise a botanical. The vaporizable material may comprise a nicotine compound. The vaporizable material may comprise a cannabinoid. The vaporizable material may comprise one or more of cetirizine, ibuprofen, naproxen, omeprazole, doxylamine, diphenhydramine, melatonin, or meclizine. The vaporizable material may comprise one or more of albuterol, levalbuterol, pirbuterol, salmeterol, formoterol, atropine sulfate, ipratropium bromide, fluticasone, budesonide, mometasone, montelukast, zafirlukast, theophylline, fluticasone and salmeterol, budesonide and for moterol, or mometasone and formoterol. The vaporizable material may comprise one or more of a polyphonel, a green tea catechin, caffeine, a phenol, a glycoside, a labdane diterpenoid, yohimbine, a proanthocyanidin, terpene glycoside, an omega fatty acid, echinacoside, an alkaloid, isovaleric acid, a terpene, gamma-aminobutyric acid, a senna glycoside, cinnamaldehyde, or vitamin D. The vaporizable material may comprise a nicotine salt, glycerin, and propylene glycol. The vaporizable material may comprise loose leaf material, powders, solids. The vaporizable material may comprise active drugs or pharmacotherapeutics/pharmacological drugs (e.g., analgesics, immunosuppression drugs, caffeine, psychostimulants, benzodiazepines, tranquillizer, alcohol, etc.).

As mentioned, each of the following units, whenever present, may be part of a controller: the heater controller, the puff duration predictor unit, the dose computation unit, the dose delivery unit. In some variations, all or some of the abovementioned units are part of the same controller. In some variations some of the abovementioned units or systems are separate.

In some variations, only the dose computation unit is present. In some variations, only the heater controller and the dose computation unit are present.

An example of the methods of computing a dose of a vaporizable material to be delivered to a user of a vaporizing device over a puff (or during a puff duration or a time period) as described herein (e.g., wherein the time period or the puff duration comprises a plurality of sequential time intervals, and wherein the vaporizing device includes a heater controller, a heater, a source of the vaporizable material, a dose delivery unit, and a dose computation unit) may include: transmitting the value(s) of the previous estimated delivered dose(s) (e.g., the doses estimated (or measured) in the previous puff(s)/trial(s) or time period(s)) from the dose delivery unit to the dose computation unit; computing, (either in deterministic or in random or in pseudo-random way) the actual dose and, some doses to be delivered sequentially in the next puffs/trials, applying the following constraints: 1) the delivered average dose (e.g., the sum of the delivered or to be delivered doses in sequential puffs/trials divided by the number of the puffs/trials) has to be equal to a predetermined value or it can vary as desired, as will be described in greater detail herein; 2) each dose can take only values within a given/settable or predetermined range, and/or each dose difference can take only values within predetermined ranges, as will be described in greater detail herein.

An example of the methods of predicting the puff duration of the next (or the actual/incoming) puff in a vaporizing device, (e.g., wherein the vaporizing device includes a heater controller, a heater, a source of the vaporizable material, a puff sensor and a puff duration predictor unit) may include: training and computing a machine learning model (or reinforcement learning or artificial intelligence model broadly defined or a statistical model), wherein: a) in the training phase (which can be ran after each puff/trial (e.g., online mode) to dynamically update the model and improving its prediction performances after each puff, alternatively, the training phase can be computed periodically or only when certain conditions occur, or pseudo-randomly or randomly, for instance in a mini-batch mode, where the training phase occurs only after some puffs/trials and such trials are considered for the training), the model takes as labeled output the puff duration of the given/target puff/trial, and as the input (or input features) the puff durations and some other puffing topography features (such as, the average pressure drop within a puff, the average flow rate within a puff, and so on) of the puffs/trials immediately preceding the considered/target puff/trial and the corresponding delivered doses, and optionally, the actual computed dose to be deliver in the target puff/trial; b) in the prediction phase, the model predicts (as output) the puff duration of the next puff, and the model takes as input the puffing topography features (e.g., the puff duration, and, optionally, other features) of the puff(s)/trial(s) preceding the considered puff and the related delivered doses (and optionally, the computed dose to be deliver in the given puff/trial). It is worth mentioning that a broad spectrum of computational, statistical, autoregressive and/or machine learning algorithms can be adopted, such as, but not limited to: online learning algorithms (e.g., Stochastic Gradient Descent, Passive-Aggressive algorithms, recursive least squares, support vector machines, neural networks etc.), batch and mini-batch learning algorithms (support vector machines, kernel methods, gradient descent, any kind of regression, neural networks, etc.), incremental learning, progressive learning, Bayesian methods, pattern recognition, ARMA, statistical parametric and non-parametric models.

An example of the methods of computing and delivering a dose of a vaporizable material to a user of a vaporizing device over a time period (or puff/trial) as described herein (e.g., wherein the time period or puff duration comprises a plurality of sequential time intervals, and wherein the vaporizing device includes a heater controller, a puff sensor, a source of the vaporizable material, a puff duration predictor unit, a dose computation unit and a dose delivery unit) may include: transmitting from the puff duration predictor unit to the dose delivery unit the predicted puff duration for the given/target puff/trial during which a computed dose has to be delivered, computing the partial doses which have to be delivered in each sequential partial dose time intervals which form the total predicted puff duration (or time period), determining for each of the sequential time intervals the power that the heater controller has to deliver to the heater, wherein the power to be delivered and controlled to the heater for each of the sequential time intervals is calculated in the dose delivery unit from a temperature of the vaporizable material being vaporized immediately before the partial dose time interval, a flow rate measured by the puff sensor in the time interval immediately before the considered time interval and transmitted to the dose delivery unit, and the computed partial dose to be delivered during the partial dose time interval.

In certain embodiments, delivering a given (computed) amount of vapor/dose to the user during a given period of time (wherein the period of time may be the puff duration, and wherein such a period of time is determined by a sequential of successive time intervals) comprises calculating and delivering a power to the heater (controlled by the heater controller), based upon the following formula:

$$P_i = f(T_{i-1}, F_{i-1}, \widehat{\Delta m}_{i\;i}) = \alpha_1 \cdot T_{i-1} + \alpha_2 \cdot F_{i-1} + \alpha_3 \cdot \widehat{\Delta m}_{i\;i}$$

where $P_i$ is the power which has to be applied/delivered to the heater (by the heater controller) in the i-th time interval (e.g., in the actual time interval), $\widehat{\Delta m}_{i\;i}$ is the partial dose of vapor or material or active ingredients to be delivered in the i-th partial dose time interval (e.g., in the actual time interval), $\alpha_1$, $\alpha_2$, $\alpha_3$ are a constants which have to be determined empirically as will be described in great detail herein, $F_{i-1}$ is the measured flow rate in the (i−1)-th time interval (i.e., in the immediately preceding time interval), and is a measured temperature from an immediately preceding time interval.

In certain embodiments, the $P_i$ may be computed numerically, more specifically iteratively, as will be described in great details herein.

Any of these methods may also include detecting a user's puff on the vaporizer device, wherein the delivering steps are performed only during the detected puff.

In a certain embodiment, one of the methods to measure or estimate the amount of vapor generated from a vaporizable material within a vaporizing device, wherein the vaporizing device includes a heater controller, a puff sensor, a source of the vaporizable material, a puff duration predictor unit, a dose computation unit and a dose delivery unit, may consist in summing all the delivered partial doses, as computed by the dose delivery unit. More specifically, starting from the computed dose to be delivered during a given puff duration and from the predicted puff duration (wherein the predicted puff duration may be computed in the puff duration predictor unit and transmitted to the dose delivery unit), the dose delivery unit may compute the partial doses dividing the computed dose by the predicted puff duration, wherein the puff duration is expressed in units of partial dose time intervals, wherein each partial time intervals may be between 10 ms and 200 ms, such as 20 ms, or 25 ms, or 30 ms, etc., obtaining the partial dose to be delivered at each time intervals (i.e., $\Delta m_i$); after, the dose delivery unit may compute the power $P_i$ which has to be delivered to the heater for vaporizing the partial dose $\Delta m_i$ at each time interval (as described in a great detail herein) and, storing the partial sum of the partial doses delivered until the i-th time interval. Hence, if the actual puff duration involve a greater (smaller) number of partial time intervals than that computed in the predicted puff duration (predicted by the puff duration predictor unit), then the actual vaporized (or delivered) dose may be computed summing the actual delivered partial doses, so that the effectively (actual) delivered dose can be obtained, regardless the value of the predicted dose to be delivered and regardless the predicted puff duration. Only in case that the actual puff duration coincides with the predicted puff duration, the computed dose (obtained by the sum of the partial doses delivered at each sequential time interval) will be equal to the computed dose to be delivered during the puff (wherein the computed dose is computed in dose computation unit).

Another example of the methods of determining a dose of a vaporizable material delivered to a user of a vaporizing device over a time period as described herein (e.g., wherein the time period comprises a plurality of sequential time intervals, and wherein the vaporizing device includes a heater controller, a heater, a source of the vaporizable material including an active ingredient, a puff sensor, a dose computation unit and a dose delivery unit) may include: calculating, for each of the sequential time intervals, a partial dose, wherein the partial dose is calculated from a power delivered by the heater controller to the heater to vaporize the vaporizable material during a partial dose time interval, a temperature of the vaporizable material being vaporized immediately before the partial dose time interval and the flow rate measured from the puff sensor immediately before the partial dose time interval; summing the calculated partial doses in the dose delivery unit to determine a total dose of vapor delivered during the time period; and determining an amount of active ingredient delivered to the user based on the total dose of vapor delivered.

Any of these methods may also include transmitting the temperature of the vaporizable materials being vaporized during each of the plurality of sequential time intervals from the power controller to the dose delivery unit.

Any of these methods may also include transmitting the flow rate occurring during each of the plurality of sequential time intervals from the puff sensor to the dose delivery unit, or from the puff duration predictor unit to the dose delivery unit.

Any of these methods may also include detecting an amount of active ingredient delivered to the user based upon the determined amount of vapor. The measuring step may be performed at any appropriate frequency, such as a frequency of between 3 Hz and 60 Hz within the first period of time. The measuring steps may be performed at a frequency of between 10 Hz and 30 Hz within the first period of time.

Some of the methods for determining the amount of vapor delivered to the user during a given period of time (determined by a sequential of successive time intervals) may comprise calculating based upon the following formula:

$$\Delta m_{cum} = \sum_{i=1}^{i=n} \Delta m_i = g(P_i, T_{i-1}, F_{i-1}) = \sum_{i=1}^{i=n} \theta_1 P_i + \theta_2 T_{i-1} + \theta_3 F_{i-1}$$

where $\Delta m_{cum}$ is the total amount of vapor/material (or active ingredient) delivered to the user, $\Delta m_i$ is the partial dose delivered in the i-th partial dose time interval, $\theta_1$, $\theta_2$, $\theta_3$ are constants, $P_i$ is the power supplied during interval i, $T_{i-1}$ is a measured temperature for interval immediately before the current interval (i–1 immediately prior to interval i) and is flow rate reading for interval immediately before the current interval (i–1 immediately prior to interval i).

Also described herein are vaporization apparatuses, such as devices and systems, configured to compute and deliver sequences of successive doses of the vapor being delivered during sequences of puffs. For example, a vaporizer device may include: a heater controller; a heater coupled to the heater controller so that the heater controller applies power to the heater; a source of vaporizable material; a dose computation unit receiving input from a dose delivery unit, wherein the dose computation unit is configured to determine sequences of doses to be delivered in the next puffs subject to specific constraints (as it will be described in detail herein); a puff sensor; a puff duration predictor unit receiving input from the puff sensor, wherein the puff duration predictor unit is configured to estimate the puffing topography features (e.g., the average flow rate, the average pressure drop, the puff volume, the puff duration, etc.) and to predict the puff duration of the next puff; a dose delivery unit receiving input from the heater controller, from the dose computation unit, from the puff duration predictor unit, and from the puff sensor, wherein the dose delivery unit is configured to determine: 1) the power to apply to the heater for the delivery of a computed dose during a time puff duration (which comprises a sequence of partial dose time intervals); 2) the dose of vapor actually delivered to a user during a time period.

As mentioned, each or all or some of the following units may include a controller: the puff duration predictor unit, the dose computation unit, the dose delivery unit, the heater controller. For example, the puff duration predictor unit may be integral with the heater controller and/or with the dose delivery unit and/or with the dose computation unit. For example, the dose delivery unit may be integral with the heater controller and/or with and/or with the dose computation unit. The dose delivery unit may be configured to determine and to transmit the values of power at each of the sequential time intervals which form a puff duration (or a time period) to the heater (by communicating with the heater controller) for delivering to the user a given dose of vapor or material or active ingredients, computed or determined by the dose computation unit; moreover, the dose delivery unit may be configured to determine the actual amount of vapor or dose delivered.

In any of the apparatuses described herein, the partial dose time intervals or time intervals may each be between about 250 msec and about 10 msec.

As described herein, the dose delivery unit is configured to use an electrical property of the heater that is proportional to the temperature of the heater as the temperature of the vaporizable material being vaporized before the partial dose time interval.

Any of these apparatuses may include dose control logic configured to disable or to control the device (e.g., the heater) when the total dose of vapor delivered during a given time period meets or exceeds a preset or a dynamically computed threshold or value. The dose control logic may be part of the dose delivery unit.

Any of these apparatuses may also include a puff detector configured to detect a user puffing on the device. In some variations, the dose delivery unit may be configured to set the time period as a duration of a detected user's puff (e.g., between 0.5-15 sec, between 0.5-20 sec, between 0.5 to 5 seconds, etc.).

The source of vaporizable material may be a liquid or a solid or a gel or a loose-leaf material or a powder form or a combination of the abovementioned possibilities.

Other methods and apparatus variations are also described. For example, described herein are methods for computing, delivering and quantifying/estimating amounts of a vapor and/or one or more material(s) within the vapor that is delivered to a user from a reservoir of vaporizable material in an electronic vaporizer device. The electronic vaporizer device may include a puff sensor, a power source (e.g., battery, capacitor, etc.), a heating element controller, a heating element. A separate temperature sensor may also be included, or it may be part of the heating element controller, which may estimate temperature of the heating element (e.g., resistive coil, etc.) based on a change in resistance due to temperature (e.g., TCR), and may therefore include a reference resistor. One or more additional temperature sensors may also be included.

These apparatuses may also include a dose computation unit, a puff duration predictor unit and a dose delivery unit and/or controlling logic for controlling operation of the apparatus based on the determined/estimated dosage(s) (e.g., determining and delivering the successive dose of vapor or of active ingredients during the next puff(s)/trial(s), etc.).

For example, a method of operating the device may include: a puff sensor detecting a user's puff and measuring the puff flow rate (and optionally other quantities related to a puff, such as a pressure drop), the heating element controller delivering a power from the power source during the user's puff (e.g., at multiple discrete time intervals during the puff); the temperature sensor measuring a temperature or a temperature profile of the material being vaporized (e.g., at or near the heating element) during the user's puff; a puff duration predictor unit estimating/predicting the next user puff duration; a dose computation unit: a) computing the dose(s) to be delivered on the basis of the previous delivered doses or on the basis of quantities/values related to the previous delivered doses and some constraints (as described in detail herein); b) computing and delivering the partial doses over the sequentially successive time intervals forming the predicted puff duration, by delivering a computed power to the heater (by the heating controller) at each of the sequential time intervals of the puff duration; moreover, the dose delivery unit may calculate the amount of the vapor delivered to the user from the vaporizable material based upon the amount of the power, the flow rate and the temperature profile during the user's puff. In certain embodiments, the method comprises storing a plurality of measurements of temperature, temperature profiles, amount of power delivered, flow rate profiles, or a combination thereof, in a memory unit.

In certain embodiments, the electronic vaporizer device comprises a timer, and the method may comprise engaging the timer to measure a puff duration. In certain embodiments, the method comprises storing a plurality of measurements of temperature, temperature profiles, amount of power delivered, puff duration and (optionally) other puffing topography features or a combination thereof in a memory unit. In certain embodiments, the method comprises normalizing the amount of the vapor delivered to the user to the puff duration. In certain embodiments, the method comprises attaching a separate pod to the device, the separate pod configured to hold a vaporizable material. In certain embodiments, the method comprises calculating the amount of the vapor delivered (or to be deliver) to a user from the vaporizable material in milligrams of total particulate matter. In certain embodiments, the method comprises calculating the amount of the vapor delivered (or to be delivered) to a user from the vaporizable material in milligrams of an active ingredient. In certain embodiments, the electronic vaporizer device comprises a heating reservoir distinct from the heating element, and the method comprises preheating a vaporizable material to a preset temperature. In certain embodiments, the vaporizable material is a liquid, viscous liquid, wax or solid, or powder, or a pod, or loose-leaf material. In certain embodiments, the vaporizable material is a tobacco-based material. In certain embodiments, the vaporizable material is a botanical. In certain embodiments, the vaporizable material is a medicinal compound. In certain embodiments, the vaporizable material is nicotine. In certain embodiments, the vaporizable material is a cannabinoid. In certain embodiments, the vaporizable material is *Cannabis*. In certain embodiments, the method comprises adjusting a type of the vaporizable material. In certain embodiments, the method comprises adjusting the type of the vaporizable material to a liquid, viscous liquid, powder, wax or loose-leaf material. In certain embodiments, the method comprises adjusting the type of the vaporizable material to a tobacco-based material.

In certain embodiments, the method comprises adjusting the type of the vaporizable material to a botanical. In certain embodiments, the method comprises adjusting the type of the vaporizable material to a medicinal compound. In certain embodiments, the method comprises adjusting the type of the vaporizable material to nicotine. In certain embodiments, the method comprises adjusting the type of the vaporizable material to a cannabinoid. In certain embodiments, the method comprises adjusting the type of the vaporizable material to *Cannabis*. Adjusting the vaporizable material may include adjusting the apparatus or method to account for the change in constants and/or calibrating the apparatus to account for changes in the constants that may be used to give a calibrated (e.g., mass or mass/time) output, as described in greater detail herein.

In a certain embodiment provided herein, is an electronic vaporizer device configured to deliver varying doses of vapor/material (including drugs or active substances or ingredients) in sequentially and in deterministic or random or in pseudo-random order, wherein the doses of a vapor are delivered to a user from a vaporizable material in the electronic vaporizer device, wherein the electronic vaporizer device comprises: a puff sensor configured to detect a user's puff and to measure the flow rate and, optionally, some puffing features (e.g., the pressure drop), an heating element controller configured to measure and control an amount of power delivered from a power source during the user's puff, a temperature sensor configured to measure a temperature or a temperature profile generated by a heating element during the user's puff, a dose delivery unit configured to compute and deliver to the heater (through the heater controller) a power profile or an energy profile in order to vaporize a computed dose on a given puff/trial. The doses are sequentially delivered in each of the sequential puffs/trials such that, starting from a given or predetermined (even randomly) trial, the average positive dose difference is greater in magnitude than the average negative dose difference, subject to the constraint that the average cumulative administered or inhaled dose (i.e., the sum of the doses delivered over successive puffs/trials divided by the number of trials) is kept constant or equal to a predetermined value over time (or over successive puffs/trials) or it is reduced (or it is varied and set as desired), and subject to the constraint that each dose can take only values within a given/settable (or predetermined) range, and/or subject to the constraint that a dose difference can assume values within predetermined ranges, wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

In a certain embodiment provided herein, is an electronic vaporizer device configured to compute, deliver, control and quantify a succession of varying doses of a vapor for a plurality of sequential puffs/trials, wherein the vapor doses are delivered to a user from a vaporizable material in the electronic vaporizer device, wherein the electronic vaporizer device comprises: a puff sensor configured to detect a user's puff and to measure the puff flow rate; an heating element controller configured to control an amount of power delivered from a power source during the user's puff; a temperature sensor configured to measure a temperature or a temperature profile generated by an heating element during the user's puff; a dose delivery unit configured to: 1) compute and transmit power values to the heater controller which has to be applied said power values to the heater element in order to vaporize a computed dose during the puff duration, 2) calculate/estimate the amount of the vapor delivered to the user from the vaporizable material based upon the partial doses delivered during the puff, or based upon the amount of the power, the temperature and the puff flow rate during the user's puff; and one or more of a) a puff duration predictor unit configured to compute/extract the puffing topography features (e.g., the puff duration) and to predict the next or the actual puff duration (i.e., to predict the puff duration of the next/incoming puff); b) a dose computation unit configured to compute the actual or the next vapor (or material or TPM, or active ingredients) dose(s), in relation to the previous delivered dose(s), satisfying the following conditions: 1) starting from a given (or predetermined) trial, the average positive dose difference is greater in magnitude than the average negative dose difference, 2) the average cumulative administered dose (i.e., the sum of the doses delivered over successive puffs/trials divided by the number of trials) is kept constant over successive trials, or it is reduced or it is varied as desired, 3) each dose can take only values within a given/settable or predetermined range, and/or each dose difference can take only values within predetermined ranges, wherein a dose difference is defined as the difference between the dose of vapor or material delivered (or to be delivered) in a given puff/trial and the dose delivered in the trial immediately before, or as the difference between the dose delivered in a given trial and a linear combination of some of the sequentially delivered or inhaled doses in the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences; wherein the number of puffs/trials for the evaluation/estimation of the average cumulative dose and for the average positive and negative dose difference can be considered, for example, to within about 12, or to within about 10, or to within about 6, or to within about 20, or to within about 100, or to within about 50, or to within about 1000, or as an incremental number of trials as the number of puffs advances etc.; c) a dose delivery unit configured to compute the partial doses which have to be delivered sequentially for each of the plurality of sequential time intervals within the (predicted) puff duration, on the basis of the dose computed by the dose computation unit and on the basis of the puff duration predicted by the puff topography predictor unit; moreover, the dose delivery unit is also configured to compute the power profile i.e., the power values for each of the sequential time intervals forming the puff duration, to deliver to the heater (by means the heater controller) in order to deliver the computed dose of vapor (or material or active ingredients). In certain embodiments, the electronic vaporizer device comprises a memory unit, configured to store a plurality of measurements of temperature, temperature profile, power delivered, or a combination thereof, puffing topography features (e.g., puff duration, average pressure drop, flow rates, puff volume, etc.), and the delivered dose, or a combination thereof. In certain embodiments, the electronic vaporizer device comprises a timer configured to determine a puff duration. In certain embodiments, the electronic vaporizer device comprises a memory unit, configured to store a plurality of measurements of temperature, temperature profile, power delivered, puff duration or a combination thereof. In certain embodiments, the electronic vaporizer device comprises a memory unit, configured to store a plurality of measurements of temperature, temperature profile, power delivered, puff duration, delivered doses, and optionally some mathematical quantities derived from them, and optionally puffing topography features, or a combination thereof.

In certain embodiments, the electronic vaporizer device is configured to normalize the amount of the vapor delivered to the user to the puff duration.

In certain embodiments, the electronic vaporizer device comprises a separate pod attached to the device, the separate pod configured to hold a vaporizable material.

In certain embodiments, the electronic vaporizer device is configured to calculate and/or deliver the amount of the vapor delivered to the user from a vaporizable material in milligrams of total particulate matter. In certain embodiments, the electronic vaporizer device is configured to calculate and/or deliver the amount of the vapor delivered to the user from a vaporizable material in milligrams of total particulate matter.

In certain embodiments, the electronic vaporizer device comprises an heating reservoir distinct from the heating element. In certain embodiments, the electronic vaporizer device comprises a vaporizable material that is a liquid, viscous liquid, powder, pod, solid, wax, or loose-leaf material or a combination thereof. In certain embodiments, the electronic vaporizer device comprises a vaporizable material that is a tobacco-based material. In certain embodiments, the electronic vaporizer device comprises more than one material reservoirs. In certain embodiments, the electronic vaporizer device comprises a vaporizable material that is a botanical. In certain embodiments, the electronic vaporizer device comprises a vaporizable material that is a medicinal compound. In certain embodiments, the electronic vaporizer device comprises a vaporizable material that is nicotine. In certain embodiments, the electronic vaporizer device comprises a vaporizable material that is a cannabinoid. In certain embodiments, the electronic vaporizer device comprises a vaporizable material that is *Cannabis*. In certain embodiments, the electronic vaporizer device is configured to allow adjustment of a type of the vaporizable material. In certain embodiments, the type of the vaporizable material is adjustable to a liquid, viscous liquid, solid, powder, wax or loose-leaf material. In certain embodiments, the type of the vaporizable material is adjustable to a tobacco-based material. In certain embodiments, the type of the vaporizable material is adjustable to a botanical. In certain embodiments, the type of the vaporizable material is adjustable to a medicinal compound. In certain embodiments, the type of the vaporizable material is adjustable to nicotine. In certain embodiments, the type of the vaporizable material is adjustable to a cannabinoid. In certain embodiments, the type of the vaporizable material is adjustable to *Cannabis*. In certain embodiments, the controlling logic comprises a Software module. In certain embodiments, the controlling logic comprises a hardware element. In certain embodiments, the electronic vaporizer device comprises a display unit, configured to provide feedback to the user. In certain embodiments, the electronic vaporizer device is a single-use electronic vaporizer device. In certain embodiments, the electronic vaporizer device is a vaporizing device. In certain embodiments, the electronic vaporizer device is a THS device. In certain embodiments, the electronic vaporizer device is an e-cigarette.

In a certain embodiment provided herein, is a method, the method comprising an electronic vaporizer device configured to compute, deliver, and quantify an amount of a vapor delivered (and/or to be delivered) to a user from a vaporizable material in the electronic vaporizer device, wherein the electronic vaporizer device comprises: a puff sensor configured to detect a user's puff and to measure the puff flow rate and, eventually, some puff characteristics (e.g., the puff volume, the pressure drop, etc.); an heating element controller configured to control an amount of power delivered from a power source during the user's puff; a temperature sensor configured to measure a temperature or a temperature profile generated by a heating element during the user's puff; a dose computation unit configured to compute the actual or the next vapor (or material or TPM, or active ingredients) dose(s), in relation to the previous delivered doses, satisfying the following conditions: 1) the average positive dose difference is greater in magnitude than the average negative dose difference, 2) the average cumulative administered dose (i.e., the sum of the doses delivered over successive puffs/trials divided by the number of trials) is kept constant over time or it is reduced or it is imposed to vary as desired, 3) the doses are constrained to assume values within a range determined by a settable or predetermined minimum value and a settable or predetermined maximum value, and/or each dose difference can only take values within settable or predetermined ranges; a dose delivery unit configured to compute the partial doses which have to be delivered sequentially for each of the plurality of sequential time intervals which form the (predicted) puff duration, on the basis of the dose computed by the dose computation unit and based on the puff duration predicted by the puff duration predictor unit, moreover, the dose delivery unit is also configured to compute the power profile i.e., the power values for each of the sequential time intervals forming the puff duration, to apply/deliver to the heater (by means the heater controller) in order to deliver the computed dose of vapor (or material or active ingredients).

In certain embodiments, the electronic vaporizer device comprises a memory unit, configured to store a plurality of measurements of temperature, temperature profile, power delivered, or a combination thereof, puffing topography features (e.g., puff duration, average pressure drop, flow rates, puff volume, etc.), and the delivered dose, or a combination thereof. In certain embodiments, the electronic vaporizer device comprises a timer configured to determine a puff duration. In certain embodiments, the electronic vaporizer device comprises a memory unit, configured to store a plurality of measurements of temperature, temperature profile, power delivered, puff duration or a combination thereof. In certain embodiments, the electronic vaporizer device comprises a memory unit, configured to store a plurality of measurements of temperature, temperature profile, power delivered, puff duration, delivered doses, and optionally some mathematical quantities derived from them, and optionally puffing topography features, or a combination thereof.

In certain embodiments, the electronic vaporizer device is configured to normalize the amount of the vapor delivered to the user to the puff duration. In certain embodiments, the electronic vaporizer device comprises a separate pod attached to the device, the separate pod configured to hold a vaporizable material. In certain embodiments, the electronic vaporizer device is configured to calculate and deliver sequentially, to the user, varying amounts of vapor from a vaporizable material in milligrams of total particulate matter. In certain embodiments, the electronic vaporizer device is configured to deliver and to calculate the amount of the vapor to be delivered to the user from a vaporizable material in milligrams of total particulate matter. In certain embodiments, the electronic vaporizer device comprises an heating reservoir distinct from the heating element. In certain embodiments, the electronic vaporizer device comprises a vaporizable material that is a liquid, viscous liquid, powder, pod, solid, wax, or loose-leaf material or a combination thereof. In certain embodiments, the electronic vaporizer device comprises a vaporizable material that is a tobacco-based material. In certain embodiments, the electronic vaporizer device comprises more than one reservoir for the material to be vaporized and more than one drugs or substances. In certain embodiments, the electronic vaporizer device comprises a vaporizable material that is a botanical. In certain embodiments, the electronic vaporizer device comprises a vaporizable material that is a medicinal compound. In certain embodiments, the electronic vaporizer device comprises a vaporizable material that is nicotine. In certain embodiments, the electronic vaporizer device comprises a vaporizable material that is a cannabinoid. In certain embodiments, the electronic vaporizer device comprises a vaporizable material that is *Cannabis*. In certain embodiments, the electronic vaporizer device is configured to allow adjustment of a type of the vaporizable material. In certain embodiments, the type of the vaporizable material is adjustable to a liquid, viscous liquid, solid, powder, wax or loose-leaf material. In certain embodiments, the type of the vaporizable material is adjustable to a tobacco-based material. In certain embodiments, the type of the vaporizable material is adjustable to a botanical. In certain embodiments, the type of the vaporizable material is adjustable to a medicinal compound. In certain embodiments, the type of the vaporizable material is adjustable to nicotine. In certain embodiments, the type of the vaporizable material is adjustable to a cannabinoid. In certain embodiments, the type of the vaporizable material is adjustable to *Cannabis*. In certain embodiments, the electronic vaporizer device comprises a display unit, configured to provide feedback to the user. In certain embodiments, the electronic vaporizer device is a single-use electronic vaporizer device. In certain embodiments, the electronic vaporizer device is a vaporizing device.

Without desired to be bound by the theory, it is known that the user's experience (including satisfaction, product or treatment acceptance, rewarding effects, psychological rewarding, neurophysiological effects at the level of the central nervous system) is affected by the perceived (even implicitly and in part unconsciously) effects of the inhaled active substance (or drug or material or ingredients). In fact, the inventors have unexpectedly identified methods for modulating (e.g., increasing) such perception by means the delivery of sequential varying doses of drug or vapor for each of the sequential puffs/trials. In particular, each puff determines a compounds of psychological and physiological effects, and the overall effect determined by a given puff is determined by both active and reactive contributions. Active contributions are represented by the effects determined by the neurophysiological active ingredients (e.g., nicotine effects at the central nervous system), while reactive contributions are represented by conditioned responses and reinforced cues (e.g., chemosensory features, flavors, conditioned reward effects, etc.) and some of the same active effects which have been conditioned (this phenomenon is termed mimicking or pharmacological mimicking). The methods and apparatuses disclosed herein may be able to enhance the reactive contributions. Without desiring to be bound by any theory, it is believed that such an enhancement is due to a process of unconditioned stimulus (UCS) inflation (i.e., enhancement, or increase), determined by a continuous and dynamical stimulus revaluation driven by weighted prediction errors within the central nervous system (the computation of a prediction error may occur unconsciously and implicitly within the central nervous system, and it is based on the difference of the effects expected by a given stimulus (or previously experienced) and the effects actually perceived or experienced or determined). It is expected that the weight of a prediction error within the central nervous system, represents the neural gain which is assigned to the prediction error before it can update the reactive response associated to the neural representation of a given stimulus. Such a weight depends on different features, such as the environment uncertainty, the uncertainty of the expected effects, the uncertainty of the experienced effects, the magnitude of the stimulus, the magnitude of the effects determined by a given stimulus, the contrast effects, the magnitude of the prediction error itself, and others. If all the variables outside the magnitude (or the intensity) of the stimulation are deemed constant, then the modulation of the magnitude of the stimulation (or its effects) does permit to modulate the weights of the prediction errors, for instance, enhancing the positive weighted prediction errors while reducing the negative weighted prediction errors, over successive sequential trials, so that, the reactive contributions of the effects produced by the given stimulus can be enhanced cumulatively. The methods and apparatuses disclosed herein, in some embodiments, may compute the sequential partial doses to be delivered on each of the sequential puff/trial in a random or in a pseudo-random way, so that the environment uncertainty can be considered constant over time. Moreover, the methods and apparatuses disclosed herein, in some embodiments, may predict the puffing features (e.g., the puff duration) of the next or incoming puff, in which the computed dose has to be delivered; one of the benefit of such a feature is that it is possible to deliver a predetermined or a pre-computed dose of vapor, another benefit of such a feature is that the user experiences an improved consistency of vapor delivery over the entire puff duration, even if the dose to be delivered has previously been computed and defined.

Hence, one of the features of the vapor inhalation devices and other apparatuses and methods described in this disclosure is to deliver successive and sequential doses of vapor/material (including active ingredients, drugs, and substances) such that the average positive dose difference is greater in magnitude than the average negative dose difference, subject to the constraint that the average cumulative administered dose (i.e., the sum of the doses delivered over successive puffs/trials divided by the number of trials) is kept constant over time or it is reduced (or it is imposed/set as desired), and subject to the constraint that each dose can take only values within a given/settable (or predetermined) range, and/or subject to the constraint that a dose difference can assume values within predetermined ranges, wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

It is worth noting that the methods and apparatuses disclosed herein can be applied to every kind of electronic vaporizers, electronic inhalers, or electronic devices able to deliver a dose of material to be inhaled (even if the considered device does not include an heater and the vaporization of material is produced in different ways, such as, for instance, by (micro)droplet ejection). Whenever the methods and apparatuses disclosed herein are applied to an electronic device which does not include an heater (e.g., droplet ejection device, for example a bubble jet or piezoelectric device, for example see U.S. Pat. No. 5,894,841), the electrical quantities to be controlled for measuring or estimating or predicting a delivered/inhaled (or to be delivered) dose may be different, nevertheless, the methods disclosed herein for delivering varying doses over sequential puffs/trials remain applicable whatever be the implemented vaporization technique or technology, wherein the delivery of varying doses in sequential puffs/trials is computed such that starting from a given or predetermined (even randomly) trial, the average positive dose difference is greater in magnitude than the average negative dose difference, subject to the constraint that the average cumulative administered or inhaled dose (i.e., the sum of the doses delivered over successive puffs/trials divided by the number of trials) is kept constant or equal to a predetermined value over time (or over successive puffs/trials) or it is reduced (or it is varied and set as desired), and subject to the constraint that each dose can take only values within a given/settable (or predetermined) range, and/or subject to the constraint that a dose difference can assume values within predetermined ranges, wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

In some embodiments, disclosed herein are methods and apparatuses that allow or facilitate a user in smoke cessation or in reducing a given substance addiction (e.g., nicotine addiction) or in smoke reduction. In particular, in some embodiments, a method for smoke cessation or smoke reduction or nicotine addiction reduction may include: calculating and delivering varying doses of vapor (or material or active ingredients) to a user over sequential puffs/trials, such that, starting from a given trial, the average positive dose difference is greater in magnitude than the average negative dose difference, subject to the constraint that the average cumulative administered dose (i.e., the sum of the doses delivered over successive puffs/trials divided by the number of trials) of active drug or of active physiological principle or of active ingredients is gradually reduced (e.g., by reducing the vapor, or the TPM, or the concentration of the active substance in the liquid compound of vaporizable material), and subject to the constraint that a dose can only assume values within a given range delimited by a settable or predetermined maximum value and a settable or predetermined minimum value, and/or subject to the constraint that a dose difference can assume values within predetermined or settable ranges; wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences. Without desiring to be bound by any theory, it is argued that increasing the reactive contributions (i.e., the neurophysiological effects due to classical conditioning and/or reinforcement and/or unconditioned stimulus revaluation) while reducing the active contributions (i.e., the effects provoked by the active ingredients of the drug) may determine a reduction in the physical addiction. Moreover, after the accomplishment of the abovementioned procedure, a decreasing of the reactive contributions can be employed, in order to extinguish the reactive responses/effects (which, in general, may be resistant-to-extinction, so that it could not be sufficient to extinguish them by simply performing a progressive reduction of the active delivered doses without accomplishing a proper schedule for the reactive contributions reduction), and the method may include: calculating and delivering varying doses of vapor (or material or active ingredients) to be delivered over sequential puffs/trials, such that, starting from a given (predetermined) trial, the average positive dose difference is smaller in magnitude than the average negative dose difference, subject to the constraint that the average cumulative delivered dose (i.e., the sum of the doses delivered over successive puffs/trials divided by the number of trials) of active drug or of active physiological principle or of active ingredients is kept constant or gradually reduced (or set up as desired), subject to the constraint that a dose can only assume values within a predetermined range delimited by a settable or predetermined maximum value and a settable or predetermined minimum value, and/or subject to the constraint that a dose difference can assume values within predetermined ranges; wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

In some embodiments, disclosed herein are methods and apparatuses comprising an electronic inhalation device (e.g., e-cigarette, THS, vaporizer, aerosol generator, medicament delivery device, etc.), configured to deliver successive and sequential doses of vapor/material (including active ingredients, drugs, and substances) such that the average positive dose difference is greater in magnitude than the average negative dose difference, subject to the constraint that the average cumulative administered dose (i.e., the sum of the doses delivered over successive puffs/trials divided by the number of trials, wherein the considered number of trials can range from 2 to about 10, or to about 20, or to within about 100 (e.g., within about 90, within about 80, within about 75, etc.) or to within about 1000, or to within about 5000 or as a progressive and unbounded number of trials) is kept constant over time or over successive trials, or it is reduced, wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences. In certain embodiments a trial may correspond to a puff duration. In some embodiments a stage may correspond to about 10 puffs duration. In some embodiments a stage may correspond to about 12 puffs duration. In some embodiments a stage may correspond to about 20 puffs duration. In some embodiments a stage may corresponds to about 30 puffs duration. In some embodiments a stage may correspond to about 1 day. In some embodiments a stage may correspond to a time period or to a time period of device activity or to a time period of active user's utilization of the device. In some embodiments a stage may correspond to a full consumable unit (e.g., a tobacco stick, a tobacco pod, a pod, a portion of loose-leaf material, etc.). In some embodiments a stage may correspond to the consumption and/or adoption/inhalation (at least partially) of a tobacco stick (or tobacco pod, or tobacco cigarette). In some embodiments a stage may correspond to the time needed to consume or to inhale a given portion or quantity of material (e.g., drug, nicotine, tobacco, etc.).

One of the features of the electronic medicament delivery devices or systems and other apparatuses and methods described in this disclosure is to deliver successive and sequential doses of material (including active ingredients, drugs, and substances) in a deterministic or random or pseudo-random order, such that the average positive dose difference is greater in magnitude than the average negative dose difference, subject to the constraint that the average cumulative administered dose (i.e., the sum of the doses delivered over successive trials divided by the number of trials) is kept constant or equal to a predetermined value over time (or over successive trials) or it is reduced (or it is varied and set as desired), and subject to the constraint that each dose can take only values within a settable (or predetermined) range, and/or subject to the constraint that a dose difference can assume values within predetermined ranges, wherein a dose difference is defined as the difference between the dose of substance (including active ingredients) delivered in a given trial and the dose delivered in the trial immediately before, or as the difference between the dose delivered in a given trial and a liner combination of the doses delivered sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

It is worth noting that the methods and apparatuses disclosed herein can be applied to every kind of electronic medicament delivery devices able to deliver a dose of substance to an user. The methods and apparatuses disclosed herein may be applied to any electronic delivery devices that do not include an heater (for instance, as few non-limiting examples it can be cited: droplet ejection devices, pump-based devices, patient-controlled analgesia devices, etc.); in fact, the methods disclosed herein for delivering varying doses over sequential trials remain applicable whatever be the implemented electronic delivery technique or technology, wherein the delivery of varying doses in sequential trials is computed such that the average positive dose difference is greater in magnitude than the average negative dose difference, subject to the constraint that the average cumulative administered dose (i.e., the sum of the doses delivered over successive trials divided by the number of trials) is kept constant or equal to a predetermined value over time (or over successive trials) or it is reduced (or it is varied and set as desired), and subject to the constraint that each dose can take only values within a settable or predetermined range, and/or subject to the constraint that a dose difference can assume values within predetermined ranges, wherein a dose difference is defined as the difference between the dose of substance (including active ingredients) delivered in a given trial and the dose delivered in the trial immediately before, or as the difference between the dose delivered in a given trial and a liner combination of the doses sequentially delivered in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

Without desiring to be bound or limited by the considerations mentioned below, it is believed that the dose computing and delivery systems and methods disclosed herein may be valid for all the systems and devices which deliver drugs, substances, active ingredients that acts in some way within the central nervous system, and/or within systems strictly related and in communication with the central nervous system (such as, for example, the immune system).

BRIEF DESCRIPTION OF THE DRAWINGS

The novel features of the invention are set forth with particularity in the description. Like numbers refer to like elements throughout the description of the figures. A better understanding of the features and advantages of the present invention will be obtained by reference to the following detailed description that sets forth illustrative embodiments, in which the principles of the invention are utilized, and the accompanying drawings (also "figure" and "FIG." herein), of which.

DETAILED DESCRIPTION

Figure 1:
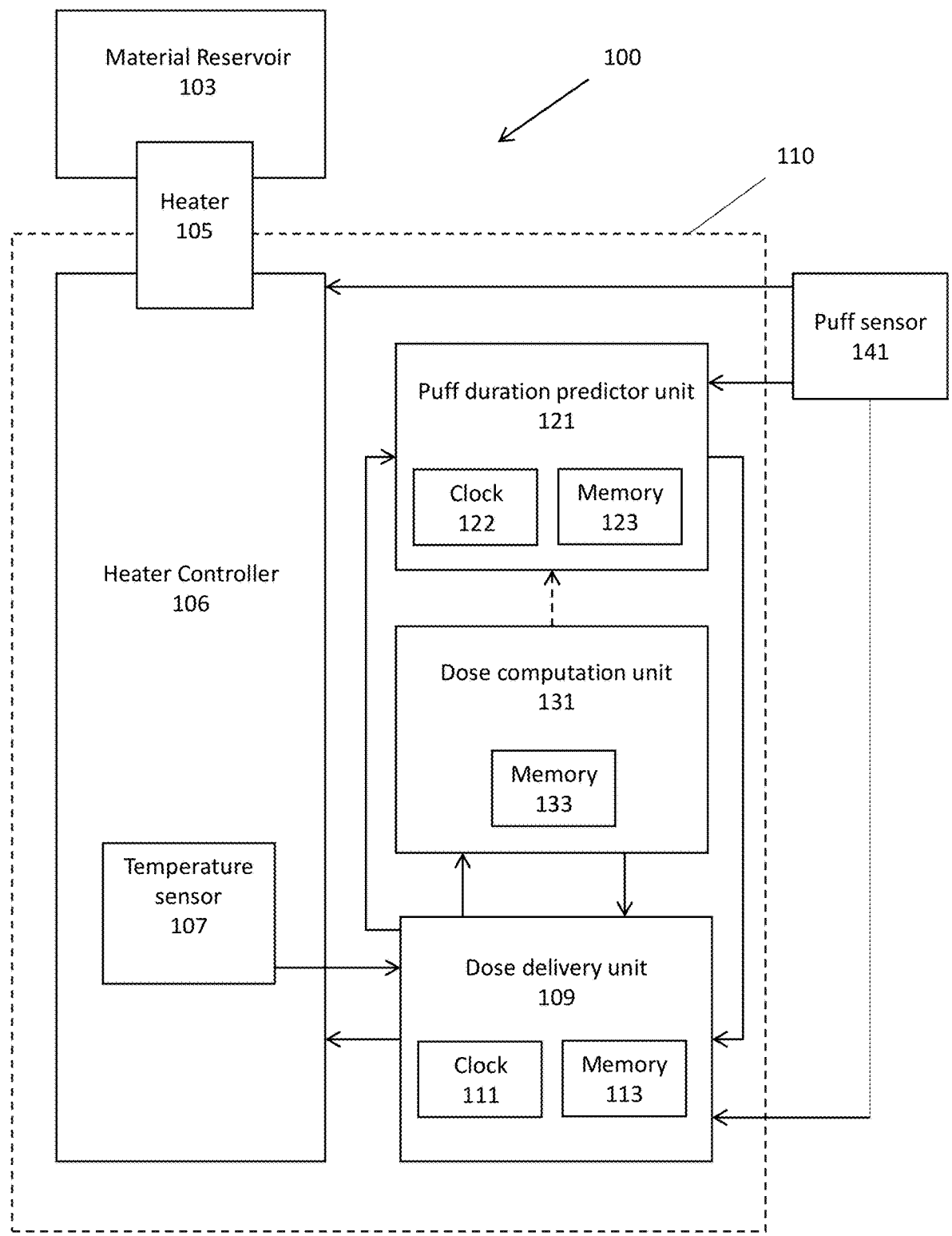
FIG. 1 is a schematic of a vaporizing apparatus including a dose computation unit, a puff duration predictor unit, a dose delivery unit.

The following detailed description of the invention is merely exemplary in nature and is not intended to limit the invention or the application and uses of the invention. Furthermore, there is no intention to be bound by any theory presented in the preceding background of the invention or the following detailed description of the invention.

The embodiments of the disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law.

The present disclosure provides methods and or apparatuses or systems for computing and delivering successive amounts of a drug or substance (including active ingredients) to a user in an electronic medicament delivery device, comprising computing doses that are sequentially administered in each of the sequential trials (e.g., self-administration trials, automatically released doses in sequential administration trials, timed doses release trials, etc.), in deterministic or in random or pseudo-random order, such that the average positive dose difference is greater in magnitude than the average negative dose difference, subject to the constraint that the average cumulative administered dose (i.e., the sum of the doses delivered over successive trials divided by the number of trials) is kept constant or equal to a predetermined value over time (or over successive trials) or it is reduced (or it is varied and set as desired), and subject to the constraint that each dose can take only values within a settable or predetermined range, and/or subject to the constraint that a dose difference can assume values within predetermined ranges, wherein a dose difference is defined as the difference between the dose of substance (including active ingredients and drugs) delivered in a given trial and the dose delivered in the trial immediately before, or as the difference between the dose delivered in a given trial and a liner combination of the doses delivered sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

In certain embodiments, the present disclosure provides a method for computing, delivering, controlling and quantifying successive amounts of a vapor delivered to a user from a vaporizable material in an electronic vaporizer device comprising (not necessarily in the following order): a) estimating the vaporizable material intake evaporated, aerosolized or vaporized from a vaporizable material in a vaporizing device or electronic vaporizer device, b) predicting the puff duration of the puff in the incoming (or in the next) puff/trial taking into account the puffing features and the doses delivered in the trials immediately before, c) computing the doses to be delivered sequentially in successive puffs/trials, d) computing the partial doses to be delivered at each partial dose time interval within a given puff/trial time period, e) computing the power to be delivered and controlled at the heating element at each partial dose time interval within a given puff/trial time period. Also provided in this disclosure are calibration methods that may include establishing a relationship of total particulate matter (TPM) vaporized from a vaporizable material as a function of temperature generated, power consumed and puff flow rate, and/or establishing a relationship of power (or energy) applied to an heater and TPM. Others calibration methods known in the art may be adopted with the embodiments disclosed herein. Calibration may be performed one time (e.g., at a factory) or it may be performed by the user. Alternatively, or additionally, the user may be requested or required to perform a calibration step that include inputting an identifier of the material be vaporized (e.g., selecting or inputting the material and/or concentration, or a reference identified, such as a lot number or the like that can be linked to the material being vaporized). For example, a user may scan (e.g., using a QR code, bar code, or equivalent) the vaporizable material or packing and/or inserts affiliated with the vaporizable material. In some variations the apparatus includes a look-up table corresponding to a variety of vaporizable materials that may include values for calibrating the apparatus, including the constants referred to herein that may be used to calibrate the mass of the vapor and/or one or more components (e.g., active agents/active ingredients) in the vaporizable material.

The term "vape" or "vaping", as used herein, refers to the action of or the experience of using a vaporization device, such as an electronic vaporizer device for the delivery of vapor to a user.

The term "puff" refers to the process of removing vapor from a vaporization device or e-vaporizer device using a suction mechanism. In certain embodiments, the suction mechanism is a user. In certain embodiments, the suction mechanism is an analytical smoking machine. Commonly used synonyms for puff are drag, draw, hit, suck, pull, inhale, or smoke for example.

The terms: "trial" or "administration/trial" or "administration trial" are considered herein synonyms and they refer to the time at which a given dose is released or delivered or administered to a user from a given electronic medicament delivery device.

The term "puff/trial" as used herein, refers to a trial in which a puff occurs, or it refers to the time at which a puff starts or occurs.

As used herein a "dose" (or "active dose") may refer to the amount or quantity of the vapor and/or material (e.g., active ingredient(s), drugs, etc.) taken (or delivered) at a particular time or administration trial or puff/trial. The dose may be quantified as a mass, or a mass/time, depending on the context. The dose may be dose/puff or dose/trial.

As used herein the term "reactive response" or "reactive contribution", represents all the effects or contributions produced by the administration (e.g., puff, or self-administration) of a given substance and/or the associated stimuli (e.g., chemosensory cues, flavors, conditioned stimuli, etc.) which are not directly due to the effects of the active ingredients. For instance, a conditioned stimulus (e.g., a sound or a flavor associated to the administration of a given substance), can produce only reactive responses or reactive contributions. In such an example, the reactive response is due to endogenous substances (for instance, endogenous opioids) and not directly to the active effects of an exogenous substance. It is worth noting that a conditioned stimulus (e.g., a sound or a flavor) associated with the administration of a given substance (e.g., cocaine), may determine a reactive response of the same type of the response elicited by the administration of the active drug (e.g., involving the same neurotransmitters and the same receptors within the central nervous system), nevertheless this occurs by means endogenous substances and not through the effects of an exogenous active ingredient (such a phenomenon is known as "pharmacological mimicking" or "reactive mimicking", see: Placebo response is driven by ucs revaluation: evidence, neurophysiological consequences and a quantitative model. Scientific reports, 6, 28991.). Operationally, for a given user who has assumed a given substance for a certain number of trials, the reactive contribution may be experienced and/or assessed in the absence of its active counterpart, if a "similar" substance or drug but without active ingredients (e.g., without nicotine), is openly administered to the user; wherein the term "similar" indicates that the administered substance possesses the same flavors, odors, and cues of the original drug and that the administration occurs with the same rituals (e.g., vaporization).

As used herein the term "apparent dose" represents an abstract amount or quantity of vapor and/or material (e.g., active ingredients, drug, etc.) which is actually perceived by the central nervous system of an user. Such a quantity is generally different (e.g., greater) than the active delivered dose. For instance, if an active dose of a drug is administered in an hidden mode to an user, its effect is lower than if the same dose is administered openly (see Benedetti, F., Maggi, G., Lopiano, L., Lanotte, M., Rainero, I., Vighetti, S., & Pollo, A. (2003). Open versus hidden medical treatments: The patient's knowledge about a therapy affects the therapy outcome. Prevention & Treatment, 6(1), 1a. See also: Puviani, L., & Rama, S. (2016). Placebo response is driven by UCS revaluation: evidence, neurophysiological consequences and a quantitative model. Scientific reports, 6, 28991.). In the above mentioned example, the active dose is administered both in the open and in the hidden case, but in the open drug administration (particularly if previous open drug administrations have occurred before), the apparent dose is greater than the delivered dose; more specifically, the apparent dose can be decomposed in two main parts: 1) the active dose and 2) an abstract (dubby) further dose which takes into account the reactive contributions which are due to: conscious placebo effects, unconscious placebo effects, previous learning and interactions with the administered substance, classical conditioning, expectations, and others phenomena. Moreover, such reactive contributions may be experienced by the user if a dose of "a given substance without the active ingredients" (e.g., without nicotine), but with the same flavors, odors, consistency, etc. of the original substance, is "openly" vaporized or delivered/administered to the user. Thus, it follows another equivalent definition for the "apparent dose" perceived during an administration: it is the active dose, or the amount of a given drug, which should be administered in an hidden mode, in order to obtain the same effects which are observed (or perceived by the user) in an open administration. (It is worth noting that the term "apparent dose", is not present in the technical literature, since this concept has been introduced by the inventors herein for a clearer disclosure of some aspects of the invention).

The term dose difference (e.g., positive or negative dose difference) is defined herein in the context of a series of doses delivered (or to be delivered) in sequential trials (or puffs/trials), and it is defined as the difference between the delivered (or to be delivered) dose of vapor or material (including active ingredients or drugs) in a given trial, and the dose delivered in the trial immediately before, or as the difference between the dose delivered in the considered trial and a linear combination of some of the sequentially delivered or inhaled doses in the trials immediately before.

The term "positive dose difference" is defined herein as a dose difference whose value is greater than zero.

The term "negative dose difference" is defined herein as a dose difference whose value is smaller (or equal) than zero.

The term "average positive (negative) dose difference" is defined herein as the sum of the values (i.e., magnitudes) of the positive (negative) doses differences divided by the number of the considered positive (negative) doses differences.

As used herein the term "stage" refers to a sequence of a given number of successive puffs or trials (e.g., a batch of puffs or trials) for each of which a dose is computed and administered or self-administered or that has to be administered (e.g., by vaping or puffing or by others modalities). For example, a stage can comprise 12 puffs/trials, or 10 puffs/trials, or 20 puffs/trials, and so on. In certain circumstances, it can be assumed that a stage comprises the number of puffs/trials required to consume a stick of tobacco in an THS device; in such an example, the number of puffs/trials can vary for each new tobacco stick. In certain embodiments, a stage comprises a given number of administration trials of a given drug or substance.

The terms "puffing features" or "puffing topography features" or "puffing behavior features" are considered herein synonyms and they refer to the puffing characteristics, such as, but not limited to: puff flow rate, puffing duration, puffing volume, average pressure drop, the interval of time occurred between two consecutive puffs, etc.

The term "puff duration" as used herein, refers to a length of time during which a vaporization device or electronic vaporizer device is coupled to a suction mechanism. In certain embodiments, the suction mechanism is a user. In certain embodiments, the suction mechanism is an analytical smoking machine. In certain embodiments, suction is provided through a mouthpiece.

The term "puff volume" as used herein, refers to a volume leaving a vaporizer device (e.g. standard reference vaporizer device, test vaporizer device, electronic vaporizer device, or vaporization device.). The volume can comprise one or more gas, solid, and/or liquid species. The puff volume can comprise an amount in ml (or cc) of air or aerosol drawn through a device, for example, either an analytical smoke machine or an electronic vaporizer device.

The term "puff flow rate" or "puffing flow rate" or "flow rate" as used herein, refers to a volume leaving a vaporizer device per unit of time. The volume can comprise one or more gas, solid, and/or liquid species. The puff flow rate can comprise an amount in ml/sec (or cc/sec) of air or aerosol drawn through a device per second, for example, either an analytical smoke machine or an electronic vaporizer device.

The term "puff frequency" as used herein refers to a number of puffs in a certain time period. In certain embodiments, the puff frequency is calculated using a mean number of puffs per a unit of time that is milliseconds, seconds, minutes or hours. In certain embodiments, the puff frequency is calculated using 1, 2, 3, 4, 5, 6, 7, 8, 9, or 10 consecutive puffs. In certain embodiments, the puff frequency is calculated using 10, 20, 30, 40, 50, 60, 70, 80, 90, or 100 consecutive puffs. In certain embodiments, the puff frequency is 1 puff every 1 second. In certain embodiments, the puff frequency is 1 puff about every 2 seconds. In certain embodiments, the puff frequency is 1 puff about every 3 seconds. In certain embodiments, the puff frequency is 1 puff about every 4 seconds. In certain embodiments, the puff frequency is 1 puff about every 5 seconds. In certain embodiments, the puff frequency is 1 puff about every 6 seconds. In certain embodiments, the puff frequency is 1 puff about every 7 seconds. In certain embodiments, the puff frequency is 1 puff about every 8 seconds. In certain embodiments, the puff frequency is 1 puff about every 9 seconds. In certain embodiments, the puff frequency is 1 puff every 10 seconds. In certain embodiments, the puff frequency is 1 puff about every 15 seconds. In certain embodiments, the puff frequency is 1 puff about every 20 seconds. In certain embodiments, the puff frequency is 1 puff about every 25 seconds. In certain embodiments, the puff frequency is 1 puff about every 30 seconds. In certain embodiments, the puff frequency is 1 puff about every 35 seconds. In certain embodiments, the puff frequency is 1 puff about every 40 seconds. In certain embodiments, the puff frequency is 1 puff about every 45 seconds. In certain embodiments, the puff frequency is 1 puff about every 50 seconds. In certain embodiments, the puff frequency is 1 puff about every 55 seconds. In certain embodiments, the puff frequency is 1 puff about every 60 seconds.

The term "total particulate matter" (TPM), as used herein, refers to an amount of matter removed from an organic material by evaporation, vaporization or aerosolization by puffing on vaporizer or electronic vaporizer device; and as used herein, can be synonymous to the phrase "mass vaporized", or "mass" aerosolized", or "$m_{vap}$" or "evaporated mass" or "$\Delta m_{cum}$".

The term "analytical smoking machine", as used herein refers to a tool that can puff on a cigarette or vaporizer device with a specified and controlled puff volume and duration.

The term "vaporizable material", as used herein, refers to a formulation of material, including in particular an organic material or botanical that is placed in a vaporization device, electronic vaporizer device, or pod (or a proprietary container) that houses the formulation. The vaporizable material can be a liquid, oil, or wax. In certain embodiments, the vaporizable material is a loose-leaf substance. In certain embodiments, the vaporizable material can contain medicinal properties that ameliorate symptoms of a medical condition. In certain embodiments, the vaporizable material can contain a recreational drug.

As used herein, the term "vapor" refers to the output of a vaporizer device, including a chemical compound or mixture of chemical compounds in the gas phase or as an aerosol.

The term "memory unit", as used herein, refers to a non-transitory computer readable medium, software or algorithm for data storage. In certain embodiments, a memory unit is a solid-state device. In certain embodiments, a memory unit is internal to the device. In certain embodiments, a memory unit stores data in random access memory (RAM). In certain embodiments, a memory unit is a hard disk, tape drive, or other external device. In certain embodiments, a memory unit refers to a device configured as a permanent holding place for digital data, until purposely erased. A memory unit also refers to devices configured as non-volatile memory chips such as flash, Read-Only memory (ROM) and/or Electrically Erasable Programmable Read-Only Memory (EEPROM).

The term "adjusting", as used herein, may refer to choosing a pod, choosing an operating parameter, choosing a type of a vaporizable material, choosing a dosage in an amount of TPM, an amount of an active ingredient, or a percentage, ratio or fraction of TPM or an active ingredient, and/or may refer to calibrating the apparatus.

The term "nicotine" as used herein refers to nicotine, nicotine salts of organic acid, and common nicotine derivatives such as; norcotinine, nornicotine, nicotine N-oxide, cotinine N-oxide, 3-hydroxycotinine and 5-hydroxycotinine.

The term "cannabinoid" refers to plant based or synthetic chemical compounds capable of acting on cannabinoid receptors and inducing a biological effect. Cannabinoids include acids, salts, and bioactive stereo isomers.

The term "*Cannabis*" refers to plants of the genus *Cannabis* and loose-leaf products or extracts thereof.

The term "tobacco" refers to plants or loose-leaf products or sticks or pods of tobacco.

In some embodiments, described herein are methods for computing and delivering successive and sequential amounts or doses of substance (including active ingredients, drugs, and substances) in a deterministic or random or pseudo-random order, to a user from a reservoir in the electronic medicament delivery device. In some variations, the electronic medicament delivery device comprises: a power source, a dose computation unit, an electronic dispenser controller, a release mechanism (e.g., a valve), a medicament reservoir, (optionally) a dispenser sensor. A method for computing and delivering or dispensing may include: (optionally) a dispenser sensor (for example a flow meter, or a position sensor, etc.) measuring a physical quantity related to the quantity of substance released during the delivering of a dose (e.g., the position of a release valve stem), the dispenser controller controlling a release mechanism (e.g., a valve) in order to precisely control the quantity of medicament to be delivered, the release mechanism (e.g., a release valve) releasing a computed dose of material from the medicament reservoir, the dose computation unit calculating the dose(s) to be delivered in the next trial(s).

As will be apparent when described in greater detail below, the dispenser sensor is not necessary. For example, the dispenser sensor may not be necessary if a calibrated dispenser mechanism is adopted in the electronic delivery device (for example if a calibrated valve in which a relationship or a look up table between the opening time and the volume of material released by the valve is employed, then the dispenser sensor is not necessary); moreover, in this last mentioned embodiment, the dispenser controller may control the calibrated dispenser mechanism (e.g., an electronic controlled release valve) to release a computed dose of material (including active ingredients, drugs, etc.).

In some embodiments, described herein are methods for computing, delivering and controlling successive and sequential amounts or doses of vapor (including active ingredients, drugs, and substances) in a deterministic or random or pseudo-random order, to a user from a vaporizable material in an electronic vaporizer device. In some variations, the electronic vaporizer device comprises: a puff sensor, a power source, a heater, a heating element controller, a temperature sensor, a dose computation unit, a puff duration predictor unit, a dose delivery unit. A method for computing and delivering may include: a puff sensor detecting a user's puff and measuring the puff flow rate and eventually some puffing topography features (for example the puff duration, the pressure drop, etc.); the heating element controller controlling an amount of power delivered from the power source during the user's puff; the temperature sensor measuring a temperature or a temperature profile generated by the heating element during the user's puff; the dose computation unit calculating the doses to be delivered in the next puff(s); the puff duration predictor unit calculating/predicting the next puff duration based on the features of the previous puffs and based on the related delivered doses; the dose delivery unit calculating the power profile to be applied to the heater through the heater controller in order to vaporize the computed dose for a given puff; moreover, the dose delivery unit may calculate the amount of the vapor delivered to the user from the vaporizable material as described herein.

In addition, the methods described may be considered generally discrete, in that the delivering, controlling and estimating of vapor dose is performed at discrete intervals forming partial doses that may later be added up to form the overall dose delivered. This configuration may, in part, allow these methods and apparatuses to function with surprising accuracy despite highly variable puffing durations and profiles.

Also provided herein are electronic medicament delivery devices configured to compute, deliver and control successive and sequential amounts or doses of material (including active ingredients, drugs, substances, etc.) in a deterministic or random or pseudo-random order, to a user from a medicament reservoir in the electronic medicament delivery device, wherein the electronic medicament delivery device may comprise any of: (optionally) a dispenser sensor (for example a flow meter, or a valve stem position sensor, etc.) configured to measure a physical quantity related to the quantity of substance released during the delivering of a dose (e.g., the position of a release valve stem), a dispenser controller configured to control a release mechanism (e.g., a valve) in order to precisely control the quantity of medicament to be delivered, a release mechanism (e.g., a release valve) configured to release a computed dose of material from the medicament reservoir, a dose computation unit configured to calculate the dose(s) to be delivered in the next trial(s).

Also provided herein are electronic vaporizers configured to compute, deliver and quantify successive and sequential amounts or doses of vapor (including active ingredients, drugs, and substances) in a deterministic or random or pseudo-random order, to a user from a vaporizable material in the electronic vaporizer device, wherein the electronic vaporizer device may comprise any of: a puff sensor configured to detect a user's puff and to measure the puff flow rate and, optionally, other puffing topography features (for example the puff duration, the pressure drop, etc.); an heating element controller configures to measure and control an amount of power delivered from the power source during the user's puff; a temperature sensor (which may be a direct sensor such as a thermistor, or it may be a temperature sensing unit that determines the temperature, e.g., of the heater, based on electrical properties of the heater) configured to determine a temperature or a temperature profile generated by a heating element during the user's puff; a dose computer (also referred to as a dose computation unit or circuitry) that calculates the doses to be delivered in the next puff(s); a puff duration predictor (also referred to as a puff duration predictor unit or circuitry) that calculates/predicts the puff duration of the next/incoming puff, based on the features of the previous puffs and on the related delivered doses; a vapor doser (also referred to as a dose delivery unit or circuitry) that calculates the power profile to be applied to the heater through the heater controller in order to release the computed dose of vapor for a given (estimated) puff duration; the dose delivery unit may also calculate/estimate the amount of the vapor delivered to the user from the vaporizable material based upon the number of time intervals involved during the puff, or, in some variants, based upon the power applied to the heater and the temperature of the heater (which may be an estimate of the temperature of the vaporizable material as it is vaporized) and the puff flow rate during a user's puff.

FIG. 1 is a schematic illustration of one example of an electronic vaporization device 100 including: a puff duration predictor unit 121, a dose computation unit 131, a dose delivery unit 109. In general, any of the vaporizer apparatuses described herein may include a heater controller 106, a heater 105, a source of vaporizable material 103, a power source (e.g., battery, not shown), a puff duration predictor unit 121, a dose computation unit 131, a dose delivery unit 109 and a puff sensor 141. The puff duration predictor unit 121 may include a clock 122 and/or a memory (memory unit) 123, or these elements may be part of an overall circuitry including a processor 110 which communicates with the puff duration predictor unit. The dose computation unit 131 may include a memory (memory unit) 133, or this element may be part of an overall circuitry including a processor 110 which communicates with the dose computation unit. The dose delivery unit 109 may include a clock 111 and/or a memory (memory unit) 113, or these elements may be part of an overall circuitry including a processor 110 which communicates with the dose delivery unit.

The heater may be any appropriate heater, including resistive heaters such as a resistive coil. The heater is typically coupled to the heater controller so that the heater controller applies power (e.g., from the power source) to the heater. The heater controller may include regulatory control logic or system to regulate the temperature and/or the power of the heater by adjusting the applied power. The heater controller may include a dedicated or general-purpose processor, circuitry, or the like and is generally connected to the power source and may receive input from the power source to regulate the applied power to the heater and it may receive input from the dose delivery unit to obtain instructions about the power values to be applied to the heater. The controller forming or including the heater controller may also include additional controllers/processors and executing logic 110, such as the puff duration predictor unit, the dose computation unit, the dose delivery unit, and/or temperature detector/sensor 107, or these components may be separate.

The puff sensor may be any sensor which can detect airflow indicative of a user taking a puff. The sensor may be an electro-mechanical device. Alternatively, the sensor may be any of a mechanical device, an optical device, an electrical device, an optomechanical device, a micro electro mechanical systems (MEMS) based sensor and an acoustic sensor.

Any source of vaporizable material may be used, including a reservoir (e.g., well, pod, cartridge, or the like), which includes the material to be vaporized. The material to be vaporized may include a carrier and one or more active ingredients. The material to be vaporized may be a tobacco stick, or a loose-leaf material, or botanicals.

In some embodiments, the dose computation unit is configured to compute the doses to be delivered in the next puffs/trials at groups or sequences of a given number of doses (or puff/doses), also named batch of doses herein. Each of the sequences of doses that have to be computed by the dose computation unit are also termed "stage" herein. For example, a stage can include 12 doses to be computed and delivered, or a stage can include 10 doses, etc. In certain embodiments a stage can include only one dose. The dose computation unit generally bases the calculation on input from the dose delivery unit. The dose computation unit may then use the acquired information about the previous(s) delivered dose(s) (i.e., the dose(s) delivered in the previous puff(s)/trial(s)) together with some settable or predetermined parameters (e.g., a predetermined average cumulative dose to be administered or vaporized, the minimum and the maximum values that a dose can assume, and others, as will be described in greater detail below) for computing a sequence of successive doses (or of a single dose) to be delivered in the next puff(s)/trial(s) and their order within the sequence, as will be described in greater detail below.

In general, the puff duration predictor unit is configured to divide up a time period (e.g., during a single puff) into a plurality of sequential time intervals, which may be referred to as partial dose intervals or time intervals, and determine the puffing topography features analyzing the puffing characteristics at each time interval. For example, the average puff flow rate (which may represent a puffing feature) may be estimated by the puff duration predictor unit by storing the puff flow rate at each time interval (from the puff sensor) and/or make computations at each time interval, for example computing the average flow rate incrementally at every time interval; in some embodiments, the clock/timer of the puff duration predictor unit is adopted for the estimation of the puff duration, and for the estimation of the time intervals between successive puffs. In certain embodiments, the puff duration or the time intervals between successive puffs may be expressed and stored as a number of partial dose intervals. For example, the time duration of a puff of about 2500 ms may be measured as 50 partial dose time intervals (or time intervals), provided that the time interval is 50 ms (or, equivalently, that the sampling rate is 20 Hz). Thus, the device, including the puff duration predictor unit may include a timer or clock 122 and can generate intervals of any appropriate duration within a time period (e.g., between 10 msec and 200 msec). Thus, the puff duration predictor unit may sample at a frequency related to the duration of the time intervals (e.g., between 5 Hz and 100 Hz, etc., between 5 Hz and 120 Hz, between 5 Hz and 140 Hz, between 5 Hz and 150 Hz, between 5 HZ and 180 Hz, between 5 HZ and 200 Hz, between 5 HZ and 300 Hz, etc.). The puff duration predictor unit generally bases the calculation on input from the puff sensor and from the dose delivery unit, and (optionally) from the dose computation unit. The puff duration predictor unit may then use the acquired information about the previous puffs (e.g., the puff duration, the time interval between successive puffs, the average flow rate of a puff, the pressure drop, etc.) together with the related delivered doses (which may be transmitted from the dose delivery unit to the puff duration predictor unit) and (optionally) with the dose to be delivered in the next/incoming puff (transmitted from the dose computation unit), for predicting the next/incoming puff duration, as will be described in greater detail below.

In general, the dose delivery unit is configured to divide up a time period (e.g., during a single puff) into a plurality of sequential time intervals, which may be referred to as partial dose intervals or time intervals, and calculate for each of the sequential time intervals the power that the heater controller has to apply to the heater. Thus, the device, including the dose delivery unit may include a timer or clock 111 and can generate intervals of any appropriate duration within a time period (e.g., between 10 msec and 200 m sec). The dose delivery unit generally bases the calculation of the power to be applied to the heater at each time intervals, on: a) a temperature of the vaporizable material being vaporized immediately before the actual partial dose time interval; b) input from the puff duration predictor unit, which may include the predicted puff duration for the next or incoming puff, during which a computed dose has to be delivered; c) input from the dose computation unit, which may include the dose(s) to be delivered in the next/incoming puff(s); d) input from the puff sensor, which may include the beginning of a puff in which the actual dose has to be delivered and the flow rate occurred immediately before the actual partial dose time interval. In some variants, the flow rate occurred immediately before the actual partial dose time interval may be transmitted from the puff duration predictor unit to the dose delivery unit. The dose delivery unit may then use the abovementioned information to calculate the power to be delivered to the heater for vaporizing the vaporizable material during a time interval, as will be described in greater detail below.

Moreover, the dose delivery unit is configured to determine the partial dose (or mass) of vapor produced during each partial dose interval. The dose delivery unit may then sum these up to determine the actual dose produced and presumably delivered to the user in a given puff. The dose delivery unit may base the calculation of each partial dose on input from the dose computation unit, on input from the puff duration predictor unit and on input from the puff sensor, as will be described in great details hereinafter. Alternatively, the dose delivery unit may base the calculation of each partial dose on input from the puff sensor, which may include the flow rate measured before or at the start of each partial dose interval. The dose delivery unit also receives an input proportional to the temperature at the start of each partial dose interval (e.g., the temperature or a value proportional to the temperature at the end of the immediately previous partial dose interval). The dose delivery unit may receive also the power delivered to the heater during the partial time interval from the heater controller. The dose delivery unit may then use the power, temperature and flow rate information to calculate the dose (e.g., mass) of vapor during that interval, as will be described in greater detail below. These interval values (dose interval values) may be summed over the entire time period (e.g., the actual puff duration) to determine the overall dose of vapor generated; the dose delivery unit may also then convert this dose of vapor to a dose of an active ingredient in the vapor, by, e.g., converting based on the concentration of active ingredient in the vaporizable material.

As mentioned above, in some variations the temperatures for the vaporizable material being vaporized by the device are determined from the heater, without requiring an additional sensor. For example, the relative change in resistance of the heater (e.g., the temperature coefficient of resistivity) may be used, along with a reference resistor, to approximate the temperature of the heater. Although a conversation factor may be used to convert the ratio of heater resistivity and reference resistivity to an actual temperature value, in some variations the system, and particularly the dose delivery unit, may use the proportional value directly, without multiplying by a conversion factor. These values are therefore "proportional" to the temperature. For example, any of these apparatuses may include logic for determining the temperature of the heater based on the TCR.

The resistance of the heater (e.g., a resistive heater) may be measured ($R_{heater}$) during operation of the apparatus as well as the resistance of a reference ($R_{reference}$) resistor separate from the heater. The ratio of the heater resistance to the reference resistance ($R_{heater}/R_{reference}$) is linearly proportional with the temperature (above room temp) of the heater, and may be directly converted to a calibrated temperature. For example, a change in temperature of the heater relative to room temperature may be calculated using an expression such as $(R_{heater}/R_{reference}-1)\cdot(1/TCR)$, where TCR is the temperature coefficient of resistivity for the heater. For example, TCR for a particular device heater may be 0.00015. In determining the partial doses and doses, the temperature value used (e.g., the temperature of the vaporizable material during a dose interval, $T_i$, described in more detail below) may refer to the unitless resistive ratio (e.g., $R_{heater}/R_{reference}$) or it may refer to the normalized/corrected temperature (e.g., in ° C.).

Thus, the dose delivery unit may be configured to determine the power to be delivered by the heater controller to the heater for vaporize a (computed) dose of material, based upon a flow rate measured before each of the partial dose time intervals which form the time period or the puff duration, and a temperature of the vaporizable material being vaporized before each partial dose time interval. As just mentioned, the temperature of the vaporizable material being vaporized may refer to an input that is proportional to the temperature. The dose delivery unit may also be configured to determine a dose of vapor delivered to a user during a time period based upon the actual total number of time intervals during each of which a partial dose has been vaporized (in other words, the dose delivery unit may estimate the delivered dose within a puff, by summing up the computed and delivered partial doses during each of the time interval within a puff duration, as will be described in greater detail below); or the dose delivery unit may also be configured to determine a dose of vapor delivered to an user based upon an amount of power delivered by the heater controller to the heater to vaporize the vaporizable material during each of a plurality of partial dose time intervals within the time period, a temperature of the vaporizable material being vaporized before each partial dose time interval, and a flow rate measured before each partial dose time interval.

Figure 2:
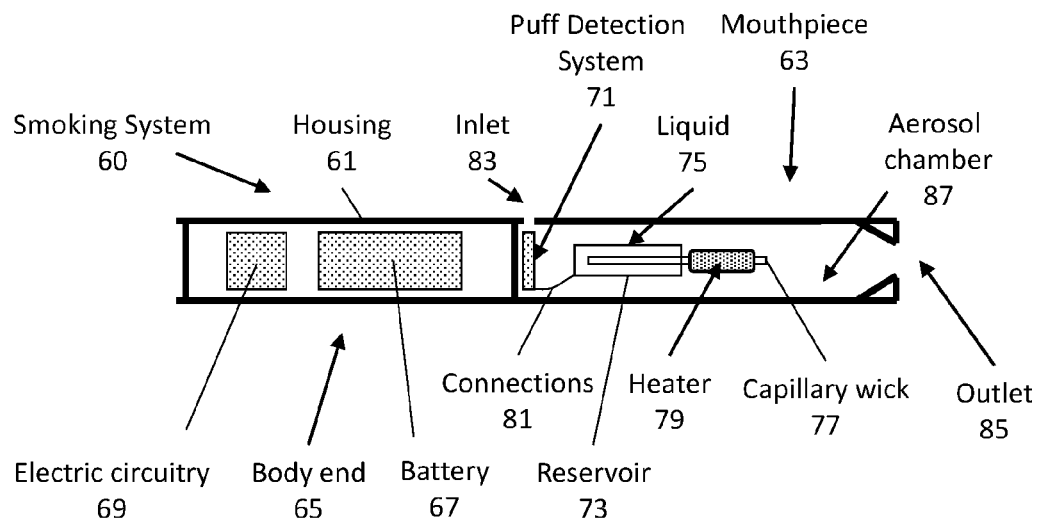
FIG. 2 shows one example of an electrically heated aerosol generating system.

FIG. 2 shows one example of an electrically heated aerosol generating system or electronic vaporizer or medical inhaler or an inhalation device, for generating an inhalable aerosol. In FIG. 2, the system is a smoking system having a liquid storage portion or reservoir. The smoking system 60 of FIG. 2 comprises a housing 61 having a first end which is the mouthpiece end 63 and a second end which is the body end 65.

In the body end, there is provided an electric power supply in the form of battery 67, such as a rechargeable battery, and electric circuitry in the form of hardware 69, such as a printed circuit board (PCB) containing a microcontroller with the operating logic and software instructions for the device, and a puff sensor or puff detection system 71. In the mouthpiece end, there is provided a liquid storage portion in the form of cartridge (or tank or reservoir) 73 containing liquid 75, a capillary wick 77 and a heater 79 comprising at least one heating element. Note that the heater is only shown schematically in FIG. 2. In this example, the heater 79 may be used as a temperature sensor as described above and herein, e.g., using the temperature coefficient of resistance (TCR) and a reference resistance. Alternatively, or additionally, a separate temperature sensor (e.g., thermistor, etc.) that is in thermal contact with the heater and/or vaporizable material may be used. The temperature sensor may, in general, be configured to measure a temperature of a vaporizable material within the heater 79. The temperature of the heater may be controlled by the microcontroller of the PCB 69.

One end of the capillary wick 77 extends into the cartridge 73 and the other end of the capillary wick 77 is surrounded by the heater 79. The heater is connected to the electric circuitry via connections 81. The housing 61 also includes an air inlet 83, an air outlet 85 at the mouthpiece end and an aerosol-forming chamber 87. In use, operation is as follows. Liquid 75 is transferred or conveyed by capillary action from the cartridge 73 from the end of the wick 77 which extends into the cartridge to the other end of the wick 77 which is surrounded by the heater 79. When a user draws on the device at the air outlet 85, ambient air is drawn through air inlet 83. In the arrangement shown in FIG. 2, the puff detection system 71 senses the puff and activates the heater 79. The battery 67 supplies energy to the heater 79 to heat the end of the wick 77 surrounded by the heater. The liquid in that end of the wick 77 is vaporized by the heater 79 to create a super saturated vapor. At the same time, the liquid being vaporized is replaced by further liquid moving along the wick 77 by capillary action. (This is sometimes referred to as "pumping action".) The supersaturated vapor created is mixed with and carried in the airflow from the air inlet 83. In the aerosol-forming chamber 87, the vapor condenses to form an inhalable aerosol, which is carried towards the outlet 85 and into the mouth of the user.

The capillary wick can be made from a variety of porous or capillary materials and preferably has a known, pre-defined capillarity. Examples include ceramic- or graphite-based materials in the form of fibres or sintered powders. Wicks of different porosities can be used to accommodate different liquid physical properties such as density, viscosity, surface tension and vapor pressure. The wick must be suitable so that the required amount of liquid can be delivered to the heating element. The wick and heating element must be suitable so that the required amount of aerosol can be conveyed to the user.

In the embodiment shown in FIG. 2, the hardware 69 and the puff detection system 71 are preferably programmable. The hardware 69 can be used to manage the device operation. This assists with control of the particle size in the aerosol and for the doses computation, doses control and doses delivery.

The device 60 (or any other vaporizable device) can include on-board processing configured to determine an amount of material vaporized and delivered to the user, to predict the puff duration of the next (actual) puff(s), to compute and deliver sequences of successive doses (e.g., amount of vapor, or drug or active ingredients, etc.) over sequential puffs.

FIG. 2 shows one example of an electrically heated aerosol generating system which may be used with the present invention. Many other examples are usable with the invention, however. For example, electronic Tobacco Heating System (THS) devices can be usable with the invention. In general, the electrically heated aerosol generating system simply needs to include or receive an aerosol forming substrate which can be heated by at least one electric heating element, powered by a power supply under the control of electric circuitry. For example, the system need not be a smoking system. For example, the aerosol forming substrate may be a solid substrate, rather than a liquid substrate. Alternatively, the aerosol forming substrate may be another form of substrate such as a gas substrate. The heating element may take any appropriate form. The overall shape and size of the housing could be altered and the housing could comprise a separable shell and mouthpiece. Other variations are, of course, possible.

Figure 3:
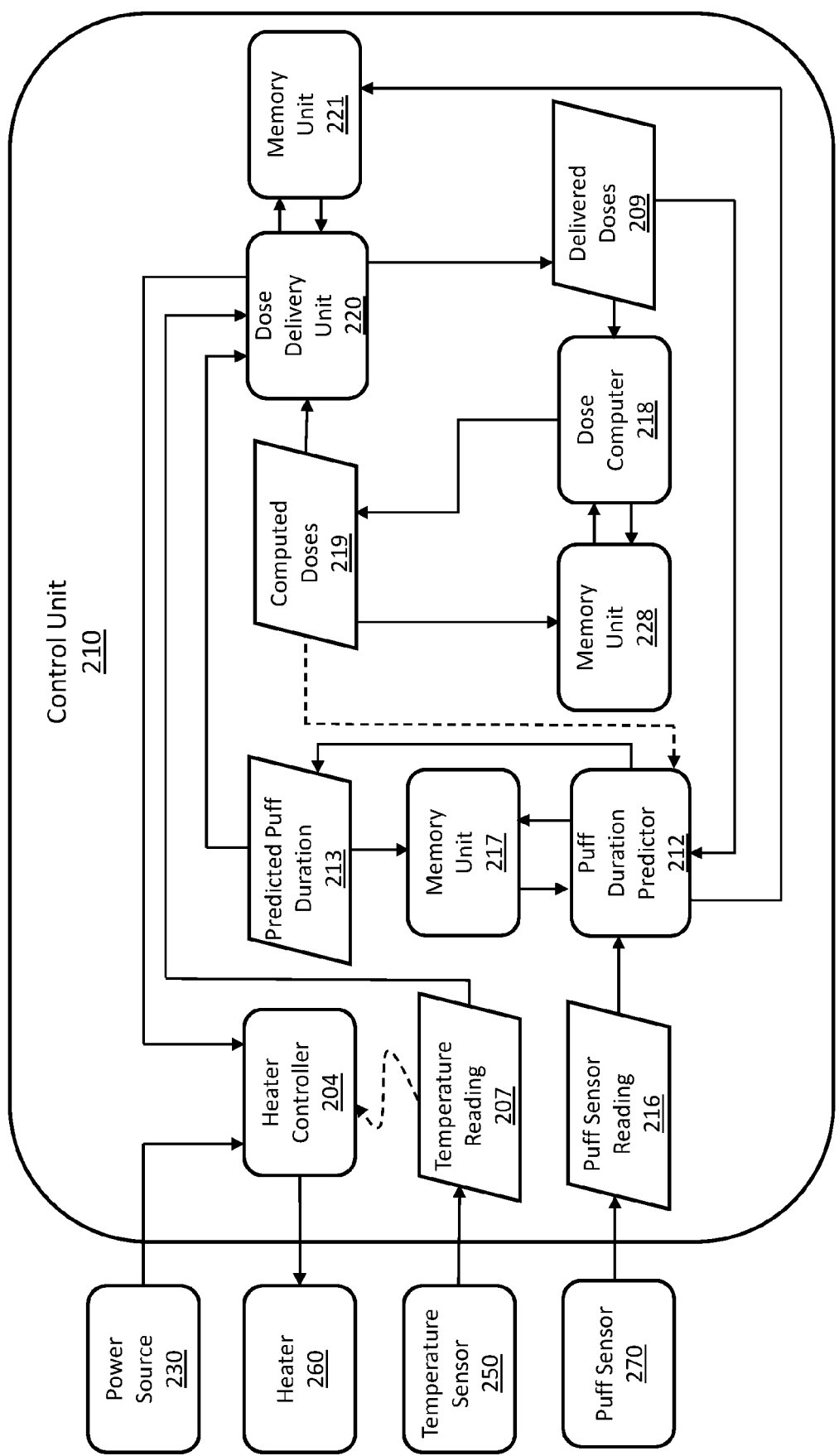
FIG. 3 is an example of an exemplary apparatus able to increase the physiological effects produced by active ingredients (or material, or drug, or substance) vaporized by the device, as described herein.

FIG. 3 shows a flowchart that represents another exemplary vaporizer apparatus capable of computing and delivering a sequence of successive doses within the apparatus (device 60) comprising: a) computing a sequence of doses to deliver in the next puffs/trials; b) predicting the puff duration of the next puff(s); c) computing the power profile to apply to the heater for delivering the computed doses during each of the sequential time intervals within a time period (e.g., a puff duration); d) determining the amount of material vaporized within the apparatus. As shown, the power source 230, heater 260, temperature sensor 250, and puff sensor 270 are communicatively coupled to a control unit 210 (which can be part of one or more printed circuit board(s) 69 shown in FIG. 2).

The control unit 210 can include a heating element controller 204, a puff duration predictor (or puff duration predictor unit, which may be a type of puff duration predictor unit) 212 and a related memory unit 217, a dose computer (or dose computation unit, which may be a type of dose computation unit) 218 and a related memory unit 228, a vapor doser (or dose delivery unit, which may be a type of dose delivery unit) 220 and a related memory unit 221.

To compute a dose or a sequence of successive doses (e.g., a stage of doses involving a given number or batch of doses in sequence) to deliver to a user, the dose computation unit 218 can base the computations on the input from a computed or estimated vaporized mass 209 and on the input from the memory unit 228, so that the dose computation unit 218 can calculate a (or some) dose(s) to be delivered, named herein "computed doses to be delivered" 219. In certain embodiments the dose computation unit relays the computed vaporized mass(es) 209 and/or some computational processing of it to the memory unit 228 (in this way, for example, the last delivered dose or a series of actually delivered doses can be stored and processed by the dose computation unit 218). In certain embodiments, the dose computation unit 218 relays the computed doses to be delivered 219 to the memory unit 228, and/or to the dose delivery unit 220.

To predict the duration of a given puff (e.g., the puff duration of the next puff), the control unit 210 can relay a puff sensor reading 216 to the puff duration predictor unit 212, which also on the basis of the input from the computed or predicted vaporized mass 209 and/or also on the basis of the input from the memory unit 217 can calculate/predict the duration of the next puff, named herein "predicted puff duration" 213. In certain embodiments, the puff duration predictor unit 212 relays the predicted puff duration 213 to the memory unit 217, and/or to the dose delivery unit 220. In certain embodiments the puff duration predictor unit 212 relays the puff sensor reading and/or the results of some of their computational processing (e.g., features extraction or estimation performed in the puff duration predictor unit) to the memory unit 217.

To deliver a dose of vapor or material to a user, the control unit 210 can relay the temperature reading 207 and the puff sensor reading 216 during a puff to the dose delivery unit 220, which also on the basis of the input from the computed doses to be delivered 219 and also on the basis of the input from the predicted puff duration 213 and on the basis of the input from the memory unit 221 can calculate/predict the power values to be delivered at each sequential time intervals within the duration of a puff or of a time period, and control the heater controller 204 to apply the computed power values to the heater 260, as will be described in great detail hereinafter.

To determine an amount of vapor received by the user, the control unit 210 can relay the puff sensor reading 216 during a puff to the dose delivery unit 220, which can calculate a predicted vaporized mass 209, as will be described in great detail hereinafter.

In some variants, to determine an amount of vapor received by the user, the control unit 210 can relay a temperature reading 207 and the puff sensor reading 216 during a puff (which can be determined by the puff sensor 270) to the dose delivery unit 220, which can calculate a predicted vaporized mass 209. In certain embodiments, the dose delivery unit 220 relays the predicted vaporized mass 209 to the memory unit 221. In certain embodiments, the dose delivery unit 220 relays the computed/predicted vaporized mass 209 to the dose computation unit 218 and to the puff duration predictor unit 212.

Computation of the Doses to be Delivered in a Sequential Order in Successive Puffs/Trials Without desired to be bound by the theory, it is believed that the user's experience (including satisfaction, product or treatment acceptance, rewarding effects, psychological rewarding, neurophysiological effects at the level of the central nervous system) is affected by the perceived features and effects (even implicitly and in part unconsciously) relative to the inhaled active substance. In fact, the inventors have unexpectedly identified methods for modulating (e.g., increasing) such perception and the related effects by means the delivery of sequential varying doses of drug or vapor for each of the sequential puffs/trials, as disclosed herein. In particular, each puff determines a compounds of psychological and physiological effects, such that the overall effect due to a given puff is determined by both active and reactive contributions. Active contributions are represented by the effects determined by the neurophysiological active ingredients (e.g., nicotine effects at the central nervous system), while reactive contributions are represented by conditioned responses and reinforced cues (e.g., chemosensory features, flavors, conditioned reward effects, etc.) and some of the same active effects which have been conditioned (this phenomenon is termed "mimicking" or "pharmacological mimicking", e.g., see: Placebo response is driven by ucs revaluation: evidence, neurophysiological consequences and a quantitative model. Scientific reports, 6, 28991). The methods and apparatuses disclosed herein may be able to enhance the reactive contributions: such an enhancement may be due to a process of unconditioned stimulus (UCS) inflation (i.e., enhancement, or increase), determined by a continuous and dynamical stimulus revaluation which is driven by weighted prediction errors within the central nervous system. The computation of a prediction error may occur unconsciously and implicitly within the central nervous system, and it is based on the difference of the effects expected by a given stimulus (or previously experienced) and the effects actually perceived or experienced or determined. Moreover, the weight of a prediction error within the central nervous system, represents (at least in part) the neural gain which is assigned to the prediction error before it can update the reactive response associated to the neural representation of a given stimulus.

Such a weight depends on different features, such as the environment uncertainty, the uncertainty of the expected effects, the uncertainty of the experienced effects, the magnitude of the stimulus, the magnitude of the effects determined by a given stimulus, the contrast effects, the magnitude of the prediction error itself, and others. Provided that all the variables except the magnitude (or the intensity) of the stimulation, are deemed constant, the modulation of the magnitude of the stimulation (or its effects) does permit to modulate the weights of the prediction errors, for instance, enhancing the positive weighted prediction errors while reducing the negative weighted prediction errors, over successive sequential trials. In such a way, the reactive contributions of the effects produced by the given stimulus can be enhanced cumulatively (as it has been unexpectedly identified by the inventors, see: Puviani, L., & Rama, S. Understanding and exploiting prediction errors minimization within the brain in pharmacological treatments. Behavioural brain research (Volume 359, 1 Feb. 2019, pages 223-233)).

The methods and apparatuses disclosed herein, in some embodiments, may compute the sequential partial doses to be delivered on each of the sequential puff/trial in a random or in a pseudo-random way, so that the environment uncertainty can be considered constant over time. Furthermore, the methods disclosed herein, in certain embodiments, compute and deliver sequences of doses such that the average positive dose difference is greater than the average negative dose difference, whereby the weights associated to positive prediction errors within the central nervous system are greater than the weights associated with the negative prediction errors, so that a UCS inflation (or increment) may take place over successive puffs/trials. Thus, in certain embodiments, the dose computation unit (131) and the dose delivery unit (109) constitute a means for increasing the neurophysiological or physiological effects associated to a given substance (e.g., a vaporizable substance or ingredients). In certain embodiments, the dose delivery unit (109), the dose computation unit (131), and the puff duration predictor unit (121) constitute a means for increasing the neurophysiological or physiological effects associated to a given substance. Moreover, the methods and apparatuses disclosed herein, in some embodiments, may predict the puffing features (e.g., the puff duration) of the next or incoming puff/trial, in which the computed dose has to be delivered, eventually providing at least two benefits: 1) a computed dose of vapor or material can be delivered or vaporized more effectively; 2) the user may experience an improved consistency of vapor delivery over the entire puff duration, even if the dose to be delivered has previously been computed and hence it has been pre-defined.

In a certain embodiment, the amount of vapor (or material or dose) to be delivered in a given number of successive and sequential puffs, within a vaporizing device, such as device 60, can be computed from the previous delivered dose(s) (e.g., from the last delivered dose), and from certain values and constraints set up by the producer in the factory, or by the user, or by a dynamic algorithm (in particular, the needed values and/or constraints which will be described in a greater detail hereinafter, may be set up automatically or manually, and may be set up at the factory, in some variations, the values may be set up by the user). More specifically, the doses to be delivered can be computed in batch of a given number of doses/trials, taking into account the dose(s) delivered immediately before, and the following constraints: the doses may be computed such that, starting from a given puff/trial the average positive dose difference is greater in magnitude than the average negative dose difference, subject to the constraint that the average cumulative administered or inhaled dose (i.e., the sum of the doses delivered over successive puffs/trials divided by the number of trials) is kept constant or equal to a predetermined value over time (or over successive puffs/trials) or it is reduced (or it is varied and set as desired), and subject to the constraint that each dose can take only values within a settable or predetermined range, and/or subject to the constraint that a dose difference can assume values within predetermined ranges, wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences. In certain embodiments, the average dose difference has to be greater in magnitude (i.e., the absolute values have to be compared) than the average negative dose difference of about a 5% factor. In certain embodiments, the magnitude of the average dose difference has to be greater than the magnitude of the average negative dose difference of about a 10% factor. In certain embodiments, the magnitude of the average dose difference has to be greater than the magnitude of the average negative dose difference of about a 15% factor. In certain embodiments, the magnitude of the average dose difference has to be greater than the magnitude of the average negative dose difference of about a 20% factor. In certain embodiments, the magnitude of the average dose difference has to be greater than the magnitude of the average negative dose difference of about a 25% factor. In certain embodiments, the magnitude of the average dose difference has to be greater than the magnitude of the average negative dose difference of about a 30% factor. In certain embodiments, the magnitude of the average dose difference has to be greater than the magnitude of the average negative dose difference of about a 35% factor. In certain embodiments, the magnitude of the average dose difference has to be greater than the magnitude of the average negative dose difference of about a 40% factor. In certain embodiments, the magnitude of the average dose difference has to be greater than the magnitude of the average negative dose difference of a factor greater than a 40% (e.g., of a 50% factor, of a 200% factor, and so on).

The doses can be computed and delivered sequentially in a random or pseudo-random or in a deterministic order.

The doses may be computed in the dose computation unit, or they can be pre-computed externally and upload into a memory unit of the dose computation unit or a memory unit of the vaporizer device.

In a certain embodiment, an example of the methods of computing a batch (or a stage) of doses, may include performing the following steps (in such an embodiment, a dose difference is assumed to be the difference between a given dose and a dose delivered (or to be delivered) immediately before):

1) In a given stage with a settable or a predetermined number of puffs/trials, named ñ, for which the doses have to be computed, and given (e.g., set in the factory) two settable or predetermined values for the number of positive doses differences and for the number of negative doses differences, named $n_+$ and $n_-$, respectively, and such that $ñ=n_++n_-$ (for a non-limiting example, in a certain embodiment, $ñ=12$, $n_+=3$, $n_-=9$), initialize the sequential positions of all the ñ differences doses, for example in a random way (for example, in a certain embodiment wherein a stage involving 12 doses to be computed is considered, a randomly generated sequence of 9 negative and 3 positive doses differences, may appear as in the follows:

diff⁻, diff⁻, diff⁻, diff⁻, diff⁺, diff⁻, diff⁻, diff⁺, diff⁻, diff⁻, diff⁻, diff⁺, where each term diff⁻ represents a position of a negative dose difference and each term diff⁺ represents a position of a positive dose difference). In certain embodiments, it is preferable (without desired to be limited) setting the very first dose of a given stage to be relatively "high", for neurophysiological reasons. In this case, if the last delivered dose of the previous stage was higher than the average delivered dose (e.g., the last dose difference of the previous stage was a positive difference), then the first dose of the actual stage may be set equal to the last dose delivered in the previous stage, moreover, only the remaining ñ−1 doses differences positions have to be initialized. Conversely, if the last delivered dose in the previous stage was lower than the average delivered dose (e.g., the last dose difference of the previous stage was a negative difference), then the first position of the doses differences in the actual stage may be assigned to a positive dose difference, and the others $n_-$ negative and $n_+-1$ positive doses differences positions can be randomly assigned. Moreover, initialize a counter for the delivered doses (i.e., c=0).

2) Initialize the values of the negative doses differences, for example, in a certain embodiment, this may be accomplished by generating $n_-$ values from a gaussian distribution with a settable or predetermined mean, $\mu_-$, and a settable or predetermined variance, $\sigma_-^2$. For instance, $\mu_-$ may be set in milligrams (mg) (for example $\mu_-=-0.016$, and $\sigma_-^2=0.03$), which means that a random generated value sampled from a gaussian distribution whose mean is equal to −0.016 mg and whose variance is equal to 0.03 represents a dose decrement in mg (i.e., a negative dose difference expressed in mg). The computed/initialized negative doses may be attributed to an active substance (in mg), such as nicotine, or to a TPM.

3) Compute the positive doses differences such that the average delivered dose in the actual stage will be equal to a predetermined or settable value, named $\bar{\mu}$, (for example, $\bar{\mu}$ can be set to be equal to the average value of the doses delivered in the previous stage, named $\mu_{PREC}$, or in certain embodiments, it may be set to be equal to a predetermined fixed value, such as the desired average mg of nicotine or of TPM, or it may be set as a time-varying value). In a certain embodiment, for computing the positive doses differences, the following equation can be solved:

$$\alpha_1 \cdot \text{diff}_1^- + \alpha_2 \cdot \text{diff}_2^- + \ldots + \alpha_{n_-} \cdot \text{diff}_{n_-}^- + \beta_1 \cdot \text{diff}_1^+ + \beta_2 \cdot \text{diff}_2^+ + \ldots \beta_{n_+} \cdot \text{diff}_{n_+}^+ = (\bar{\mu} - D_{-1}) \cdot \tilde{n}$$

while imposing the following condition:

$$\text{diff}_1^+ = \text{diff}_2^+ = \ldots = \text{diff}_{n_+}^+ = \text{diff}^+,$$

where, $D_{-1}$ represents the last delivered dose in the previous stage, $\alpha_i$ ($\beta_i$) $i \in [1, n_-]$ ($i \in [1, n_+]$) represents the numerical value corresponding to the position, in a reverse order, of the i-th negative (positive) dose difference $\text{diff}_i^-$ ($\text{dif}_i^+$) within the full sequence of ñ doses differences. For instance, if $\text{diff}_1^-$ occupies the first position within the full sequence of doses differences in the considered stage, then $\alpha_1 = \tilde{n}$. Hence, each positive dose difference may be obtained computing the equation 1:

$$\text{diff}_i^+ = \frac{(\bar{\mu} - D_{-1}) \cdot \tilde{n} - (\alpha_1 \cdot \text{diff}_1^- + \alpha_2 \cdot \text{diff}_2^- + \ldots + \alpha_{n_-} \cdot \text{diff}_{n_-}^-)}{\beta_1 + \beta_2 + \ldots + \beta_{n_+}} \quad \text{equation 1}$$

4) Compute, sequentially, the ñ doses to be delivered, starting from the last delivered dose in the previous stage (named $D_{-1}$), and summing recursively the doses differences of the initialized sequence, in the actual stage. More precisely, the first dose ($D_1$) can be computed as the sum between $D_{-1}$ and the dose difference in the first position of the sequence; then, the second dose ($D_2$) can be computed as the sum between $D_1$ and the dose difference in the second position, and so on.

In practice, compute $D_i=D_{i-1}+\text{diff}_i^-$ where $D_i$ represents the dose to be deliver at the i-th trial and represents the dose delivered (or to be delivered) at the (i−1)-th trial, if the i-th dose difference within the sequence is a negative dose difference, or compute $D_i=D_{i-1}+\text{diff}_i^+$ if the i-th dose difference within the sequence is a positive dose difference.

5) If the computed doses are included within a settable or predetermined range (e.g., each dose is included within a range delimited by a minimum and a maximum set or predetermined value, min≤$D_i$≤max), then go to the next point. Conversely, if one of the computed doses in the actual stage is out of range, then perform a new initialization, restarting from point 1). For a non-limiting example, in a certain embodiment, the minimum value that a delivered dose of nicotine can take may be equal to 0.04 mg and the maximum value may be equal to 0.12 mg. Optionally, in certain embodiment, the apparatus may further check to see if each dose difference is included in predetermined ranges (one range for the positive doses differences and one range for the negative doses differences); then, if each dose difference is included within such ranges then the system can go to the next point, otherwise, the system may perform a new initialization restarting from point 1.

6) Deliver the next (i.e., c-th) computed doses in the considered stage, and increment the counter of the total number of delivered doses (i.e., c=c+1) and go to the next point.

7) If the number of delivered doses is equal to ñ, then go to point 1) for the beginning of a new computation stage; otherwise, compute the difference between the actual measured/detected delivered dose (e.g., measured or estimated by the dose delivery unit, as described in great details hereinafter) and the measured/estimated dose delivered in the puff/trial immediately before (indicated as $\text{diff}_c^{delivered}$) furthermore, perform a comparison between the "measured/estimated" dose difference ($\text{diff}_c^{delivered}$) and the corresponding computed/initialized dose difference (indicated as $\text{diff}_c^{computed}$); if the two doses differences have different signs (positive or negative), then perform a new initialization restarting from the point 1) (considering a new stage). On the contrary, if the detected dose difference and the computed dose difference are of the same type (either positive or negative), then, perform a check to see if the difference between the actual measured/detected delivered dose (termed $D_{delivered}$) and the corresponding computed dose at point 4) (termed $D_c$) is within a given/settable (and relatively small) range, for example within ±2% of the computed value $D_c$ (in some variations other range can be set, such as within ±5%, or ±6%, or ±10% etc., or within a given absolute range (e.g., within ±k, where k may assume a relatively small value, such as 0.005 mg of nicotine, or 0.001 mg or 0.01 mg and so on); in formulae the check operation may be performed by evaluating: $|D_{delivered}-D_c|\le k_1$, where $D_{delivered}$ represents the measured delivered dose, $D_c$ represents the computed dose for the considered puff/trial, and $k_1$ may be expressed in percentage of the computed dose, such as $k_1=0.05\ D_c$ (if a range of ±5% is considered), or it may be expressed as an absolute value in mg, such as $k_1=0.005$ mg (or $k_1=5$ μg) and so on). In a certain embodiment, $k_i$ may be set equal to 0.005 mg of nicotine. If the difference between the measured ($D_{delivered}$) and the computed ($D_c$) doses fall within the predetermined range, then go to point 6. On the contrary, perform a further check to see if the difference between the measured delivered dose (i.e., transmitted from the dose delivery unit to the dose computation unit) and the corresponding computed dose is comprises within a second predetermined range (wherein, such a second range is greater or coarser than the first range previously considered), for example, check if the following condition is satisfied $|D_{delivered}-D_c|\le k_2$ wherein $k_2>k_1$ (for a non-limiting example, $k_1=0.05\ D_c$ and $k_2=0.2\cdot D_c$). If the abovementioned condition is satisfied, then perform a new initialization of the remaining negative doses differences of the actual stage, and perform a new computation/initialization for the remaining positive doses differences in the actual stage (i.e., update the total number of the remaining doses differences, c, update the number of the remaining negative and positive doses differences, $n_-$ and $n_+$ and then go to point 2)). Conversely, if the difference between the measured delivered dose and the computed one is out of the preset range (i.e., $|D_{delivered}-D_c|>k_2$) then perform a new computational stage and a new initialization for all the doses differences, restarting from the point 1).

It is worth noting that a control or check operation between the computed doses (and the computed doses differences) and the actually delivered and measured doses (and doses differences) is preferred, since the actual delivered dose depends upon the puff duration, which may be predicted with a certain error in some trials or conditions.

In certain embodiments, in addition to the control about the value of each measured/estimated dose, a control for the value of the detected dose difference may be performed too. Such a control can be useful to assure that the pseudo-random computed doses differences fall within predetermined range, for a more effective enhancement of the neurophysiological reactive contributions. In some embodiments this may be not necessary.

Figure 7A:
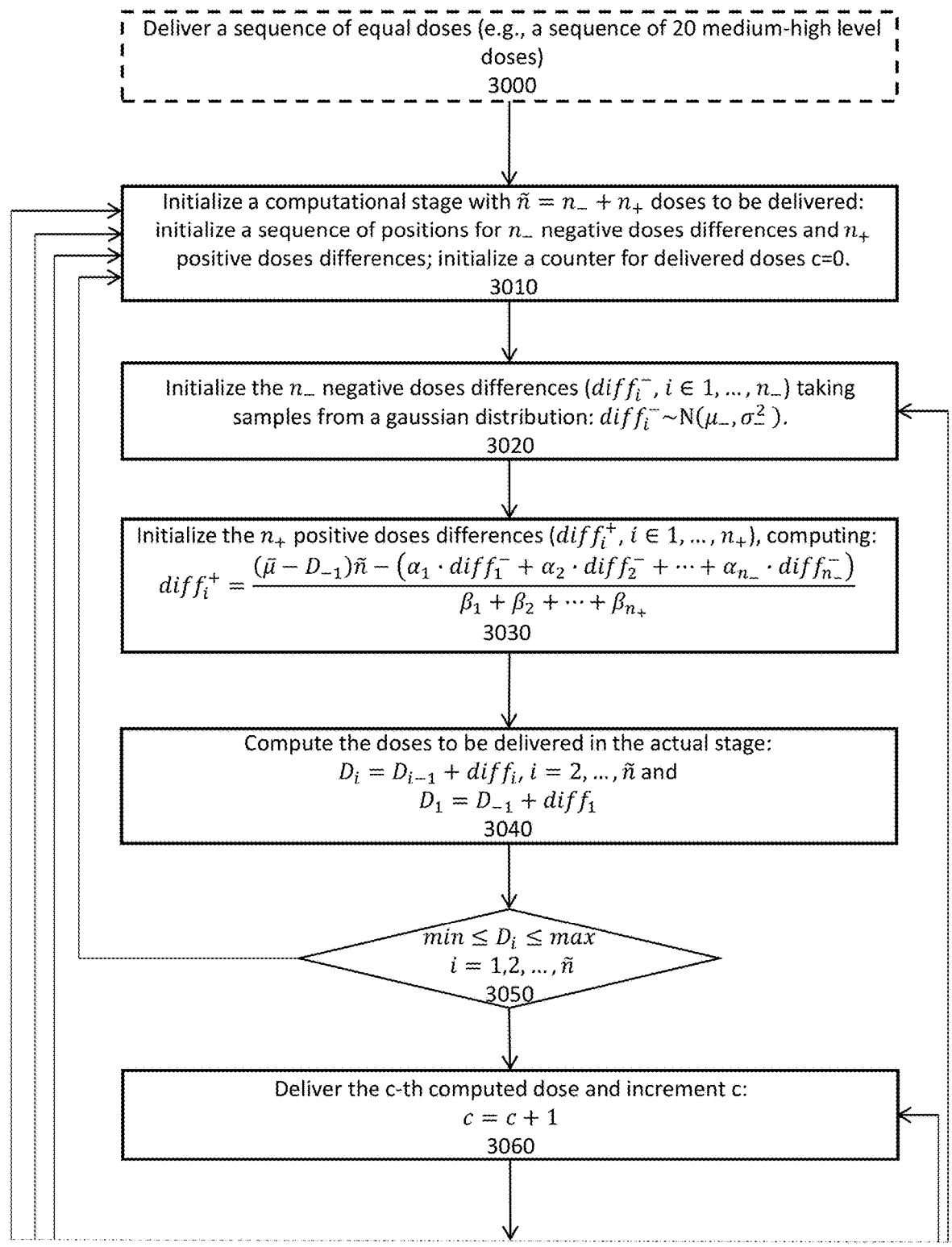
FIG. 7A-7B schematically illustrates one method of computing and controlling a sequence of successive doses to be vaporized, as described herein.
Figure 7B:
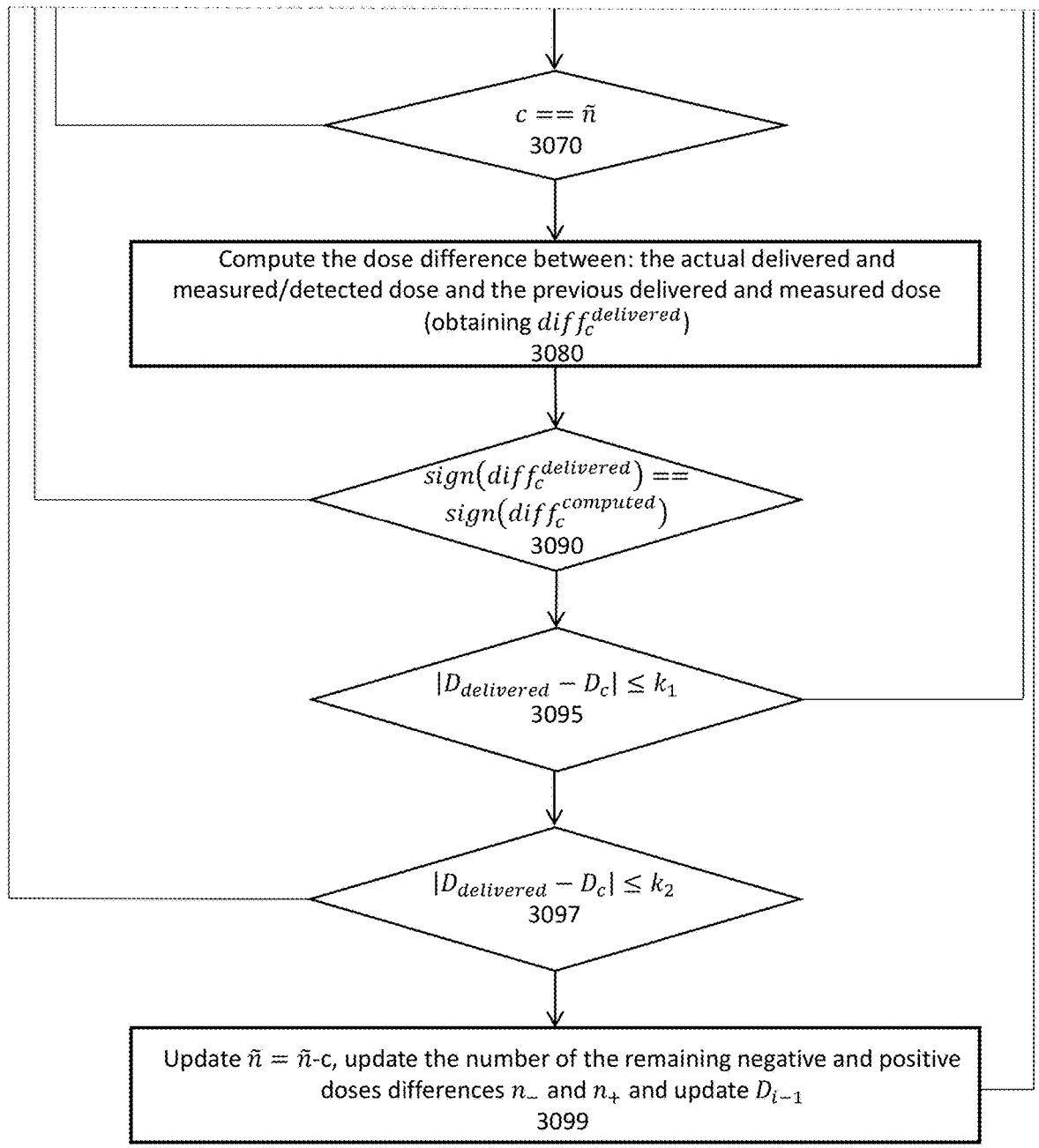

FIG. 7A-7B illustrates this exemplary method of determining a sequence of doses to be delivered during each successive puff/trial within a given stage, wherein a stage comprises a batch (or a predetermined number) of trials. For example, in FIG. 7A-7B a first batch of 20 "high-level" doses of a given substance (or active ingredients such as nicotine, or TPM), may be delivered (optional) 3000. For a non-limiting example, in a certain embodiment, an high dose of nicotine can be considered 0.1 mg. After that, a first initialization may occur, in which a computational stage comprising ñ=$n_-+n_+$ doses (where ñ represents the total dose to be delivered, or the total number of doses differences to be computed/initialized; $n_-$ represents the number of negative doses differences to be computed within the actual stage, and $n_+$ represents the number of positive doses differences to be computed within the actual stage) is initialized, such that a sequence of positions for $n_-$ negative doses differences and $n_+$ positive doses differences is determined (e.g., randomly). For instance a sequence of randomly positive and negative doses differences may result as follows: $\text{diff}^-$, $\text{diff}^-$, $\text{diff}^-$, $\text{diff}^-$, $\text{diff}^+$, $\text{diff}^-$, $\text{diff}^-$, $\text{diff}^+$, $\text{diff}^-$, $\text{diff}^-$, $\text{diff}^-$, $\text{diff}^+$, in such a non-limiting example, we have ñ=$n_-+n_+$=12, $n_-$=9 and $n_+$=3. In general, given a predetermined ñ of doses differences to be computed, it may be necessary to have $n_->n_+$ so that the magnitude of the resulting positive doses differences will result to be greater than the negative doses differences (as it will be described in a greater detail hereinafter). Moreover, a counter initialization for the delivered doses may be performed (i.e., c=0) 3010.

After, the values of the negative doses differences may be initialized. This may be accomplished by generating $n_-$ values from a gaussian distribution with a settable or predetermined mean, $\mu_-$, and a settable or predetermined variance, $\sigma_-^2$. For instance, $\mu_-$ may be set in milligrams (mg) (for example $\mu_-=-0.016$, and $\sigma_-^2=0.03$), which means that a random generated value sampled from a gaussian distribution whose mean is equal to $-0.016$ mg and whose variance is equal to 0.03 represents a dose decrement in mg (i.e., a negative dose difference expressed in mg). The computed/initialized negative doses may be attributed to an active substance (in mg), such as nicotine, or to a TPM, etc. 3020.

After, the positive doses differences may be computed such that the average delivered dose in the actual stage (i.e., the average of the doses considered within the actual stage) will be equal to a settable or predetermined value, named $\bar{\mu}$, (for example, in certain embodiments, $\bar{\mu}$ can be set to be equal for all the stages and it may be set to be equal to a pre-computed fixed value, such as the desired average mg of nicotine or of TPM, or it may be set as a time-varying value for successive stages). For example, a suitable value for $\bar{\mu}$ may be 0.1 mg of nicotine, or 0.08 mg of nicotine, or a decreasing function of mg of nicotine or TPM or of an active substance as the number of stages increases, and so on. The positive doses differences may be set all equals between each other in a given stage (or batch of doses), and their magnitude ($\text{diff}_i^+$) may be computed adopting equation 1, which is rewritten in the following for clarity (3030):

$$\text{diff}_i^+ = \frac{(\bar{\mu} - D_{-1}) \cdot \tilde{n} - (\alpha_1 \cdot \text{diff}_1^- + \alpha_2 \cdot \text{diff}_2^- + \ldots + \alpha_{n_-} \cdot \text{diff}_{n_-}^-)}{\beta_1 + \beta_2 + \ldots + \beta_{n_+}} \quad \text{(equation 1)}$$

where, $D_{-1}$ represents the last delivered dose in the previous stage; $\alpha_i$ ($\beta_i$) i$\in$ [i$\in$ n_] (i$\in$[1,n_+]) represents the numerical value corresponding to the position, in a reverse order, of the i-th negative (positive) dose difference $\text{diff}_i^-$ ($\text{diff}_i^+$) within the full sequence of n doses differences. For instance, if $\text{diff}_1^-$ occupies the first position within the full sequence of doses differences, then $\alpha_1=\tilde{n}$; if $\text{diff}_1^-$ occupies the last but one position then $\alpha_1=\tilde{n}-1$, and so on.

The device may further compute the batch of doses to be delivered (within the actual stage) sequentially during each successive puff. Such a computation may start from the last delivered dose in the previous stage (indicated with $D_{-1}$), and summing recursively the doses differences of the initialized sequence, in the actual stage. More precisely, the first dose ($D_1$) may be computed as the sum between $D_{-1}$ and the dose difference in the first position of the computed sequence; then, the second dose ($D_2$) may be computed as the sum between $D_1$ and the dose difference in the second position, and so on. In formulae, the computation of the sequence of the doses to be delivered may be performed as: $D_i=D_{i-1}+\text{diff}_i$, where $D_i$ represents the dose in the i-th position within the sequence of doses, and $\text{diff}_i$ represents the dose difference (either positive or negative) corresponding to the i-th position within the computed sequence 3040.

At the end of the doses computations, the apparatus may check to see if each of the computed doses is comprises between a predetermined (settable) minimum (min) and maximum (max) value. For a non-limiting example, in a certain embodiment, the min value may be set equal to 0.04 mg of nicotine, and the max value equal to 0.10 mg of nicotine 3050. If not, then the system may move onto step 3010 and restart the doses computation anew (i.e., performing a new stage initialization etc.). If each of the computed doses fall within the given predetermined range, then the system may deliver the c-th dose within the computed sequence of doses (e.g., the dose computation unit may transmit the c-th computed dose to the dose delivery unit) and the system may also increment the dose counter c (i.e., c=c+1) 3060. Then, the system may check to see if the number of delivered doses has reached the number of the computed doses for the considered stage (i.e., the system may check if c==$\tilde{n}$) 3070, if such a condition is verified, then the system may start a new computational stage (i.e., the system may restart from state 3010). On the contrary, the system may compute the difference between the actual measured/estimated delivered dose (e.g., measured or estimated by the dose delivery unit, as described in great details hereinafter) and the measured/estimated dose delivered in the puff/trial immediately before, expressed as $\text{diff}_c^{delivered}$ 3080. After, the apparatus may check to see if the "measured/estimated" dose difference ($\text{diff}_c^{delivered}$) and the corresponding computed dose difference (termed $\text{diff}_c^{computed}$ which is equal to the difference between the actual computed dose and the computed dose immediately before in the sequence) have the same sign (positive or negative) 3090. If the two quantities are of opposite signs, then the system may perform a new initialization and a new computational stage, restarting from the point 3010. On the contrary, if the detected dose difference and the computed dose difference are of the same type (either positive or negative), then, the apparatus may check to see if the difference between the actual measured/estimated delivered dose (termed $D_{delivered}$) and the corresponding computed dose (termed $D_c$) fall within a settable or predetermined (and relatively small) range, for example within $\pm 2\%$ of the computed value $D_c$ (in some variations other range can be set, such as within $\pm 5\%$, or $\pm 6\%$, or $\pm 10\%$ etc., or within a given absolute range (e.g., within $\pm k$, where k may assume a relatively small value, such as 0.005 mg of nicotine, or 0.001 mg or 0.01 mg and so on); in formulae the check operation may be performed by evaluating: $|D_{delivered}-D_c|\leq k_1$, where $D_{delivered}$ represents the measured delivered dose, $D_c$ represents the computed dose for the considered puff/trial, and $k_1$ may be expressed in percentage of the computed dose, such as, for example, $k_1=0.02 \cdot D_c$ (if a range of $\pm 2\%$ is considered), or it may be expressed as an absolute value in mg, such as $k_1=0.005$ mg (or $k_1=5$ μg), and so on) 3095. In a certain embodiment, $k_1$ may be set equal to 0.005 mg of nicotine. If the difference between the measured ($D_{delivered}$) and the computed ($D_c$) doses fall within the predetermined range, then the apparatus may deliver the c-th computed dose and increment the counter (going back to the state 3060). On the contrary, the apparatus may check to see if the difference between the measured delivered dose (i.e., the dose measured/estimated and transmitted from the dose delivery unit to the dose computation unit, as described in a great detail herein) and the corresponding computed dose is comprises within a second range (wherein, such a second range is greater or coarser than the first range previously considered): $|D_{delivered}-D_c|\leq k_2$, where $k_2>k_1$, 3097 (for a non-limiting example, $k_1=0.025 \cdot D_c$ and $k_2=0.1 \cdot D_c$ or $k_1=0.005$ mg and $k_2=0.01$ mg). If the abovementioned condition is satisfied, then the system may perform a new initialization of the remaining negative doses differences of the actual stage, and a new computation/initialization for the remaining positive doses differences 3099; in other words, the apparatus may update: 1) the number of the total remaining doses differences, $\tilde{n}=\tilde{n}-c$, 2) the number of the remaining negative and positive doses differences, $n_-$ and $n_+$, and, after that, the system may return to the state 3020. Conversely, if the difference between the measured delivered dose and the computed one is out of the above mentioned predetermined range (i.e., $|D_{delivered}-D_c|>k_2$), then the apparatus may perform a new computational stage and a new initialization for all the doses differences, restarting from the state 3010.

It is worth noting, that other methods for computing a sequence of doses (or amounts of ingredient(s) or vapor) that satisfy the constraints and the features described above (e.g., the feature that the average positive dose difference is greater in magnitude than the average negative dose difference, the constraint that the average cumulative delivered (or vaporized) dose is kept constant over time or it is reduced (or it is imposed/set as desired), the constraint that a dose can only assume values within a given range delimited by a settable or predetermined maximum value and a settable or predetermined minimum value and/or that each dose difference can only assume values within predetermined ranges), can be adopted with the present invention.

Smoke Reduction or Cessation and Addiction Reduction Methods and Apparatuses

In some embodiments, disclosed herein are methods and apparatuses that allow or facilitate a user in smoke cessation or in reducing a given substance addiction (e.g., nicotine addiction) or in smoke reduction. In particular, in some embodiments, a method for smoke cessation or smoke reduction or nicotine addiction reduction may include: calculating and delivering varying doses of vapor (or material or active ingredients) to a user over sequential puffs/trials, such that, starting from a given trial, the average positive dose difference is greater in magnitude than the average negative dose difference, subject to the constraint that the average cumulative administered dose (i.e., the sum of the doses delivered over successive puffs/trials divided by the number of trials) of active drug or of active physiological principle or of active ingredients is gradually reduced (e.g., by reducing the vapor, or the TPM, or the concentration of the active substance in the liquid compound of vaporizable material), and subject to the constraint that a dose can only assume values within a given range delimited by a settable or predetermined maximum value and a settable or predetermined minimum value, and/or subject to the constraint that a dose difference can assume values within predetermined or settable ranges; wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

Without desiring to be bound by theory, it is argued that increasing the reactive contributions (i.e., the neurophysiological effects due to classical conditioning or reinforcement and/or unconditioned stimulus revaluation) while reducing the active contributions (i.e., by reducing the active drug or ingredient to reduce the effects provoked by the active ingredients) may determine a reduction in the physical addiction, while the overall stimulus perception (active plus reactive contributions) remains constant or even increases. Moreover, after the accomplishment of the above-mentioned procedure, a decreasing of the reactive contributions can be employed, in order to extinguish the reactive responses/effects (which, in general, may be resistant-to-extinction, so that it could not be sufficient to extinguish them by simply performing a progressive reduction of the active delivered doses without accomplishing a proper schedule for the reactive contributions reduction), and the method may include: calculating and delivering varying doses of vapor (or material or active ingredients) to be delivered over sequential puffs/trials, such that, starting from a given (predetermined) trial, the average positive dose difference is smaller in magnitude than the average negative dose difference, subject to the constraint that the average cumulative delivered dose (i.e., the sum of the doses delivered over successive puffs/trials divided by the number of trials) of active drug or of active physiological principle or of active ingredients is kept constant or gradually reduced (or set up as desired), subject to the constraint that a dose can only assume values within a predetermined range delimited by a settable or predetermined maximum value and a settable or predetermined minimum value, and/or subject to the constraint that a dose difference can assume values within predetermined ranges; wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

Example

Figure 11:
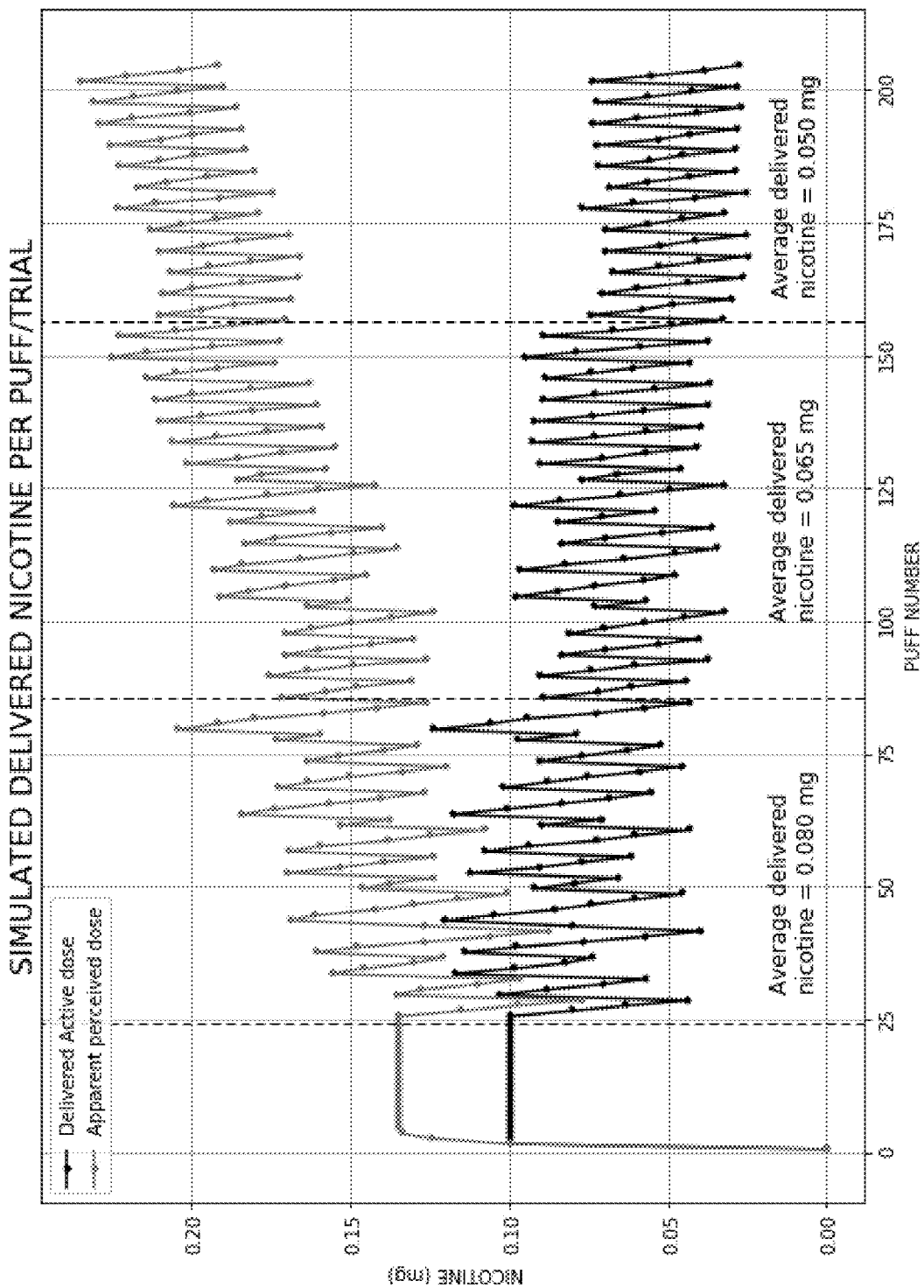
FIG. 11 is a graph illustrating a simulation of the number of puffs relative to the nicotine release content (mg) of an electronic vaporizer in which a method for enhancing the neuropsychophysiological effects of the nicotine (i.e., the apparent perceived nicotine dose) is employed as described herein, compared with the apparent perceived dose of nicotine (the apparent dose is equal to the delivered active dose plus a dummy dose which takes into account the reactive contributions, as described with detail specificity hereinafter).

FIG. 11 shows graphical simulated data depicting the number of puffs relative to the nicotine release content (mg) from a reservoir of an electronic vaporizer device in which a method of sequential doses computation is implemented. More specifically, a method similar to that depicted in FIG. 7A-7B and described above has been applied, with some variants which will be illustrated below, in a great detail.

FIG. 11 shows also the difference between the active delivered dose (in mg) and the apparent dose actually perceived by the user (in mg), wherein the apparent perceived dose comprises the sum of two contributions: 1) the delivered dose and 2) the reactive contributions. The reactive contributions comprise conditioned automatic responses and, mainly, the cumulative reactive response associated with the perceived stimuli (e.g., chemosensory features, nicotine perception, rituals, etc.), wherein such a response is cumulative, since it depends on previous interactions between the user and the stimuli, since, an implicit learning about the biological value, of the stimuli related to a puff, takes place over successive puffs/trials. The reactive response associated with the stimuli may increase due to a process of unconditioned stimulus (UCS) inflation (or UCS increase), by means the adoption of one of the methods disclosed herein.

Without desiring to be bound by the theory, it is expected that the increments of the reactive response decrease as the apparent dose increases (not shown), on the basis of the Weber-Fechner law.

In FIG. 11, during the first two stages, comprising 12 puffs/trials each, a constant dose of nicotine equal to 0.10 mg is delivered. It can be noted that even during a constant nicotine dose delivery, the apparent perceived dose by the user is greater than the delivered dose. In other words, if an user was given 0.1 mg of nicotine (and the other substances present in each puff) in an hidden mode, then (and only in such a case) the apparent dose will coincide with the delivered dose, since conditioned stimuli (e.g., rituals, chemosensory cues, etc.) and the expectation and implicit learning contributions (e.g., the reactive contributions associated with the perceived stimuli during a puff, due to previous learning and unconditioned stimulus revaluation over successive previous interactions between the user and the delivery device) would not be present. In a more realistic scenario, the apparent dose during the first puffs/trials in FIG. 11 should grow more slowly than how is shown, since it would have to be considered the effect of classical conditioning during the first few trials, during which the synaptic strength between the neural representations of the stimuli related to taking a puff and the neural representations of the reactive response associated with such stimuli, should be slowly strengthened (not shown here). However, this should only apply to the first few puffs/trials, until the statistical contingency between taking a puff and the related effects converges toward the unity (in practical this is expected to occur in about 10-20 trials); furthermore, classical conditioning becomes secondary and non-significant with respect to the effect of the UCS revaluation process after the first few puffs/trials.

Then follow further 15 stages (i.e., sequences of puffs/trials) of 12 puffs/trials each. During such stages, the dose to be delivered are pseudo-randomly computed, such that, starting from the 25-th puff/trial, the positive doses differences are greater in magnitude with respect to the negative doses differences, subject to the following constraints: 1) the average dose to be delivered within the puffs/trials of a given stage (expressed as $\bar{\mu}$ in the following) varies between stages as follows: in the first 4 stages the value for the average dose of nicotine per puff is set to 0.08 mg, from stages 5 and 10 the average dose is set to 0.065 mg, finally, for the remaining stages, the average dose is set to 0.050 mg; 2) the maximum and the minimum value of nicotine that a dose can take are set as follows: min=$\bar{\mu}$/2 and max=2$\bar{\mu}$ where $\bar{\mu}$, as stated above, represents the average dose of nicotine to be delivered within the puffs/trials of a given stage; 3) if the dose delivered in the last puff/trial of the previous stage is greater than the average dose set for the actual stage, then the first dose for the actual stage is set to be equal to the last dose of the previous stage; on the contrary, a positive dose difference is forced for the computation of the first dose of the considered stage; such a procedure assures that a relatively "high" dose is delivered at the beginning of each stage, and this may be beneficial from a neurophysiological perspective. The computation of the doses in each stage is pseudo-random, as stated above; more specifically, the method depicted in FIG. 7A-7B and disclosed herein is adopted: firstly a stage of 12 doses to be delivered is considered (i.e., ñ=12), a pseudo-random initialization for the 12 "positions" of the doses differences is performed taking into account the constraints described above, moreover three positive doses differences (i.e., $n_+$=3) and nine negative doses differences (i.e., $n_-$=9) are considered (3010 in FIG. 7A); after, the $n_-$ negative doses differences are randomly initialized taking samples from a gaussian distribution with the mean equals to −16 (i.e., $\mu_-$=−16; note that it represents a value equals to 16/1000 mg=0.016 mg as will be explained below) and with the variance equals to 3 (i.e., $\sigma_-$=3), 3020 in FIG. 7A.

Hence, the simulation illustrated in FIG. 11, shows how the reactive contribution can be enhanced over successive puffs/trials through the delivery of a plurality of sequential and varying doses of nicotine applying one of the methods disclosed herein. It is important to note that vaping (or puffing) with the methods and apparatuses disclosed herein may allow to increase also others reactive responses associated with different inhaled substances in addition to nicotine, such as active substances which may be vaporized together with nicotine (for example during vaporization of a tobacco stick within a THS device).

For the simulation, it has been assumed that the prediction error, computed within the central nervous system in a given puff/trial, is proportional to the difference between the perceived (apparent) dose during such puff/trial and the exponential moving average (EMA) of the previous perceived (apparent) doses, and that the weight associated with such a prediction error is computed on the basis of the magnitude (i.e., the absolute value) of the prediction error itself following a sigmoid function (Puviani, L., & Rama, S. (2018). Understanding and exploiting prediction errors minimization within the brain in pharmacological treatments. Behavioural brain research (Volume 359, 1 Feb. 2019, pages 223-233)).

More specifically, the prediction error at the i-th puff/trial is computed as:

$$err_i = s_i - S_i$$

where, $s_i$ represents the perceived dose at the i-th puff/trial, which comprises two contributions: the active delivered dose contribution, expressed as $D_i$ in the following; and the reactive contribution, due to the implicit UCS (unconditioned stimulus/i) revaluation process, expressed as $iR_{i-1}$ in the following, which represents the reactive response associated with the stimuli related to "taking a puff" (e.g., chemosensory features, sensations, ritual features, etc.):

$$s_i = D_i + iR_{i-1}$$

It is worth noting, that the reactive response associated with the puff related stimuli at uff/trial i, $iR_{i-1}$, is updated (i.e., revaluated) until the (i−1)-th puff/trial.

Furthermore, $S_i$ represents the exponential moving average of the perceived (i.e., apparent) doses of the previous puffs/trials, and it may be computed as:

$$S_i = \beta \cdot s_{i-1} + (1-\beta) \cdot S_{i-1},$$

$$S_0 = 0,$$

where, the parameter $\beta$ represents the degree of weighting decrease of the previous perceived doses (a constant smoothing factor between 0 and 1).

The reactive response, $iR_i$, is computed as:

$$iR_i = iR_{i-1} + \alpha \cdot \text{sigmoid}(err_i, m, \theta),$$

$$iR_0 = 0,$$

where, $\alpha$ represents a learning parameter, and the sigmoid function (with parameters: $err_i, m, \theta$) represents the weighting function for the computation of the weight of the prediction error, $err_i$.

The sigmoid function can be computed as:

$$\text{sigmoid}(x, m, \theta) = \frac{1}{1 + \exp(-m \cdot (|x| - \theta))}$$

The numerical values adopted for the parameters of the simulation shown in FIG. 11 are: $\alpha$=0.25, $\beta$=0.7, m=0.075, $\theta$=45, and the doses ($D_i$) have been computed considering a multiplicative factor of 1000 (for instance, 0.08 mg were initially computed as 80), for numerical reasons, and only at the end of all the computations involved in the simulation the delivered doses and the simulated perceived doses have been divided by the same factor 1000.

Calculation of the Partial Doses to be Vaporized during Successive Time Intervals and Calculation of the Power to be Applied to the Heater for Vaporizing the Vaporizable Material As disclosed in the technical literature (Robinson, Risa J., et al. "A framework to investigate the impact of topography and product characteristics on electronic cigarette emissions." PloS one 13.11 (2018): e0206341), the flow conditions (e.g., the puff flow rate, the puff duration) and the power delivered to the heater for vaporize the vaporizable material, may be exploited for the estimation or prediction of the vaporized dose in an electronic vaporizer device. The methods for estimating and/or predicting a dose of delivered vapor, disclosed in the art, or the methods disclosed herein, may all be suitable and adoptable with the invention disclosed herein.

In a certain embodiment, a computed dose or amount of vapor to be vaporized within a vaporizing device, such as device 60, during a (predicted) puff duration (or time period), may be subdivided in several partial doses each of which may be delivered or vaporized at each successive partial dose time intervals, wherein all the partial dose time intervals form the overall time period (or the puff duration). The dose delivery unit (such as dose delivery unit 220), may subdivide the computed dose (such as computed dose to be delivered 219), into a number of partial doses equal to the predicted number of partial time intervals, wherein the successive partial time intervals form the predicted puff duration (such as predicted puff duration 213). In some embodiments, the partial doses may all be set equal to each other; more specifically, a computed dose to be delivered during a puff, whose puff duration has been predicted by the puff duration predictor unit (such as puff duration predictor unit 212), may be equally subdivided by the number of time intervals which form the predicted puff duration, so that the partial doses to be delivered during each successive time intervals can be determined (for example, $\Delta m = \Delta m_i = D_c/n_{predicted}$, where, $\Delta m$ represents the computed partial dose to be delivered, $\Delta m_i$ represents the partial dose to be delivered during the i-th time interval, $D_c$ represents the computed dose to be delivered during a given puff and $n_{predicted}$ represents the predicted puff duration expressed in numbers of partial time intervals, wherein each partial time intervals may be between 10 ms and 200 ms, such as 20 ms, or 25 ms, or 30 ms, etc.). In some variations, different subdivision of the total computed dose between the time intervals forming the predicted puff duration may be performed.

In a certain embodiment, the amount of power to heat the vaporizable material (e.g., in some variations, the power applied by the heater controller to the heater) to vaporize the vaporizable material during a partial dose time interval, may be computed from the partial dose to be delivered during the partial dose time interval, the temperature generated during vaporization and the flow rate due to the puff during the vaporization. That is, the computed partial dose to be delivered during a partial dose time interval, the temperature of the vaporized material, as measured by a temperature sensor (such as temperature sensor 250) and the flow rate, as measured by a puff sensor (such as puff sensor 270), can be used to determine the amount of power to be delivered to the heater to vaporize the computed partial dose.

In some embodiments, the power to be delivered to the heater can be predicted or determined based upon equation 2:

$$P_i = \frac{1}{\theta_1}\Delta m_i - \frac{\theta_2}{\theta_1}T_{i-1} - \frac{\theta_3}{\theta_1}F_{i-1} \qquad \text{(equation\_2)}$$

where $\Delta m_i$ is the partial dose of vapor/material (or active ingredient) to be delivered to the user during sampling intervals i=1 to i=n, each interval being of a fixed time increment; $\theta_1$, $\theta_2$, $\theta_3$ are constants to be determined empirically as illustrated hereinafter, $P_i$ is power to be delivered to the heater during interval i, $T_{i-1}$ is temperature reading for interval immediately before the current interval (i−1 immediately prior to interval i) and $F_{i-1}$ is flow rate reading for interval immediately before the current interval (i−1 immediately prior to interval i). Note that in some variations, the temperature may be temperature relative to room (or starting) temperature and may be expressed as T' (e.g., $T'_{i-1}$,)

The coefficients $\theta_1$, $\theta_2$, $\theta_3$ may reflect physical constants whose values can be determined experimentally and can vary depending on the vaporizable material used. The constants can further depend upon the overall mass of the system that needs to be heated (such as the liquid material and the heater, e.g., a wick and coil). In general, these constants may be determined empirically.

In some embodiments, the total mass vaporized can be predicted or determined based upon equation 3:

$$\Delta m_{cum} = \sum_{i=1}^{i=n}\Delta m_i = f(P_i, T_{i-1}, F_{i-1}) = \sum_{i=1}^{i=n}\theta_1 P_i + \theta_2 T_{i-1} + \theta_3 F_{i-1} \qquad \text{(equation\_3)}$$

where $\Delta m_{cum}$ is the total amount of vapor/material (or active ingredient) delivered to the user during sampling intervals i=1 to i=n, each interval being of a fixed time increment.

Hence, in some embodiments, the coefficients $\theta_1$, $\theta_2$, $\theta_3$ (which hold also in equation 2) can be determined by collecting an amount of data and running a mathematical algorithm. For example, an analytical inhalation or smoking machine can be used to test the vaporizing device under one or more conditions. During the tests, it is preferred to vary the power applied to the heater element within a given range, wherein the range is delimited by the minimum and the maximum power values which are designed or allowed to work with the electronic vaporizer (for some non-limiting examples the power range can be between 4 W and 10 W, or between 5 W and 12 W, or between 3 W and 30 W, and so on). Total particulate matter (TPM) can be collected from the vaporizing device using the analytical inhalation or smoking machine. In some cases, the TPM can be collected on a filter pad. The filter pad can be weighed before and after TPM is collected on the filter such that the weight of the TPM on the filter can be determined. In some embodiments, the empirical determination of ($\theta_1$, $\theta_2$, $\theta_3$) is accomplished by measuring power, temperature and flow rate over a series of puffs and measuring the cumulative mass lost by the device for those puffs gravimetrically.

The mass lost by the device is taken as being equal to total delivered mass of TPM (mg). Best values for $\theta_1$, $\theta_2$, $\theta_3$ are then determined by fitting the above equation to the experimental mass delivery, power temperature and flow rate data.

Adjustments in the constants can be made to accommodate the variance in the type of the device and of the formulation.

One example of a method for determining the values of the constants associated with the relationship between the mass of vapor emitted, power applied to vaporize the material during a particular time interval (e.g., portion of a puff), the temperature of the material before vaporization during that period and the puff flow rate before vaporization during that period, is described below. In this example, the device may be first weighed. Then, a series of puffs may be taken while varying and logging the temperature, the flow rate and the power (e.g., at a sampling frequency such as 20 Hz, e.g. between 5 Hz and 100 Hz, 5 Hz and 200 Hz, etc.) while varying the power applied to the heater element randomly or deterministically within the allowed range of powers (for example, power can be varied with steps of 1% or 2% or 3% or 4% or 5% or 6% or 10% of the allowed maximum power value, preferably with steps of 2% of the maximum allowed power, that is, if the allowed range of powers for the electronic vaporizer is 3 W-10 W, then the power can be varied with steps of 0.2 W starting from 3 W) through the duration of the trial. The device may then be weighed again. This may be repeated many times (e.g., more than 5, 10, 15, 20, 25, 30, 35, 40, 45, 50, 60, 70, 80, 90, 100, 120, 150, 200, etc., or between 5 and 1000, between 10 and 500, between 10 and 200, etc.) to achieve a sufficiently sized data set. In one example, the process is repeated 39 times. The vaporized mass may then be calculated for each sample by subtracting the final mass from the initial mass. Alternatively, the mass of the vapor may be directly measured, e.g., by applying the vapor onto a filter pad and use the change in mass of the pad to get vaporized mass; this may be less accurate because some of the vapor might go through the pad or deposit on other surfaces. For simple gravimetric analysis, measuring the device may be preferred.

After collecting all the data, the vaporized mass estimates, as well as a set of values for temperature, power and flow rate over the duration for each sample may then be used to solve for the constants. For example, in equation 3, the constants $\theta_1, \theta_2, \theta_3$ may be determined from this data. For example, the values of $\theta_1, \theta_2, \theta_3$ may be determined such that $SUM[t=1 \text{ to } t-n](\theta_1 P_i+\theta_2 T_{i-1}+\theta_3 F_{i-1})$ may be solved to find the best fit to the vaporized mass that was measured for each sample.

This may be performed for any expression of the vapor mass, applied power, temperatures measured and flow rates measured. In some variations this may be performed using a gradient descent algorithm, to fit the data to the appropriate equation.

A gradient descent algorithm may be beneficial because is computationally cheap to find the optimal values of the constants (e.g., $\theta_1, \theta_2, \theta_3$) such that error is minimized. However, any appropriate curve-fitting algorithm or method may be used (for instance, machine-learning methods or algorithms may also be adopted).

In some variations, other expressions of vaporized mass, flow rate, temperature and power (or expressions of vaporized mass, flow rate and power only) different from equation 3 may be adopted. For example, for the analytical expression of the vaporized mass, polynomial and/or interaction features and/or other combination of functions of the power, temperature, flow rate (or of the flow rate, and the power) may be adopted. More specifically, an example of a second-degree polynomial and interaction combination of power, flow rate and temperature may be as follows:

$$\theta_0+\theta_1 P_i+\theta_2 T_{i-1}+\theta_3 F_{i-1}+\theta_4 P_i T_{i-1}+\theta_5 P_i F_{i-1}+\theta_6 T_{i-1} F_{i-1}+\theta_7 P_i^2+\theta_8 T_{i-1}^2+\theta_9 F_{i-1}^2.$$

As mentioned above, other expressions of vaporized mass, power, flow rate and temperature may be adopted. In such cases the number of constants to be determined is greater than three (e.g., constants $\theta_0, \theta_1, \ldots, \theta_9$). Hence, in some embodiments, in which the considered expression of the vaporized mass, temperature, flow rate and power (or only some of these or other quantities) involve interaction and/or polynomial combinations with degree equal or greater than 2 or other non-linear expressions, such as, for a non-limiting example as expressed in equation 4:

$$\Delta m_{cum}=\Sigma_{i=1}^{i=n}\Delta m_i=\Sigma_{i=1}^{n}(\theta_0+\theta_1 P_i+\theta_2 T_{i-1}+\theta_3 F_{i-1}+\theta_4 P_i T_{i-1}+\theta_5 P_i F_{i-1}+\theta_6 T_{i-1} F_{i-1}+\theta_7 P_i^2+\theta_8 T_{i-1}^2+\theta_9 F_{i-1}^2),$$ (equation 4)

the constants $\theta_0, \theta_1, \ldots, \theta_9$ (or any number of constants involved in the relation) may be computed as illustrated above; moreover, the power to be delivered to the heater at time interval i ($P_i$), for delivering a computed partial dose of vapor, can be predicted or determined in the dose delivery unit (such as dose delivery unit 220) based on numerical (iterative) algorithms, since the relation between $P_i$, $\Delta m_i$, $T_{i-1}$ and $F_{i-1}$ is non-linear. In some embodiments, $P_i$ can be computed using the Newton method setting the initial guess equal to $P_{i-1}$. More specifically, in certain embodiments, indicating $$\Phi(P_i)=\theta_0+\theta_1 P_i+\theta_2 T_{i-1}+\theta_3 F_{i-1}+\theta_4 P_i T_{i-1}+\theta_5 P_i F_{i-1}+\theta_6 T_{i-1} F_{i-1}+\theta_7 P_i^2+\theta_8 T_{i-1}^2+\theta_9 F_{i-1}^2-\Delta m_i,$$

(or, more generally, indicating with $\Phi(P_i)$ the analytical expression of the $\Delta m_i$ function of temperature, power, flow rate, etc., and the term $-\Delta m_i$) where $\Delta m_i$ represents the partial dose to be delivered during the partial time interval i, the method computes the k+1-th iteration for $P_i$ (expressed hereinafter as $P_i^{k+1}$) as:

$$P_i^{k+1} = P_i^k - \frac{\Phi(P_i^k)}{\Phi'(P_i^k)}$$

with $P_i^0=P_{i-1}$ (which is the initial guess), and $\Phi'(P_i^k)$ represents the first derivative of $\Phi(P_i)$ with respect to $P_i$ and evaluated at $P_i=P_i^k$. Moreover, the number of iterations may be limited by setting a given stop condition, such as:

$$|P_i^{k+1}-P_i^k|<\varepsilon \text{ and/or } |\Phi(P_i^{k+1})|<\delta,$$

where $\varepsilon$ and $\delta$ have to be small (for example they can be set equal to $2 \cdot 10^{-7}$), but greater than $10^{-7}$ if the operations are performed in single-precision or greater than $10^{-16}$ if the operations are performed in double-precision. It is worth noting that other iterative numerical methods other than the Newton method can be adopted for the computation of the $P_i$, such as quasi-newton methods and others.

In some embodiments, the time interval i (e.g., the partial dose time interval) can be between 20 ms and 200 ms (e.g., less than 200 msec. 180 msec. 150 msec. 120 msec, 100 msec, 90 msec, 80 m·sec. 70 msec, 60 msec, 50 msec, 40 msec, 30 msec. 20 msec, 10 msec, etc.). The temperature, the flow rate and the power measurements can be taken at a frequency of between 5 and 50 Hz, such as between 10 and 30 Hz, such as at approximately 20 Hz.

In general, the power to may refer to power delivered to heat the vaporizable material (e.g., in some variations, the power applied by the heater controller to the heater) to vaporize the vaporizable material during a partial dose time interval. During the tests for determining the constants, such as, for example, $\theta_1, \theta_2, \theta_3$ in equation 3 (which are the same as those expressed in equation 2) the power applied may be read directly from the heater controller (e.g., a watts, joules, joules/sec², volts*volts, volts*volts/resistance, etc.) and/or may be sensed, e.g., using any appropriate power sensor (voltmeter, hall effect sensor, inductive sensor, direct measurement sensor, voltage response measurement sensor, etc.

The power may be detected either immediately before or during the time interval (e.g., partial dose time interval), representing the power applied to vaporize the material during that interval. For example, the power used to determine a partial dose may be transmitted from the heater controller simultaneous with applying the power to the heater, in some variations the power ($P_i$) is the power applied during the interval immediately before the interval i (e.g., i−1) because this power is then absorbed by the vaporizable material during the dose interval being measured. Alternative, when the power ($P_i$) may be the power sensed directly or indirectly during the relevant dose interval (i).

As mentioned, during the utilization of the vaporization device, the power $P_i$ is computed in the dose delivery unit on the basis of the temperature, flow rate, and the mass of vapor or material to be delivered.

The temperature of the vaporizable material being vaporized before the partial dose time interval may refer to the dose from the immediately prior time interval (e.g., $T_{i-1}$), which may be the temperature at the start, end or during the prior time interval. For intervals that are sufficiently brief, this distinction may be irrelevant. Alternatively, in some variations the temperature of the vaporizable material being vaporized before the partial dose time interval may refer to the temperature of the material to be vaporized immediately before the $P_i$ is applied (e.g., at the start or just before the start, of the application of power).

Similarly, the flow rate before the partial dose time interval may refer to the dose from the immediately prior time interval (e.g., $F_{i-1}$), which may be the flow rate at the start, end or during the prior time interval. For intervals that are sufficiently brief, this distinction may be irrelevant. Alternatively, in some variations the flow rate before the partial dose time interval may refer to the flow rate measure immediately before the $P_i$ is applied (e.g., at the start or just before the start, of the application of power).

The temperature and power applied to the material to be vaporized typically refers to the temperature and power applied to the portion of the material (e.g., the material on the wick in some variations) that will end up reforming into a vapor through the application of the energy, e.g., near the surface, rather than the bulk of the material to be vaporized.

As mentioned, the partial dose to be delivered in the partial dose time interval (i), named $\Delta m_i$, is computed in the dose delivery unit on the basis of: a) the computed dose to be delivered during the puff duration (transmitted by the dose computation unit to the dose delivery unit), b) the puff duration predicted by the puff duration predictor unit.

In some embodiments, during tests the TPM can be adjusted to determine the total amount of a particular compound inhaled, such as the total amount of an active ingredient, such as nicotine. For example, the TPM can be multiplied by the percentage of active ingredient in the vaporizable material.

In some embodiments, a vaporizing device, such as device 60, can be calibrated based on a previous measurement performed using a same or similar device such that an amount of vaporized material can be determined based upon the performance of the same or similar device. For example, the device can be calibrated through a function fit method to determine a relationship between total particulate matter (TPM) release content (mg) and one or more vaporization parameters of aerosolizing materials from the device by a function fit method.

In some cases, the method for calibration of the device to obtain active material content from the relationship of total particulate matter (TPM) release content (mg) to vaporization parameters of aerosolizing materials can comprise setting up an analytical inhalation or smoking machine to its functioning operating parameters and testing the device under one or more conditions. In some cases, conditions that can be varied can comprise puff volume and/or flow rate. The conditions (e.g., vaporization parameters) can include one or more variable chosen from the group consisting of puff duration (sec), puff volume (ml), flow rate (ml/sec), power (watts), voltage (volts). In some cases, exemplary ranges include, but are not limited to 1 mL-100 mL volume; 0.2 s-10 s duration; 2-100 mL/s; 2.5-4.2V, respectively.

Total particulate matter (TPM) can be collected from the electronic vaporizer device. In some cases, the TPM can be collected on a filter pad. The filter pad can be weighed before and after TPM is collected on the filter such that the weight of the TPM on the filter can be determined. In some cases, the weight of the filter can be tared. The weight of the material in the device to be vaporized can be recorded prior to vaporization. In some cases, the weight of the vaporizable material in the device can be measured and recorded prior to operating the device. The weight of the vaporizable material in the device can be measured and recorded after one or more puffs on the device. A difference in weight of the vaporizable material between the initial weight and the weight after one or more puffs can be compared to a weight of TPM collected on the filter. In some cases, the difference in weight of the vaporizable material between the initial weight and the weight after one or more puffs and the weight of TPM collected on the filter can be substantially the same. The TPM collected on the filter can comprise material vaporized from the vaporizable material in the device during the one or more puffs.

In some cases, an analytical inhalation or smoking device can be a machine configured to simulate inhalation of a vaporized material from a vaporizing device by a human.

While the machine smoking device vaporizes the formulation in the one or more devices, TPM from the device can be collected onto one or more filter pads. Each device can have TPM released from the electronic vaporizer device collected on a different filter pad. For each filter pad the amount of TPM released by a device can be determined. The amount of TPM released by an individual device relative to the initial weight of vaporizable material can be calculated. In some cases, this procedure can be repeated with variable inhalation conditions, for example, with progressively increasing and/or decreasing puff duration (sec or msec) of the machine inhalation or smoking device. In some cases, the procedure can be repeated with varying puff volume (ml) of the machine smoking device. The puff volume can vary in the range of 1 mL-100 mL, more preferably, 20-80 mL, most preferably 30-60 mL. In some cases, the procedure can be repeated with varying flow rate of the machine smoking device. Flow rate of the machine inhalation or smoking device can vary in a range of 2-100 mL/s, more preferably, 5-50 mL/s, most preferably 10-30 mL/s.

In some cases, the procedure can be repeated with varying power of the machine inhalation or smoking device. Power (watts) of the smoking device can vary in the range of 2 watts to 20 watts, more preferably 3 watts to 8 watts. In some cases, the procedure can be repeated with varying voltage of the machine inhalation or smoking device.

Voltage of the device can vary in a range of 2.5-4.2V, more preferably 3.0-4.2V.

The puff volumes to the corresponding TPM release content (mg) can be tabulated. A relationship between puff volume and corresponding TPM release content (mg) can be displayed graphically and/or in a table and can be used to predict, determine, or estimate the amount of vapor consumed by the user when using a device.

The values can be transmitted to the device, such as the microcontroller within the PCB 69 of device 60, through a wireless or wired data transfer.

The described methods for the determination of the vaporized mass and others, known in the art, can all be adopted with the present invention.

Calculation of Vaporizable Material Vaporized (or Vaporized Mass or Delivered Dose)

In a certain embodiment, the amount of vapor generated from a vaporizable material within a vaporizing device, such as device 60, can be calculated summing all the delivered partial doses, as computed by the dose delivery unit (such as dose delivery unit 220). More specifically, starting from the computed dose to be delivered during the actual puff duration and from the predicted puff duration, the dose delivery unit may compute the partial doses dividing the computed dose by the predicted puff duration, wherein the puff duration is expressed in units of partial dose time intervals, wherein each partial time intervals may be between 10 ms and 200 ms, such as 20 ms, or 25 ms, or 30 ms, etc. as already mentioned, obtaining the partial dose to be delivered at each time intervals (i.e., $\Delta m_i$); after, the dose delivery unit may compute the power $P_i$ (for example on the basis of the equation 2) which has to be delivered to the heater for vaporizing $\Delta m_i$ at each time interval and storing the partial sum of the partial doses delivered until the i-th time interval; hence, if the actual puff duration involve a greater (smaller) number of partial time intervals than that involved in the predicted puff duration predicted by the puff duration predictor unit, then the actual vaporized (or delivered) dose may be computed summing the actual delivered partial doses, so that the effectively (actual) delivered dose can be obtained, regardless the value of the predicted dose to be delivered and regardless the predicted puff duration.

It is worth noting that only in case that the actual puff duration coincides with the predicted puff duration, the computed dose (obtained by the sum of the partial doses delivered at each sequential time interval) will be equal to the computed dose to be delivered during the puff (wherein the computed dose is computed in dose computation unit).

In some variants, the amount of vapor generated from a vaporizable material within a vaporizing device, such as device 60, can be calculated from the power supplied to a vaporizable material by a power source, the temperature generated during vaporization and the flow rate due to the puff during the vaporization. That is, the power consumed by the power source (such as power source 230), the temperature of the vaporized material, as measured by a temperature sensor (such as temperature sensor 250) and the flow rate, as measured by a puff sensor, can be used to determine the amount of vapor generated and/or inhaled. For example, equation 3 or equation 4 or other similar relations (some of which are well known in the art) may be adopted for the computation of the amount of dose delivered.

In a certain embodiment, the equation 3 can be adopted (which is rewritten in the following for completeness):

$$\Delta m_{cum} = \sum_{i=1}^{i=n} \Delta m_i = f(P_i, T_{i-1}, F_{i-1}) = \sum_{i=1}^{i=n} \theta_1 P_i + \theta_2 T_{i-1} + \theta_3 F_{i-1} \quad \text{(equation\_3)}$$

where $\Delta m_{cum}$ is the total amount of vapor/material (or active ingredient) delivered to the user during sampling intervals i=1 to i=n, each interval being of a fixed time increment; $\Delta m_i$ is the partial dose delivered during time interval i, $\theta_1, \theta_2, \theta_3$ are constants, $P_i$ is power supplied during interval i, $T_{i-1}$ is temperature reading for interval immediately before the current interval (i−1 immediately prior to interval i) and $F_{i-1}$ is flow rate reading for interval immediately before the current interval (i−1 immediately prior to interval i). Note that in some variations, the temperature may be temperature relative to room (or starting) temperature and may be expressed as T' (e.g., $T'_{i-1}$,).

The coefficients $\theta_1, \theta_2, \theta_3$ may reflect physical constants whose values can be determined experimentally and can vary depending on the vaporizable material used as described in great detail above.

Figure 6:
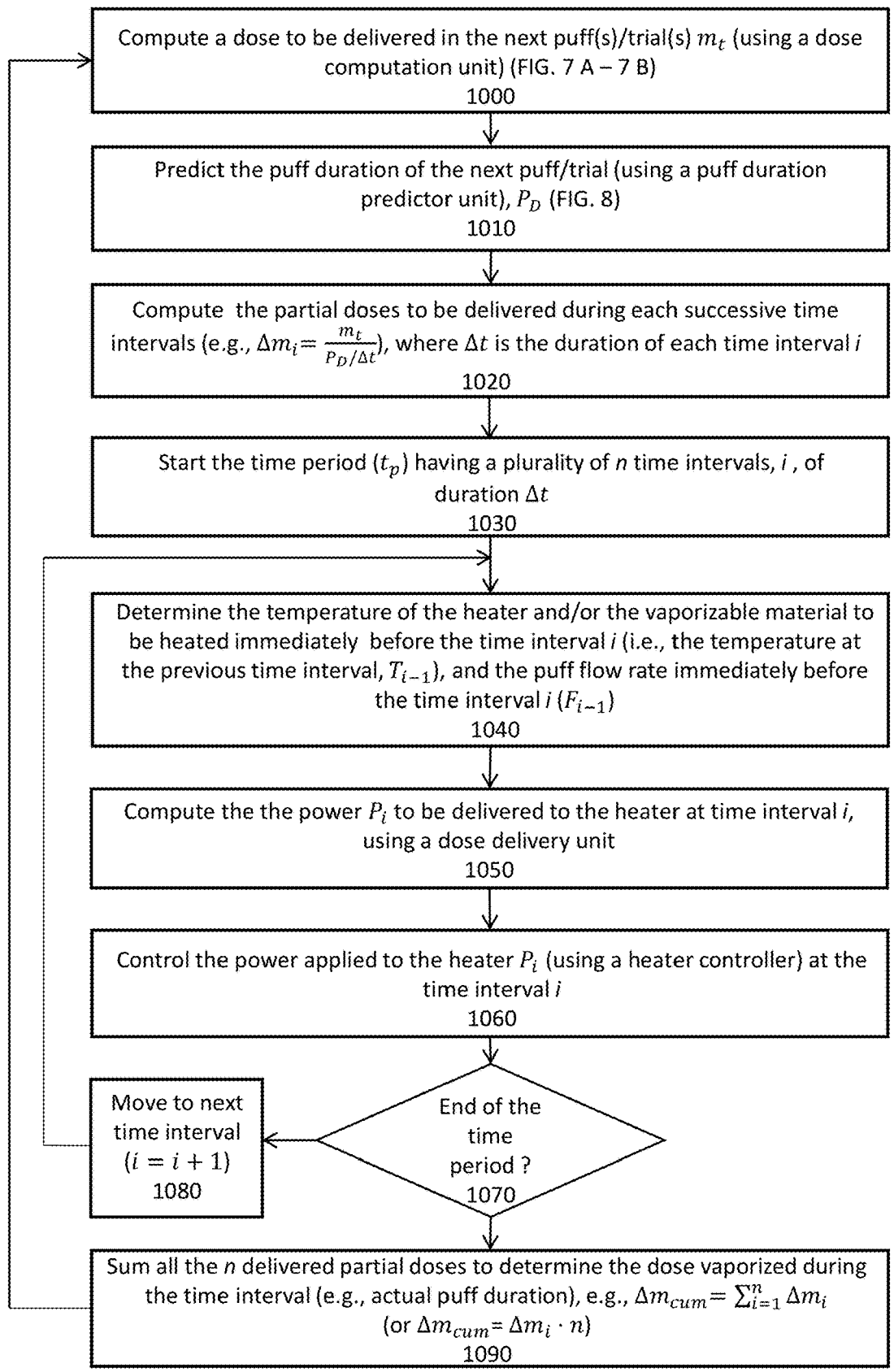
FIG. 6 schematically illustrates one method of computing, delivering and estimating a dose of vapor over a time interval in order to increase the neuropsychophysiological effects of the vaporized substance(s), as described herein.

FIG. 6 illustrates a method of computing a power $P_i$ to be delivered to the heater in the i-th time interval, and determining a vapor dose delivered over time interval as described above. For example, in FIG. 6 the apparatus may compute one or more dose(s) (i.e., in the dose computation unit) 1000; after, or in parallel, the system may predict a puff duration (i.e., in the puff duration predictor unit) 1010. In a certain embodiment, the partial doses to be vaporized during each of the sequential time interval may be computed dividing the computed dose to be delivered ($D_c$) by the number of time intervals which form the predicted puff duration $P_D$ in ms (e.g., $$\Delta m_i = \frac{D_c}{P_D/\Delta t},$$

wherein, the term $\Delta t$ represents the time duration of each time interval, in ms) 1020. Hence, the time period for determining the power and the partial dose ($t_p$) may be initially set or started 1030.

The start of the time period 1030, may be triggered by the user, physician or other party (e.g., manually) or it may automatically start, e.g., when a user begins puffing on the vaporizer (e.g., using a puff sensor). The duration of the time period may also be predetermined (e.g., fixed, e.g., at 2 sec, 3 sec, 4 Sec, 5 sec, 6 Sec. 7 sec, 8 Sec. 9 Sec, 10 sec, 11 sec, 12 sec, 13 sec, 14 sec, 15 sec, 16 sec, 17 sec, 18 sec, 19 sec, 20 sec, 25 sec, 30 sec, 35 sec, 40 sec, 45 sec, 50 sec, 55 sec, 60 sec, 1.5 min, 2 min, 3 min, 4 min, 5 min, 10 min, 12 min, 15 min, 20 min, 30 min, 1 hr, 2 hr., 3 hr, 4 hr, 5 hr, 6 hr, 7 hr, 8 hr, 9 hr, 10 hr, 11 hr, 12 hr., etc.) or it may be variable, including set by the use or it may be determined by sensing the end of a puff. In some variations, the time period is set as the start of a session so that the total dose is determined for the entire session, which may include multiple puffs. In some variations, each puff is considered a time period (e.g., using a puff sensor); the dose may be determined per puff, or it may be aggregated over all of the puffs in a session or stage (where a session or stage may be defined as within a particular time window, e.g., 5 minutes, 10 minutes, 20 minutes, 30 minutes, 1 hour, 2 hours, etc. or it may be defined as within a particular number of puffs).

The time period typically includes a number of time intervals i (also referred to herein as partial dose time intervals), which divide the time up in to discrete sample periods for which a partial dose may be calculated and delivered. The number of time intervals (n) may be predetermined, when the time period is fixed (e.g., because a puff duration has been predicted), or it may be open (e.g., continuously incremented). The duration of the time intervals may be fixed or variable, though they are typically fixed. The duration may be, for example, between about 200 msec and about 10 msec. The time intervals may be immediately adjacent to each other (e.g., in real time), or they may be separated by an off period. The time intervals may generally be considered sequential. For each time interval, a computed power $P_i$ may be delivered, and a partial dose of vaporizable material (e.g., vapor, including any active ingredients) may be vaporized and its value may be stored in memory. This may be controlled and/or performed by a dose delivery unit portion of the apparatus (or in communication with the apparatus), as described above. During each time increment, i, the apparatus may store the temperature of the heater and/or the vaporizable material near the heater, from the previous time interval, and may store the flow rate from the previous time interval $T_{i-1}$ 1040. The temperature value ($T_{i-1}$) may reflect the temperature of the material to be vaporized during this time interval and may therefore be the temperature at the very start (or just before the very start) of the time interval; similarly, the flow rate value ($F_{i-1}$) may reflect the flow rate (e.g., the volume leaving a vaporizer device per unit of time) during this time interval and may therefore be the flow rate at the very start (or just before the very start) of the time interval. The power to be delivered to the heater for vaporizing the vaporizable material and delivering the computed partial dose ($\Delta m_i$) during the i-th time interval ($P_i$) may be computed in the dose delivery unit (for example through the computation of equation 2, or, in other variants, adopting the Newton method or other computational iterative algorithms as described above) 1050. During each time interval the apparatus controls the power applied to the heater for that interval (i) 1060. Note that when power is not being applied to heat heater, the power value may be zero; if the heater is still at a different temperature than the previous time increment (i−1), then there may still be vapor produced, if not then little vapor may be produced. The power controller (heater controller) may transmit the power that is causing to be delivered to the heater to the dose delivery unit (the dose delivery unit may then compute the extra-dose vaporized computing equation 3 using the power applied to the heater, the temperature immediately prior to the interval $T_{i-1}$ and the flow rate immediately prior to the interval $F_{i-1}$).

The delivered (or estimated) partial dose value may be stored (e.g., separately as a discrete datum, or added to a cumulative dose for the time period, or both), along with any of the information ($P_i$, $T_{i-1}$, $F_{i-1}$, etc.). The dose delivery unit may include one or more memories (e.g., memory registers) for storing these values (note that the $P_i$, in the current interval may become the $P_{i-1}$ during the next interval, so that the $T_{i-1}$ in the current interval may become $T_{i-2}$ during the next interval and so on). At the end of each time interval, the apparatus may check to see if the end of the time period has been reached, either because of a predetermined number of intervals (n) has been reached (i=n) or because of some other triggering event (e.g., the end of a puff, end of a session, etc.), or both 1070. If not, then the system may move onto the next interval, incrementing the interval (i=i+1) 1080. Once the end has been reached, in some variations (e.g., where a cumulative register has not been kept), all of the partial doses may be added 1090. Note that in any of these variations, this step of adding all of the partial doses may be done in an ongoing manner, e.g., accumulating them (summing them) as each new interval is passed. Thus, the step of summing the calculated partial doses in the dose delivery unit to determine a total dose of vapor delivered during the time period (or during the puff) may be done either at the end of the time period or it may be done during the duration of the time period.

In some variations, the actual delivered dose can be obtained as the product of the partial dose $\Delta m_i$ and the number of time intervals (n) during each of which such a partial dose has been delivered.

Prediction of the Puff Duration of a Target (Next or Incoming) Puff

In a certain embodiment, the time period related to the puff duration of a given puff (in general the next or the incoming puff), which will be initiated by an user within a vaporizing device, such as device 60, can be predicted from the puff duration predictor unit (such as puff duration predictor unit 212) from the puffing topography features (for example, the puff duration, the average puff flow rate, the average pressure drop, the interatrial puff intervals, etc.) of the puff(s) immediately before, and from the delivered doses during such puff(s), and, optionally, from the dose to be delivered in the next/incoming puff, whose duration has to be predicted.

In certain embodiments, the puff sensor (such as puff sensor 270) may transmit data to the puff duration predictor unit. The puff sensor may transmit the flow rate at each time interval during a puff/trial, and (optionally) other quantities (e.g., the pressure drop). The puff duration predictor unit, may make some computation from the data received by the puff sensor, such as computing the mean, or extracting relevant puffing topography features, such as, in certain embodiments, the time interval between successive puffs, the average pressure drop, the puff volume, the puff duration etc. In certain embodiments, the puff duration predictor unit, or the electronic vaporizer device, comprises a timer configured to determine a puff duration. The puff duration predictor unit may include one or more memories (e.g., memory registers) for storing these values (extracted features and computations).

The puff sensor may be an electro-mechanical device; alternatively, the sensor may be any of a mechanical device, an optical device, an optomechanical device, a micro electro mechanical systems (MEMS) based sensor and an acoustic sensor.

In some embodiments, the time interval i (e.g., the partial dose time interval) can be between 20 ms and 200 ms (e.g., less than 200 msec. 180 msec. 150 msec. 120 msec, 100 msec, 90 msec, 80 m·sec. 70 msec, 60 msec, 50 msec, 40 msec, 30 msec. 20 msec, 10 msec, etc.). The flow rate measurements can be taken at a frequency of between 5 and 50 Hz, such as between 10 and 30 Hz, such as at approximately 20 Hz.

In certain embodiments, a machine learning (e.g., a supervised-learning model, or a reinforcement learning model or an artificial intelligence model or a mathematical/statistical model, etc.) may be computed and updated (or in general, ran) in the puff duration predictor unit, wherein: a) in a training phase (which can be ran after each puff (e.g., online mode) to dynamically update the model and improving its prediction performances after each puff, alternatively, the training phase can be computed periodically or only when certain conditions occur, or pseudo-randomly or randomly, for instance in a mini-batch mode, where the training phase occurs only after the occurrence of some puffs/trials and such trials are considered for the training) the model takes as labeled output the puff duration of a given (target) puff/trial, and as the input the puff features of some puffs (for example 2, or 3 or 4 or 5 or 6 or 10 puffs etc.) occurred immediately before the considered (target) puff (e.g., the puff duration, and optionally other features such as the average flow rate, the time interval before the previous puff, etc.) and the corresponding/related delivered doses, and optionally, the actual computed dose to be deliver in the considered puff/trial; b) in the prediction phase, the model predicts (as output) the puff duration of the next/incoming puff (also named "target puff" herein), and the model takes as input the puffing topography features (e.g., the puff duration, and, optionally, other puffing topography features) of the puff(s)/trial(s) preceding the considered puff and the related delivered doses (and optionally, the computed dose to be deliver in the given puff/trial). It is worth mentioning that a broad spectrum of computational and/or machine learning algorithms can be adopted, such as, but not limited to: online learning algorithms (e.g., Stochastic Gradient Descent, Passive-Aggressive algorithms, recursive least squares, support vector machines, neural networks etc.), batch and mini-batch learning algorithms (support vector machines, kernel methods, gradient descent, any kind of regression, neural networks, etc.), incremental learning, progressive learning, Bayesian methods, pattern recognition, statistical models, autoregressive models.

In a certain embodiment, a passive-aggressive algorithm may be adopted as described in a greater detail hereinafter.

An example of the methods of predicting one or more puff features, such as the duration of the next/incoming puff, may include an online Passive-Aggressive algorithm, which comprises the following steps:

1) initialize the model parameters; for example, the following parameters can be initialized:
   a) a vectors of weights $w \in \mathbb{R}^n$, where n represents the number of the features for the prediction function or the model to be inferred $f(x)=w \cdot x$, where the vector x represents the features vector (for example the puff duration, the average flow rate, and/or their combinations, etc. as described in great detail hereinafter); in a certain embodiment, it may be initialized $w=(0, \ldots, 0)$),
   b) an insensitive parameter $\varepsilon$ which represents a positive parameter which controls the sensitivity to prediction mistakes; such a parameter is needed for the computation of an $\varepsilon$-insensitive loss function, defined below, (for instance, if the puff duration in ms has to be predicted, then it can be initialized $\varepsilon=100$, or $\varepsilon=50$, or, alternatively, the parameter E can be initialized as a small fraction (e.g, 1%, or 2%, or 3%, or 5%, etc.) of the average (or of the expected) value that have to be predicted; for a non-limiting example, provided that in certain embodiments the puff duration may be considered about between 1000÷4000 ms, values between 100 and 400 can be initialized for $\varepsilon$. In some embodiments, $\varepsilon$ can be set as the value (in ms) of the system time sampling (e.g., 10 ms, 50 ms, 100 ms, and so on) or as a multiple of the sampling interval. In a certain embodiment E can be set for example to 100 (ms).
   c) optionally, an aggressiveness positive parameter C, needed for the computation of an update step defined below (C have to be varied performing some tests before set it definitely; for example, some range centers for C may be: 100, 10, 1, 0.1, 0.01 and it can be determined performing a validation process of the model, e.g., through cross-validation and/or grid search, as well known in the machine learning literature and by a person skilled in the art); in a certain embodiment C can be set to 10.

2) take a vector of primary features of a settable number of the puffs/trials that occurred immediately before of the actual or target puff (for instance, in a certain embodiments, the two puffs/trials occurred immediately before the puff/trial for which a prediction has to be made), wherein such primary features may include the puffing features (e.g., the puff duration, the average puff flow rate, the puff pressure drop) and the delivered doses for such puffs/trials, and, optionally, the dose which has to be delivered in the actual puff;

3) compute the features vector related to the taken primary features, for instance, generating polynomial and/or interaction features from the primary features (or, in certain embodiments, other functions of the primary features). The so obtained features vector is indicated herein as $x_t$, where, t represents the (next/incoming) target puff (or, in other words, the target puff, for which the time duration has to be predicted). For a non-limiting example, in a certain embodiment, one possible features vector $x_t$ may be expressed as: $x_t=(\Delta D_{t-2}, \Delta D_{t-1}, F_{t-2}, F_{t-1}, m_{t-2}, m_{t-1}, m_t, \Delta D_{t-2} \cdot F_{t-2}, \Delta D_{t-1} \cdot F_{t-1}, \Delta D_{t-2}^2, \Delta D_{t-1}^2, F_{t-2}^2, F_{t-2}^2, m_{t-2}^2, m_{t-1}^2)$, where $\Delta D$ represents the puff duration, F represents the average puff flow rate (i.e., the sum of the puff flow rate occurred during each of the sequential time intervals within the considered puff divided by the number of the time intervals within the puff duration), m represents the vaporized mass (or dose) and the subscript (e.g., t) indicate the puff/trial at which the indicated feature is referred to, for example t represents the actual (target puff), t−1 the puff occurred immediately before, and so on. In certain embodiments, it may be possible to make some tests to create or select the best predicting features (i.e., features engineering, as known in the technical literature and by a person skilled in the art). In other embodiments the features vector $x_t$ may be determined as:

$$x_t=(\Delta D_{t-3}, \Delta D_{t-2}, \Delta D_{t-1} F_{t-3}, F_{t-2}, F_{t-1}, m_{t-3}, m_{t-2}, m_{t-1}, m_t)$$

4) Extend a prediction $\hat{y}_t \in \mathbb{R}$ (e.g., the puff duration, in ms), for the next/incoming puff (also named "puff at the next stage t") using $\hat{y}_t = f(x_t) = w_t \cdot x_t$;

5) take the measured puff features, for instance the duration (in other words, the puff duration effectively occurred for the predicted puff/trial) $y_t$ in the actual puff, and compute a loss function; in a certain embodiment, the following loss function, well known in the technical literature, can be computed:

$$l_t^\varepsilon(w_t; (x_t, y_t)) = \begin{cases} 0 & \text{if } |y_t - \hat{y}_t| \leq \varepsilon \\ |y_t - \hat{y}_t| \leq \varepsilon & \text{otherwise} \end{cases}$$

where, the parameter $\varepsilon$ is the insensitive parameter described above.

6) If the loss function $l_t^\varepsilon$ is greater than zero (i.e., $l_t^\varepsilon > 0$), then:
   a. set the update direction $v_t$ as:

$$v_t = \text{sign}(y_t - w_t \cdot x_t) x_t;$$

b. compute the updating step $\tau_t$:

$$\tau_t = \frac{l_t^\varepsilon(w_t; (x_t, y_t))}{\|v_t\|^2 + \frac{1}{2C}}$$

if the aggressiveness parameter C has not been adopted, then the updating step can be computed as:

$$\tau_t = \frac{l_t^\varepsilon(w_t; (x_t, y_t))}{\|v_t\|^2}$$

c. update the model vector w:

$$w_{t+1} = w_t + \tau_t v_t$$

Adopting the method described above, the vaporizer device acquires the capacity to adapt itself (i.e., some of its internal parameters) for the prediction of the puff duration and/or other puff features, following or tracking the behavior of the user, even if this is time variant.

Figure 8:
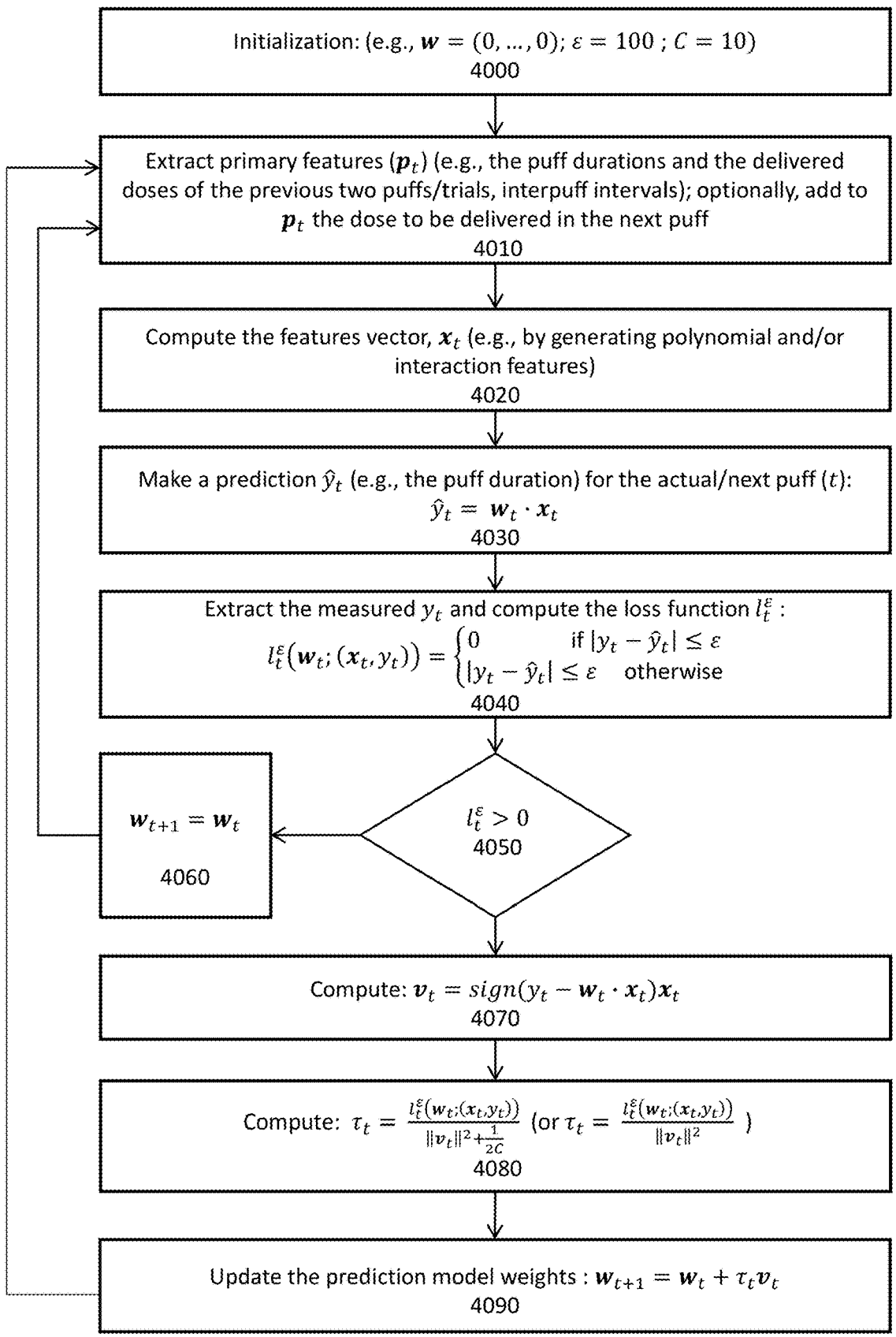
FIG. 8 schematically illustrates one method of predicting the puff duration of the next/incoming puff, as described herein.

For example, FIG. 8 illustrates this method of predicting a puff duration of a target (e.g., the next/incoming) puff. For example, in FIG. 8 the initialization of the main parameters of the algorithm or method may be performed 4000. In a certain embodiment the initialization of the parameters can be set as follows: w=(0, . . . , 0); ε=100; C=10.

In some embodiments, some puffing features may be computed in the puff duration predictor unit on the basis of the data received from the puff sensor and stored in one or more memory registers or devices 4010. In some embodiments, the computed primary features, $p_t$, can be the following: 1) the puff duration of the previous N puffs (e.g., in a certain embodiment N could be equal to 3, or it may be equal to 2, or 1, or 4 or 5 or 10 or a number comprised between 1 and 10, or comprised between 1 and 20, or comprised between 1 and 30, or comprised between 1 and 100), the average flow rate of the previous N puffs (wherein the average flow rate represents the sum of the flow rate measured at each time interval, divided by the number of the time interval during a given puff), the delivered doses relative to the previous N puffs/trials. In some variations other features may be computed, such as the average pressure drop, the time interval between successive puffs, the dose to be delivered in during the target puff.

In some embodiments a features vector (named $x_t$, where the subscription t indicates that the vector is referred to the target (next/incoming) puff/trial) may be computed as a combination (e.g., polynomial and/or interaction) of primary features (or primary features vector $p_t$), as described above 4020. In some variations, different predictions can be made with a variable number of features in order to select the best features to take (such a procedure, called feature engineering, is well known in the art and to a person skilled in the art, and it is optional for some embodiments); or, in some variants, some algorithms for features selections (and/or for features engineering) can be adopted too.

In some embodiments, whenever a puff occurs, its features (and related features, such as the delivered dose, as mentioned) may be computed and collected in the features vector, and a new prediction for the next puff duration can be obtained adopting the model $f(x_t)=w_t \cdot x_t$, obtaining a puff duration prediction, $\hat{y}_t$, 4030.

In some embodiments, after that a target puff has occurred (in other words, after that the puff whose duration has been predicted, has come to the end), its actual (real) duration, $y_t$, may be measured (or computed) and exploited for the computation of the loss function $l_t^\varepsilon$ 4040:

$$l_t^\varepsilon(w_t; (x_t, y_t)) = \begin{cases} 0 & \text{if } |y_t - \hat{y}_t| \le \varepsilon \\ |y_t - \hat{y}_t| \le \varepsilon & \text{otherwise} \end{cases}$$

where, the parameter ε is the insensitive parameter described above.

1) In some embodiments, the computed loss function $l_t^\varepsilon$ may be compared with zero 4050, and if the loss function is greater than zero (i.e., $l_t^\varepsilon > 0$), then:

a. the direction $v_t$ for the gradient (or for the step that the algorithm must follow for updating the model) may be set as (4070):

$$v_t = \text{sign}(y_t - w_t \cdot x_t) x_t;$$

b. an updating step $\tau_t$ may be computed as (4080):

$$\tau_t = \frac{l_t^\varepsilon(w_t; (x_t, y_t))}{\|v_t\|^2 + \frac{1}{2C}}$$

In certain embodiments, where the aggressiveness parameter C is not considered, the updating step can be computed as (4080):

$$\tau_t = \frac{l_t^\varepsilon(w_t; (x_t, y_t))}{\|v_t\|^2}.$$

After such a computation, the model parameters may be updated on the basis of the updating step $\tau_t$ and the direction $v_t$ (4080):

$$w_{t+1} = w_t + \tau_t v_t$$

and restart from the point 4010, for computing new features and make a new prediction.

Otherwise, if the loss function is not greater than zero (i.e., $l_t^\varepsilon < 0$), 4050, then the puff duration predictor unit may maintain the weights of the model as they actually are (e.g., $w_{t+1} = w_t$) 4060 and restart at point 4010 (e.g., extracting and computing new features and make a new prediction).

In some embodiments, other algorithms for the puff duration prediction, and/or some hyperparameters optimization (e.g., C) techniques can be adopted with the invention disclosed herein.

In some embodiments, the features vector may be scaled or normalized (e.g., performing a min-max scaling/rescaling, or a standardization, as known in the machine learning literature and as well known by a person skilled in the art) after that a sufficient number of data points have been collected. For example, in a certain embodiment, the device (such as device 60) may store the minimum and the maximum values of the computed puffing features; after that, the rescaling of the new features (i.e., the features extracted or computed for new previsions) can be computed on the basis of such minimum and maximum stored values.

In some variants, the puff duration predictor unit may be configured to predict the puff volume, and/or other puffing features in place of the puff duration, without departing from the spirit and the scope of the invention.

Dose Computation Unit

A vaporizer device, such as devices 60, 100, 210, may include a dose computation unit, such as within the control unit 110, 210. The Dose Computation Unit 131, may execute the logic described herein to compute sequences (or batches or stages) of doses to be delivered according to any of the methods described herein. In certain embodiments, the dose computation unit is communicatively coupled to one or more of: a dose delivery unit, a puff duration predictor unit, a puff sensor, a heater controller. In certain embodiments, a dose computation unit is communicatively coupled to a dose delivery unit and a timer. In certain embodiments, the dose computation unit includes software (e.g., a software module or control logic) that runs on the processor. The dose computation unit may will then calculate sequences of doses to be delivered.

In some embodiments, the device can include a user interface that allows the user to input the maximum and the minimum values allowed for a dose to be delivered.

In some embodiments, the dose computation unit (or another component of the control unit) can calculate the active material content to be delivered.

In certain embodiments, the dose computation unit is communicatively coupled to a memory unit and stores a plurality of any of the following measurements: delivered/measured (or estimated) doses, cumulative delivered dose, number of puffs/trials, average delivered dose, average delivered dose within a given time period or within a given number of puffs/trials, computed doses, the actual number of delivered doses, the number of positive and negative doses differences, the doses differences, the positions of positive and negative doses differences, or any combination thereof.

In certain embodiments, the dose computation unit is a software module. In certain embodiments, the dose computation unit is a microprocessor. In certain embodiments, the dose computation unit will compute pseudo-random sequences of doses such that, starting from a certain puff/trial, the average positive dose difference is greater in magnitude than the average negative dose difference, subject to the constraint that the average cumulative administered or inhaled dose (i.e., the sum of the doses delivered over successive puffs/trials divided by the number of trials) is kept constant or equal to a predetermined value over time (or over successive puffs/trials) or it is reduced (or it is varied and set as desired), and subject to the constraint that each dose can take only values within a settable or predetermined range, and/or subject to the constraint that a dose difference can assume values within predetermined ranges, wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

In certain embodiments, the average dose difference has to be greater in magnitude (i.e., the absolute values have to be compared) than the average negative dose difference of about a 5% factor. In certain embodiments, the magnitude of the average dose difference has to be greater than the magnitude of the average negative dose difference of about a 10% factor. In certain embodiments, the magnitude of the average dose difference has to be greater than the magnitude of the average negative dose difference of about a 15% factor. In certain embodiments, the magnitude of the average dose difference has to be greater than the magnitude of the average negative dose difference of about a 20% factor. In certain embodiments, the magnitude of the average dose difference has to be greater than the magnitude of the average negative dose difference of about a 25% factor. In certain embodiments, the magnitude of the average dose difference has to be greater than the magnitude of the average negative dose difference of about a 30% factor. In certain embodiments, the magnitude of the average dose difference has to be greater than the magnitude of the average negative dose difference of about a 35% factor. In certain embodiments, the magnitude of the average dose difference has to be greater than the magnitude of the average negative dose difference of about a 40% factor. In certain embodiments, the magnitude of the average dose difference has to be greater than the magnitude of the average negative dose difference of a factor greater than a 40% (e.g., of a 50% factor, of a 200% factor, and so on).

In certain embodiments, the magnitude of the average positive dose and the magnitude of the average negative dose and their difference can be considered or computed for all the puffs/trials (in other words, all the above mentioned quantities can be computed considering all the trials as they occur). In certain embodiments, the magnitude of the average positive dose and the magnitude of the average negative dose and their difference can be considered or computed within sequences (or batches) of a predetermined number of puffs/trials (for example such a number of puffs/trials may be equal to the number of trials of a stage). In certain embodiments, said number of puffs/trials is to within about 100 (e.g., within about 99, within about 98, within about 97, within about 96, etc.). In certain embodiments, said number of puffs/trials is to within about 1000.

In certain embodiments, the dose computation unit may compute a predetermined number of sequential doses (e.g., 10 or 12, or 15, etc.) at a time, for example whenever a start signal occurs; such a signal may be determined by an user, or, for example, indirectly, whenever a tobacco stick or pod is inserted or changed within the vaporizer (e.g., in a THS device).

In certain embodiments, the dose computation unit is adjustable, by the user, or by a software, or remotely, and allows to set or change the maximum and the minimum values that each dose can take and/or the average dose which can be delivered. In certain embodiments the maximum and minimum values allowed for each dose (or the average dose to be delivered within successive puffs/trials), and/or for each dose difference, may be expressed in mg of TPM, or in mg of an active ingredient (e.g., nicotine, cannabinoid, THC, etc.). In certain embodiments, the minimum and maximum values allowed for each dose and/or for each dose difference may be expressed in µg (micrograms, also expressed as "ug"). In certain embodiments the minimum value allowed for each delivered dose of nicotine (or of an active ingredient) may be about 0.03 mg. In certain embodiments the minimum value allowed for each delivered dose of nicotine (or of an active ingredient) may be about 0.04 mg. In certain embodiments the minimum value allowed for each delivered dose of nicotine (or of an active ingredient) may be about 0.05 mg. In certain embodiments the minimum value allowed for each delivered dose of nicotine (or of an active ingredient) may be about 0.06 mg. In certain embodiments the minimum value allowed for each delivered dose of nicotine (or of an active ingredient) may be about 0.07 mg. In certain embodiments the minimum value allowed for each delivered dose of nicotine (or of an active ingredient) may be about 0.08 mg. In certain embodiments the minimum value allowed for each delivered dose of nicotine (or of an active ingredient) may be greater than 0.08 mg.

In certain embodiments the maximum value allowed for each delivered dose of nicotine (or of an active ingredient) may be about 0.05 mg. In certain embodiments the maximum value allowed for each delivered dose of nicotine (or of an active ingredient) may be about 0.06 mg. In certain embodiments the maximum value allowed for each delivered dose of nicotine (or of an active ingredient) may be about 0.07 mg. In certain embodiments the maximum value allowed for each delivered dose of nicotine (or of an active ingredient) may be about 0.08 mg. In certain embodiments the maximum value allowed for each delivered dose of nicotine (or of an active ingredient) may be about 0.09 mg. In certain embodiments the maximum value allowed for each delivered dose of nicotine (or of an active ingredient) may be about 0.1 mg. In certain embodiments the maximum value allowed for each delivered dose of nicotine (or of an active ingredient) may be about 0.11 mg. In certain embodiments the maximum value allowed for each delivered dose of nicotine (or of an active ingredient) may be about 0.12 mg. In certain embodiments the maximum value allowed for each delivered dose of nicotine (or of an active ingredient) may be about 0.13 mg. In certain embodiments the maximum value allowed for each delivered dose of nicotine (or of an active ingredient) may be about 0.14 mg. In certain embodiments the maximum value allowed for each delivered dose of nicotine (or of an active ingredient) may be about 0.15 mg. In certain embodiments the maximum value allowed for each delivered dose of nicotine (or of an active ingredient) may be greater than 0.15 mg.

In certain embodiments, the average cumulative dose can be set by the user or remotely, and/or it can be set to be a varying quantity (such as over successive puffs/trials or over successive stages e.g., by a custom algorithm) in the dose computation unit. The average dose to be delivered over sequential puffs/trials, may be expressed in mg of TPM or in mg of an active ingredient or in ug (micrograms).

In certain embodiments, the dose computation unit is user adjustable, so that the vaporizer device will vaporize a target amount of material in a plurality of puffs.

In real time, the dose computation unit can take a device's data and use it to compute doses to be delivered in mg.

In certain embodiments, the dose computation unit is a software component associated with the processor.

In a certain embodiment, the dose computation unit is user adjustable using a button. In a certain embodiment, the dose computation unit is user adjustable using a dial. In a certain embodiment, the dose computation unit is user adjustable using a capacitive interface. In a certain embodiment, the dose computation unit is user adjustable using a wireless connection. In a certain embodiment, the dose computation unit is user adjustable using voice communication.

In a certain embodiment, the type of vaporizable material is adjustable. In a certain embodiment the type of vaporizable material that is adjustable is nicotine. In a certain embodiment, the type of vaporizable material that is adjustable is a *Cannabis*. In a certain embodiment, the type of vaporizable material that is adjustable is a cannabinoid. In a certain embodiment, the type of vaporizable material that is adjustable is a medicinal compound. In a certain embodiment, the type of vaporizable material that is adjustable is a botanical. In a certain embodiment, the type of vaporizable material that is adjustable is a nutraceutical. In some embodiments, the type of material that is adjustable is formulation specific (e.g., a percent compound dissolved in a specific solvent).

Puff Sensor

As described above, the vaporizer apparatuses described herein may include a puff sensor. In certain embodiments, the puff sensor measures the initiation of the users puff and the puff flow rate. In certain embodiments, the puff sensor measures the cessation of the users puff. In certain embodiments, the puff sensor measures the duration of the users puff. In certain embodiments, the puff sensor measures the velocity and amount of air traveling through the electronic vaporizer device or flow rate. In certain embodiments, the puff sensor is a button that is pressed upon initiation of a user's puff. In certain embodiments, the puff sensor is a pressure sensor. In certain embodiments, the pressure sensor is a venturi meter. In certain embodiments, the pressure sensor is an orifice plate. In certain embodiments, the pressure sensor is a Dall tube. In certain embodiments, the pressure sensor is a pitot-static tube. In certain embodiments, the pressure sensor is a multi-hole pressure probe. In certain embodiments, the pressure sensor is a cone meter. In certain embodiments, the puff sensor comprises a button that is pressed by the user to initiate a puff. In certain embodiments, the puff sensor is a flow meter.

In certain embodiments, the flow meter is a turbine flow meter. In certain embodiments, the puff sensor is communicatively coupled to the control unit 110. In certain embodiments, the puff sensor is communicatively coupled to a heater controller and/or to a puff duration predictor unit and/or to a dose delivery unit. In certain embodiments, the puff sensor is configured to measure a puff initiated by the user. In certain embodiments, the puff sensor is configured to measure a puff initiated by an analytical smoking machine. In certain embodiments, the puff sensor may be an electro-mechanical device. In certain embodiments, the puff sensor may be any of a mechanical device, an optical device, an optomechanical device, a micro electro-mechanical systems (MEMS) based sensor and an acoustic sensor.

The puff sensor may include software and hardware for measuring the puff flow rate and other puff features that may be integral with (or separate from) any of the controller and/or processors described herein.

In any of the apparatuses described herein, the electronic vaporizer device utilizing the methods disclosed herein, such as devices 60, 100, 210, may include a memory. In certain embodiments, the memory (e.g., memory unit) is hardware that is communicatively coupled to the puff sensor. In certain embodiments, the memory is internal to the electronic vaporizer device. In certain embodiments, the memory is external to the electronic vaporizer device. In certain embodiments, the memory unit is a solid-state memory. In certain embodiments, the memory unit is a hard disk.

In any of the electronic vaporizer device described herein, such as devices 60, 100, 210, the apparatus may include a processor. In certain embodiments, the processor may include software, firmware and/or hardware that executes the controlling logic of the device. In certain embodiments, the processor is communicatively coupled to the puff sensor. In certain embodiments, the processor is communicatively coupled to the memory unit.

Puff Duration Predictor Unit

A vaporizer device, such as devices 60, 100, 210, may include a Puff Duration Predictor Unit, such as within the control unit 110, 210. The Puff Duration Predictor Unit 121, may execute the logic described herein to calculate puffing topography features (such as the puff duration, the average flow rate, the pressure drop, etc.) and to predict the puff duration of future (e.g., next or incoming) puff(s)/trial(s). In certain embodiments, the puff duration predictor unit is communicatively coupled to one or more of: a dose computation unit, a puff sensor, a dose delivery unit. In certain embodiments, a puff duration predictor unit is communicatively coupled to a dose computation unit, a dose delivery unit, a puff sensor and a timer. In certain embodiments, the puff duration predictor unit includes software (e.g., a software module or control logic) that runs on the processor. The puff duration predictor unit may will then calculate puffing features and predict/compute the puff duration of the next puff based on the puffing features of the puffs occurred immediately before, the related doses delivered during such puffs and optionally based on the dose which has to be delivered during the next puff.

The puff duration predictor unit may integrate puff flow rate readings from the puff sensor, puff duration from the puff sensor and the timer, values of the delivered doses during some of the puffs occurred immediately before the target puff, the dose to be delivered during the target puff and compute some puffing features and predict the puff duration of the target puff (i.e., the next or incoming puff).

The puff duration predictor unit will then predict the puff duration of the next puff as described herein.

In certain embodiments, the puff duration predictor unit is communicatively coupled to a memory unit and stores a plurality of any of the following measurements: flow rate readings, puff duration readings, computed puffing behavioral features (such as the pressure drop, the interval time between sequential puffs, etc.) or any combination thereof.

In certain embodiments, the puff duration predictor unit is a software module. In certain embodiments, the puff duration predictor unit is a microprocessor.

In certain embodiments, the puff duration predictor unit transmits data to the dose delivery unit, so that the dose delivery unit may compute the power values to deliver to the heater to vaporize a computed dose. In certain embodiments, the puff duration predictor unit is a firmware module. In certain embodiments, the puff duration predictor unit is a hardware element.

In any of the apparatuses described herein, the electronic vaporizer device utilizing the method of predicting the puff duration of the next or incoming puff(s), such as devices 60, 100, 210, may include a memory. In certain embodiments, the memory (e.g., memory unit) is hardware that is communicatively coupled to the puff duration predictor unit. In certain embodiments, the memory is internal to the electronic vaporizer device. In certain embodiments, the memory is external to the electronic vaporizer device. In certain embodiments, the memory is configured to store a plurality of any of flow rate, pressure, time, puff duration, puff frequency measurements and combinations thereof. In certain embodiments, the memory unit is a solid state memory. In certain embodiments, the memory unit is a hard disk.

In any of the electronic vaporizer device described herein, such as devices 60, 100, 210, the apparatus may include a processor. In certain embodiments, the processor may include software, firmware and/or hardware that executes the controlling logic of the device. In certain embodiments, the processor is communicatively coupled to the puff duration predictor unit. In certain embodiments, the puff duration predictor unit and the processor are the same element. In certain embodiments, the processor is communicatively coupled to the memory unit.

Dose Delivery Unit

A vaporizer device, such as devices 60, 100, 210, may include a Dose Delivery Unit, such as within the control unit 110, 210. The Dose Delivery Unit 109, may execute the logic described herein to compute sequences of partial doses to be delivered during each of the partial dose time intervals within a time period (or puff duration); to compute and deliver the values of power to be delivered to the heater (through the heater controller which is communicatively coupled to the dose delivery unit) for vaporizing the partial doses, and to measure/estimate the delivered doses within the vaporizer device, according to any of the methods described herein. In certain embodiments, the dose delivery unit is communicatively coupled to one or more of: a dose computation unit, a puff duration predictor unit, a puff sensor, a heater controller, a temperature sensor. In certain embodiments, a dose delivery unit is communicatively coupled to a dose computation unit, a puff duration predictor unit, a puff sensor, a temperature sensor, a heater controller and a timer.

In certain embodiments, the dose delivery unit includes software (e.g., a software module or control logic) that runs on the processor. The dose delivery unit may will then calculate sequences of partial doses to be delivered, power values to be applied to the heater, and estimate the delivered doses.

The dose delivery unit may integrate power readings from the heater controller, temperature readings from the temperature sensor, and puff flow rate, puff duration or puff frequency readings from the puff sensor and timer, and/or from the puff duration predictor unit and a predicted puff duration from the puff duration predictor unit.

The dose delivery unit will then calculate the partial doses to be delivered during each of the sequential partial time intervals which form the puff duration, and compute the power values to apply to the heater for vaporizing the partial doses, and compute/estimate how much vapor has been actually vaporized from a vaporizable material.

In some embodiments, the dose delivery unit of each device can be calibrated separately. In some embodiments, a dose delivery unit calibration can be set based upon a known vaporization material. In some embodiments, the device can include a user interface that allows the user to input the material being vaporized, which in turn sets the constants $\theta_1$, $\theta_2$, $\theta_3$ for equation 2 and/or the function fit curve or look-up table (or constants for equation 4 or constants for whatever function of power, flow rate, temperature and vaporized mass).

In some embodiments, the dose delivery unit (or another component of the control unit) can calculate the active material content based upon the TPM. The TPM to active material content can be correlated based on the composition of the organic materials loaded into the electronic vaporizer device. For example, for an organic material, that contains a percentage of 20-25% active material, would correlate to a TPM, mg, containing said percentage of active material. In some cases, it may be reasonable to assume total conversion (aerosolization) of the active material. For example, for organic material selected from cannabis extract, where the organic material is a cannabis extract containing 25% cannabidiol (CBD), then the TPM, mg, correlated to said 25% CBD, means the TPM, mg has the percentage of said active compound, preferably assuming total conversion (aerosolization) of the active material.

In certain embodiments, the dose delivery unit is user adjustable so that the device can be disable for a period of time after a target amount of material has been vaporized. The dose delivery may be user adjustable so that the device can engage an alert after a target amount of material has been vaporized. In certain embodiments, the dose delivery unit engages an alert when the amount of vaporizable material in the vaporizer device falls below a preset threshold. In certain embodiments, the dose delivery unit is communicatively coupled to a memory unit and stores a plurality of any of the following measurements: power, temperature, puff duration readings, puff flow rate readings, puffing behavioral features (such as the pressure drop, the interval time between sequential puffs, etc.) or any combination thereof. In certain embodiments, the dose delivery unit will calculate a cumulative amount of vaporizable material that is vaporized. For example, if a user does not fully vaporize the preset limit in one puff the dose delivery unit will keep track of the amount of vaporizable material vaporized over a plurality of puffs. In certain embodiments, the dose delivery unit is a software module. In certain embodiments, the dose delivery unit is a microprocessor. In certain embodiments, the dose delivery unit will generate a puff profile that tracks power, temperature, pressure or flow rate or a combination thereof over time.

In certain embodiments, the accuracy of the delivered and measured TPM vaporized from a dose delivery unit is at least ±25% of a computed or predicted value. In certain embodiments, the accuracy of the computed, delivered or measured TPM vaporized from a dose delivery unit is at least ±20% of a predicted value. In certain embodiments, the accuracy of the computed or measured or estimated TPM vaporized from a dose delivery unit is at least ±15% of a predicted or computed value. In certain embodiments, the accuracy of the computed and/or estimated TPM vaporized from a dose delivery unit is at least ±10% of a predicted or computed value. In certain embodiments, the accuracy of the measured or estimated TPM vaporized from a dose delivery unit is at least ±5% of a predicted or computed value. In certain embodiments, the accuracy of the measured or estimated TPM vaporized from a dose delivery unit is at least ±1% of a predicted or computed value. In certain embodiments, the dose delivery unit is a software component associated with the processor.

In a certain embodiment, the dose delivery unit integrates readings from the puff sensor, temperature sensor, heating element controller, dose delivery unit, and timer to create profiles of the readings. A power profile is the change in power delivery over time. A temperature profile is the change in temperature over time.

In a certain embodiment, the profile is measured from the initiation of the puff, as measured by the puff sensor to the cessation of the puff, as measured by the puff sensor. In a certain embodiment, the dose delivery unit stores a plurality of profiles in a memory unit.

In real time, the dose delivery unit can take a device's data and use it to calculate cumulative TPM in mg. For example, when the TPM reaches 40 mg, the human subject can be prompted to stop puffing, or the heating element can be adjusted or turned off. The constants can be modified to account for different pods and different liquids.

In certain embodiments, the dose delivery unit, receiving data from the dose computation unit, transmits instructions to the heater controller in order to delivered computed (or predetermined or loaded in memory) doses of TPM or drug or substance (including active ingredients).

In some variants, such instructions can disable the heating element when the computed dose has been delivered.

In certain embodiments, the dose delivery unit is a firmware module. In certain embodiments, the dose delivery unit is a hardware element.

In certain embodiments, the dose delivery unit will relay instructions to the heating element controller to allow a user to vaporize a target amount of TPM in a single puff.

In certain embodiments, the dose delivery unit will prompt the heating element controller to allow a user to vaporize a target amount of TPM in a plurality of puffs.

In certain embodiments, the heating element controller is communicatively coupled to the dose delivery unit. In certain embodiments, the dose delivery unit inactivates the heating element. In certain embodiments, the dose delivery unit modifies the amount of power delivered to the heating element. In certain embodiments, the dose delivery unit turns the electronic vaporizer device off. In certain embodiments, the user can override the dose delivery unit to restore proper operation of the vaporizer device.

In any of the apparatuses described herein, the electronic vaporizer device utilizing the method of computing, delivering and determining the amount of vapor or dose produced (and therefore delivered to a user), such as devices 60, 100, 210, may include a memory. In certain embodiments, the memory (e.g., memory unit) is hardware that is communicatively coupled to the dose delivery unit. In certain embodiments, the memory is internal to the electronic vaporizer device. In certain embodiments, the memory is external to the electronic vaporizer device. In certain embodiments, the memory is configured to store a plurality of any of temperature, power, flow rate, pressure, time, puff duration, puff frequency measurements and combinations thereof. In certain embodiments, the memory unit is a solid-state memory. In certain embodiments, the memory unit is a hard disk.

In any of the electronic vaporizer device described herein, such as devices 60, 100, 210, the apparatus may include a processor. In certain embodiments, the processor may include software, firmware and/or hardware that executes the controlling logic of the device. In certain embodiments, the processor is communicatively coupled to the dose delivery unit. In certain embodiments, the dose delivery unit and the processor are the same element. In certain embodiments, the processor is communicatively coupled to an user interface. In certain embodiments, the processor is communicatively coupled to the memory unit.

As described above, the electronic vaporizer devices described herein may include a power source. Such as power source 230. In certain embodiments, the power source is removable. In certain embodiments, the power source is a battery. In certain embodiments, the power source is a rechargeable battery. In certain embodiments, the rechargeable battery is a lithium ion battery. In certain embodiments, the rechargeable battery is compatible with a USB charging cable. In certain embodiments, the electronic vaporizer device with a rechargeable battery is compatible with a micro USB charging cable. In certain embodiments, the rechargeable battery is compatible with a charging cradle. A charging cradle is any physical device capable of supporting the electronic vaporizer device while charging; the cradle can either be integral to the electronic vaporizer device or separate from the electronic vaporizer device. In certain embodiments, the charging cradle has charging contacts, configured to mate to contacts on the electronic vaporizer device. In certain embodiments, the charging cradle charges the electronic vaporizer device using induction technology. In certain embodiments, the charging cradle is an induction charging mat.

The power source may be configured to deliver power to the heating element, and may be regulated by the heater controller also based on instructions transmitted from the dose delivery unit to the heater controller. The heater controller may therefore receive charge/power level input from the power source and may adjust its output accordingly. In certain embodiments, the power source is configured to deliver an adjustable amount of power. In certain embodiments, the amount of power is adjustable by the user. In certain embodiments, the amount of power is adjusted by the dose delivery unit.

As mentioned, the power source may be communicatively coupled to the heater controller. In certain embodiments, the power source is configured to deliver an adjustable amount of power and is controlled by the dose delivery unit.

In certain embodiments, the power source delivers between 1 and 100 watts of power. In certain embodiments, the power source delivers between 1 and 50 watts of power. In certain embodiments, the power source delivers between 1 and 20 watts of power. In certain embodiments, the power source delivers between 1 and 10 watts of power. In certain embodiments, the power source delivers between 1 and 8 watts of power. In certain embodiments, the power source delivers between 2 and 10 watts of power. In certain embodiments, the power source delivers between 10 and 100 watts of power. In certain embodiments, the power source delivers between 10 and 50 watts of power. In certain embodiments, the power source delivers between 10 and 20 watts of power. In certain embodiments, the power source delivers about 4 watts of power. In certain embodiments, the power source delivers about 4.5 watts of power. In certain embodiments, the power source delivers about 5 watts of power. In certain embodiments, the power source delivers about 5.5 watts of power. In certain embodiments, the power source delivers about 6 watts of power. In certain embodiments, the power source delivers about 6.5 watts of power. In certain embodiments, the power source delivers about 7 watts of power. In certain embodiments, the power source delivers about 7.5 watts of power. In certain embodiments, the power source delivers about 8 watts of power. In certain embodiments, the power source delivers about 8.5 watts of power. In certain embodiments, the power source delivers about 9 watts of power. In certain embodiments, the power source delivers about 10 watts of power. In certain embodiments, the power source delivers about 20 watts of power. In certain embodiments, the power source delivers about 30 watts of power. In certain embodiments, the power source delivers about 40 watts of power. In certain embodiments, the power source delivers about 10 watts of power. In certain embodiments, the power source delivers about 50 watts of power. In certain embodiments, the power source delivers about 60 watts of power. In certain embodiments, the power source delivers about 70 watts of power. In certain embodiments, the power source delivers about 80 watts of power. In certain embodiments, the power source delivers about 90 watts of power. In certain embodiments, the power source delivers about 100 watts of power.

The power applied may alternatively or additionally (and equivalently) be expressed in joules. For example, in certain embodiments, the power source delivers between 1 and 1000 joules to the heater. In certain embodiments, the power source delivers between 1 and 500 joules to the heater. In certain embodiments, the power source delivers between 1 and 100 joules to the heater. In certain embodiments, the power source delivers between 1 and 50 joules to the heater. In certain embodiments, the power source delivers between 1 and 25 joules to the heater. In certain embodiments, the power source delivers between 5 and 25 joules to the heater. In certain embodiments, the power source delivers between 1 and 20 joules to the heater. In certain embodiments, the power source delivers between 5 and 20 joules to the heater. In certain embodiments, the power source delivers between 10 and 500 joules to the heater. In certain embodiments, the power source delivers between 10 and 100 joules to the heater. In certain embodiments, the power source delivers between 10 and 50 joules to the heater. In certain embodiments, the power source delivers between 10 and 20 joules to the heater.

As described above, any of the vaporizer apparatuses described herein may include a heater (heating element). In certain embodiments, the heater is a resistive heating element. In certain embodiments, the heating element forms a coil. In certain embodiments, the coil is wrapped around a wick. In certain embodiments, the wick is in contact with a vaporizable material. In certain embodiments, the wick projects into the vaporizable material. In certain embodiments, the heating element heats the vaporizable material to between 40 and 1000 degrees Celsius. In certain embodiments, the heating element heats the vaporizable material to between 100 and 900 degrees Celsius. In certain embodiments, the heating element heats the vaporizable material to between 100 and 800 degrees Celsius. In certain embodiments, the heating element heats the vaporizable material to between 100 and 700 degrees Celsius. In certain embodiments, the heating element heats the vaporizable material to between 100 and 600 degrees Celsius. In certain embodiments, the heating element heats the vaporizable material to between 100 and 500 degrees Celsius. In certain embodiments, the heating element heats the vaporizable material to between 100 and 400 degrees Celsius. In certain embodiments, the heating element heats the vaporizable material to between 100 and 300 degrees Celsius. In certain embodiments, the heating element heats the vaporizable material to between 180 and 250 degrees Celsius. In certain embodiments, the heating element heats the vaporizable material to between 100 degrees Celsius and 200 degrees Celsius. In certain embodiments, the heating element heats the vaporizable material to between 125 degrees Celsius and 175 degrees Celsius. In certain embodiments, the heating element heats the vaporizable material to about 150 degrees Celsius. In certain embodiments, the heating element heats the vaporizable material to between 200 and 300 degrees Celsius. In certain embodiments, the heating element heats the vaporizable material to between 225 and 275 degrees Celsius. In certain embodiments, the heating element heats the vaporizable material to about 250 degrees Celsius. In certain embodiments, the heating element heats the vaporizable material to between 300 and 400 degrees Celsius. In certain embodiments, the heating element heats the vaporizable material to between 325 and 375 degrees Celsius. In certain embodiments, the heating element heats the vaporizable material to about 350 degrees Celsius. In certain embodiments, the heating element heats the vaporizable material to between 400 and 500 degrees Celsius. In certain embodiments, the heating element heats the vaporizable material to between 500 and 600 degrees Celsius. In certain embodiments, the heating element heats the vaporizable material to between 600 and 700 degrees Celsius. In certain embodiments, the heating element heats the vaporizable material to between 700 and 800 degrees Celsius. In certain embodiments, the heating element heats the vaporizable material to between 800 and 900 degrees Celsius. In certain embodiments, the heating element heats the vaporizable material to between 900 and 1000 degrees Celsius.

In one embodiment, the heating element is housed within a vaporization chamber surrounded by vaporization chamber walls.

The vaporization chamber is also referred to as the atomizer. In some embodiments, the vaporization chamber walls can be constructed of any material capable of withstanding repeated heating to the operating temperature of the vaporizer device. In some embodiments, the vaporization chamber walls can be constructed of any material capable of withstanding repeated heating to 300 degrees Celsius. The vaporization chamber possesses an air inlet, to allow the entrance of air to the atomizer, and an air outlet, to allow vapor to escape to the user. Vaporizable material is introduced to the atomizer by a wick, which is in fluid communication with a vaporizable material. The vaporizable material can be stored in a tank integral to the electronic vaporizer device or in a removable tank (pod), configured to be detached from the vaporizer device after it is depleted. In an alternative embodiment, the heater element is in an oven configuration, wherein the heating element surrounds a chamber with stainless steel walls, and heats a vaporizable material, placed within the chamber, by conduction. In an oven configuration, the inside of the oven can be exposed to the outside by removal of an oven lid, which allows loading of a vaporizable material. The oven can further contain an outlet that allows vapor to escape to the user.

In any of the vaporizer devices described herein, the apparatus may include a heater controller (e.g., a heating element controller). In certain embodiments, the heater controller operates the heating element. In certain embodiments, the heater controller switches the heater on and off, and/or switches the heater on and off in a rapid "pulsed" fashion. In certain embodiments, the heater controller is configured to detect and/or control the power delivered from the power source. In certain embodiments, the heater controller is configured to detect and/or control the voltage delivered from the power source. In certain embodiments, the heater controller is configured to detect and/or control the current delivered from the power source. In certain embodiments, the heater controller is configured to detect and/or control the power, voltage and/or current delivered, or any combination thereof from the power source, on the basis of the instructions transmitted by the dose delivery unit. In certain embodiments, the heater controller is connected in series with the power source and the heater. In certain embodiments, the heater controller is connected to the power source in parallel with the heater. In certain embodiments, the heater controller is configured to detect and/or control the power delivered from the power source in Watts. In certain embodiments, the heater controller is configured to detect and/or control the voltage delivered from the power source in Volts. In certain embodiments, the heater controller is configured to detect and/or control the current delivered from the power source in Amps. In certain embodiments, the heater controller is communicatively coupled to the dose delivery unit.

In certain embodiments, the heater controller is configured to regulate the operation of the heater. In certain embodiments, the heater controller is configured to regulate the temperature of the heater. In certain embodiments, the heater controller is configured to regulate the Voltage delivered to the heater by the power source. In certain embodiments, the heater controller is configured to regulate the current delivered to the heating element by the power source. In certain embodiments, the heater controller is configured to regulate the wattage delivered to the heater by the power source. In certain embodiments, the heater controller is configured to regulate the temperature of the heater by regulating power delivered from the power source. In certain elements, the heating element controller is communicatively coupled to the processor. In certain embodiments, the heater controller is configured to receive instructions from the processor and/or from the dose delivery unit.

As discussed above, the heater controller may use control logic (e.g., a PID loop) including one or more inputs such as the temperature, e.g., determined using the coefficient of resistance or TCR of the heater. Thus, in determining the power to be applied to deliver a partial dose (e.g., partial doses of a puff), the apparatus may advantageously use just electrical values (resistance and power values) from the controller, once calibrated with the appropriate constants (which may be analytically determined as mentioned above, or may be assumed/ignored).

Timer

In certain embodiments, the electronic vaporizer device utilizing the method of computing, delivering, controlling and determining the amount of vapor delivered to the user (and utilizing the related method for predicting the puff duration) described herein, such as device 60, includes a timer. In a certain embodiment, the timer is communicatively coupled to the temperature sensor. In certain embodiments, the timer is communicatively coupled to the puff sensor. In certain embodiments, the timer measures a puff duration. In certain embodiments, the timer measures a puff frequency. In certain embodiments, the timer is communicatively coupled to one or more of the following units: dose delivery unit, puff duration predictor unit, dose computation unit. In certain embodiments, the timer is communicatively coupled to the puff sensor, the dose delivery unit, the puff duration predictor unit. In some instances, a puff duration can range from about 0.1 seconds to about 10 seconds (or from about 100 ms to about 10.000 ms). In some instances, a puff duration can range from about 1 second to about 5 seconds (or from about 1000 ms to about 5000 ms). In some instances, a puff duration can range from about 1 second to about 4 seconds (or from about 1000 ms to about 4000 ms). In some instances, a puff duration can range from about 1 second to about 3 seconds (or from about 1000 ms to about 3000 ms). In some instances, a puff duration can range from about 1 second to about 2 seconds (or from about 1000 ms to about 2000 ms). In certain embodiments, the accuracy of a measurement of the puff duration is within about ±0.02 seconds (or within about ±20 ms). In certain embodiments, the accuracy of a measurement of the puff duration is within about ±0.03 seconds (or within about ±30 ms). In certain embodiments, the accuracy of a measurement of the puff duration is within about ±0.04 seconds (or within about ±40 ms). In certain embodiments, the accuracy of a measurement of the puff duration is within about ±0.05 seconds (or within about ±50 ms). In certain embodiments, the accuracy of a measurement of the puff duration is within about ±0.1 seconds (or within about ±100 ms). In certain embodiments, the accuracy of a measurement of the puff duration is within about ±0.2 seconds (or within about ±200 ms). In certain embodiments, the accuracy of a measurement of the puff duration is within about ±0.3 seconds (or within about ±300 ms). In certain embodiments, the accuracy of a measurement of the puff duration is within about ±0.4 seconds (or within about ±400 ms). In certain embodiments, the accuracy of a measurement of the puff duration is within about ±0.5 seconds (or within about ±500 ms).

Pre-Heating

In some variations, the heated reservoir may be heated. In certain embodiments, the electronic vaporizer device utilizing the methods disclosed herein, such as device 60, includes a heat block reservoir (or heat reservoir or heat block).

Heating the reservoir may allow for a more controlled initial state, which may enhance the predictability and the stability of the dose. In some variations heating the reservoir may be unnecessary. Alternatively, just the portion of the vaporizable material feeding into the vaporizing region (e.g., wick) may be heated.

Smoking vaporizable organic formulations that may be thick (non-flowing) or non-liquid with electronic vaporizer devices can pose a challenge. However, there remains an unmet need of vaporizing organic formulations that are otherwise thick (non-flowing) liquids or non-liquids, that include, but are not limited to, for example, *Cannabis* extracts. In certain embodiments, the heat reservoir is distinct form the heating element. In certain embodiments, the heat reservoir is fluidly coupled to the heater element. In certain embodiments, the heat reservoir is constructed of stainless steel. In certain embodiments, the heat reservoir is constructed of high temperature plastic. In certain embodiments, the heat reservoir pre heats a viscous, semi-solid or solid composition, before vaporization with the heating element.

In certain embodiments, the heat reservoir preheats a vaporizable material to between 40 degrees Celsius and 100 degrees Celsius. In certain embodiments, the heat reservoir preheats a vaporizable material to between 40 degrees Celsius and 80 degrees Celsius. In certain embodiments, the heat reservoir preheats a vaporizable material to between 40 degrees Celsius and 60 degrees Celsius. In certain embodiments, the heat reservoir preheats a vaporizable material to about 50 degrees Celsius. In certain embodiments, the heat reservoir preheats a vaporizable material to between 50 degrees Celsius and 100 degrees Celsius. In certain embodiments, the heat reservoir preheats a vaporizable material to between 60 degrees Celsius and 100 degrees Celsius. In certain embodiments, the heat reservoir preheats a vaporizable material to between 70 degrees Celsius and 100 degrees Celsius. In certain embodiments, the heat reservoir preheats a vaporizable material to between 80 degrees Celsius and 100 degrees Celsius. In certain embodiments, the heat reservoir preheats a vaporizable material to between 90 degrees Celsius and 100 degrees Celsius. In certain embodiments, the heat reservoir preheats a vaporizable material to between 90 degrees Celsius and 250 degrees Celsius.

In certain embodiments, the heat block is configured to warm material that exhibits a viscosity between 50 and 1000 Centipoise. In certain embodiments, the heat block is configured to warm material that exhibits a viscosity between 1,000 and 5,000 Centipoise. In certain embodiments, the heat block is configured to warm material that exhibits a viscosity between 5,000 and 50,000 Centipoise. In certain embodiments, the heat block is configured to warm material that exhibits a viscosity above 5,000 Centipoise (or above 10,000 Centipoise, above 20,000 Centipoise, above 30,000 Centipoise, above 40,000 Centipoise, etc.).

Vaporizable Material

As described above, the vaporizer apparatuses described herein may be used with (and may include or be configured specifically for) any appropriate vaporizable material. In certain embodiments, the vaporizable material is an organic material. In certain embodiments, vaporizable material is a liquid, viscous liquid, solid, wax or loose-leaf material or a combination thereof.

In certain embodiments, the vaporizable material is a tobacco-based material. In certain embodiments, the vaporizable material is a *Cannabis* based material. In certain embodiments, the vaporizable material is a botanical. In certain embodiments, the vaporizable material is nicotine, a nicotine derivative or a nicotine salt. In certain embodiments, the vaporizable material is a nutraceutical. In certain embodiments, the vaporizable material contains a cannabinoid. In certain embodiments, the vaporizable material is a medicinal compound.

In certain embodiments, the vaporizable material exhibits a viscosity between 1 and 50 Centipoise. In certain embodiments, the vaporizable material exhibits a viscosity between 50 and 1,000 Centipoise. In certain embodiments, the vaporizable material exhibits a viscosity between 1,000 and 5,000 Centipoise. In certain embodiments, the vaporizable material exhibits a viscosity between 5,000 and 10,000 Centipoise. In certain embodiments, the vaporizable material exhibits a viscosity above 10,000 Centipoise.

In certain embodiments, the vaporizable material contains nicotine. In certain embodiments, the vaporizable material contains a nicotine derivative. In certain embodiments, the nicotine derivative is an acid salt of nicotine. In certain embodiments, the acid salt of nicotine comprises an organic acid. In certain embodiments, the acid salt of nicotine does not comprise an inorganic acid. In certain embodiments, the nicotine derivative is cotinine. In certain embodiments, the nicotine derivative is norcotinine. In certain embodiments, the nicotine derivative is nornicotine. In certain embodiments, the nicotine derivative is nicotine N-oxide. In certain embodiments, the nicotine derivative is cotinine N-oxide. In certain embodiments, the nicotine derivative is 3-hydroxycotinine. In certain embodiments, the nicotine derivative is 5-hydroxycotinine.

In certain embodiments, the vaporizable material is a formulation of nicotine, nicotine derivatives, or a nicotine salt.

Nicotine salt formulations are formed by the addition of a suitable acid to nicotine or a derivative thereof, including organic or inorganic acids. In some formulations, suitable organic acids are carboxylic acids. Examples of organic carboxylic acids are monocarboxylic acids, dicarboxylic acids (organic acid containing two carboxylic acid groups), carboxylic acids containing an aromatic group such as benzoic acids, hydroxycarboxylic acids, heterocyclic carboxylic acids, terpenoid acids, sugar acids; such as the pectic acids, amino acids, cycloaliphatic acids, aliphatic carboxylic acids, keto carboxylic acids, and the like.

Nicotine salts are formed from the addition of a suitable acid to nicotine.

In certain embodiments, the vaporizable material contains organic material from a *Cannabis* genus plant. In certain embodiments, the vaporizable material contains an extract from a *Cannabis* genus plant. In certain embodiments, the vaporizable material contains a cannabinoid. In certain embodiments, the cannabinoid is tetrahydrocannabinol (THC). In certain embodiments, the cannabinoid is carmabigerolic acid (CBGA). In certain embodiments, the cannabinoid is cannabigerol (CBG). In certain embodiments, the cannabinoid is tetrahydrocannabinolic acid (THCA). In certain embodiments, the cannabinoid is cannabichromene (CBC).

In certain embodiments, the cannabinoid is cannabicyclol (CBL). In certain embodiments, the cannabinoid is cannabivarin (CBV). In certain embodiments, the cannabinoid is cannabichromevarin (CBCV). In certain embodiments, the cannabinoid is cannabigerovarin (CBGV). In certain embodiments, the cannabinoid is cannabigerol Monomethyl Ether (CBGM). In certain embodiments, the cannabinoid is delta 8-tetrahydrocannabinol (D8THC). In certain embodiments, the cannabinoid is delta-9-tetrahydrocannabinol (D9THC).

In certain embodiments, the cannabinoid is tetrahydrocannabivarin (THCV). In certain embodiments, the cannabinoid is cannabinolic acid (CBNA). In certain embodiments, the cannabinoid is Cannabinol (CBN). In certain embodiments, the cannabinoid is cannabidiolic acid (CBDA). In certain embodiments, the cannabinoid is Cannabidivaric acid (CBDVA). In certain embodiments, the cannabinoid is cannabidiol (CBD). In certain embodiments, the cannabinoid is cannabichromenic acid (CBCA). In certain embodiments, the cannabinoid is Cannabichromene (CBC). In certain embodiments, the cannabinoid is cannabicyclolic acid (CBLA). In certain embodiments, the cannabinoid is an Stereo isomer of any of the above mentioned cannabinoids. In certain embodiments, the cannabinoid is a salt of any of the above mentioned cannabinoids.

In certain embodiments, the vaporizable material is a cannabinoid formulation.

In certain embodiments, the vaporizable material is a *Cannabis* formulation.

In certain embodiments, the vaporizable material contains a medicinal compound as an active ingredient. The medicinal compounds that are active ingredients for vaporization with the electronic vaporizer device utilizing the method herein, include drugs that can be heated without combustion to vaporization for inhalation delivery at a temperature range of e.g., about 100° C. (e.g., for water-based carriers, e.g., about 100° C., 105° C., 110° C., 120° C., 130° C., 140° C., 150° C., 160° C., 170° C., etc.; for ethanol-based formulations, e.g., about 50° C., about 60° C., about 70° C., about 80° C., etc.) to about (e.g., below) the temperature at which the active ingredient thermally decomposes (e.g., less than about 150° C., 160° C. 170° C., 180° C., 190° C., 200° C., 210° C., 220° C. 230° C., 240° C. 250° C. 260° C., 270° C., 280° C., 290° C., 300° C., etc.). In certain embodiments, the drugs can be neat or are solubilized in a pharmaceutically acceptable solvent. In certain embodiments, the drugs can include over the counter (OTC) substances as aides for various ailments; wherein said drugs can include known respiratory aides for asthma or chronic obstructive pulmonary disease (COPD). The vaporizable materials that are active ingredients for vaporization with the device(s) described herein, can include drugs that can be heated to vaporization for inhalation delivery, without combustion; wherein said drugs can include over the counter (OTC) substances from the group comprising upper respiratory aides (like cetirizine), analgesics and internal medication aides (like ibuprofen, naproxen), heartburn aides (like omeprazole), sleeping aides (like oxylamine, diphenhydramine, melatonin), or motion sickness aides (like meclizine). In certain embodiments, the vaporizable material can contain respiratory aides for asthma or chronic obstructive pulmonary disease (COPD) such as short acting beta-agonist (like albuterol, levalbuterol, pirbuterol), long acting beta-agonist (like Salmeterol, formoterol), anticholinergics (like atropine Sulfate, ipratropium bromide), leukotriene modifiers (like montelukast, Zafirlukast), corticosteroids (like fluticaSone, budesonide, mometasone), theophylline (like theophylline), or combination corticosteroid and beta agonist, long lasting (fluticasone and Salmeterol, budesonide and formoterol, mometasone and formoterol). In certain embodiments, the vaporizable material can contain botanicals and/or nutraceuticals such as tea (polyphenols, flavonoids, green tea catechins+/−caffeine); horehound (phenol flavonoid glycosides, labdane diterpenoids, yohimbe, cranberry/grape (proanthocyanidins), black cohosh (terpene glycoside fraction (actine/cimifugoside), flaxseed (omegafatty acids), echinacea (echinacoside), Valerian (alkaloids, gabapentin, isovaleric acid, terpenes), *Senna* (senna glycosides), cinnamon (cinnamaldehyde, phenols, terpenes), vitamin D, saw palmetto (fatty acids), or caffeine.

In certain embodiments, the vaporizable material is soluble to at least fifty percent by weight in any suitable carrier solvent such as glycols (such as propylene glycol and vegetable glycerin), ethylene glycol, dipropylene glycol, trimethylene glycol, ethanol, and combinations thereof. In certain embodiments, the medicinal compound is terpinolene. In certain embodiments, the medicinal compound is Linalool. In certain embodiments, the medicinal compound is phytol. In certain embodiments, the medicinal compound is beta myrcene. In certain embodiments, the medicinal compound is citronellol. In certain embodiments, the medicinal compound is aryophyllene oxide. In certain embodiments, the medicinal compound is alpha pinene. In certain embodiments, the medicinal compound is limonene. In certain embodiments, the medicinal compound is beta caryophyllene. In certain embodiments, the medicinal compound is humulene. In certain embodiments, the vaporizable material is an essential oil. In certain embodiments, the medicinal compound is a benzodiazepine.

Cartridge

As described above, in some embodiments, the electronic vaporizer device utilizing the method of computing, delivering and controlling successive and sequential doses or amounts of vapor to the user described herein, such as device 60, includes a separate detachable pod configured to hold a vaporizable material. In certain embodiments, the pod is any receptacle or tank configured to hold a vaporizable material. In certain embodiments, the pod is removable. In certain embodiments, the pod is replaceable. In certain embodiments, the pod and the electronic vaporizer device form a single unit after the pod is attached to the electronic vaporizer device. In certain embodiments, the pod further comprises a mouthpiece. In certain embodiments, the electronic vaporizer device utilizing the methods disclosed herein does not comprise a separate pod configured to hold a vaporizable material, and vaporizable material is stored in the electronic vaporizer device. In certain embodiments, the separate pod contains a vaporization chamber. In certain embodiments, the pod holds between 0.1 and 10 ml of a liquid, viscous liquid or wax. In certain embodiments, the pod holds between 1 and 10 ml of a liquid, viscous liquid or wax. In certain embodiments, the pod holds between 0.1 and 2 ml of a liquid, viscous liquid or wax. In certain embodiments, the pod holds between 0.5 and 1.5 ml of a liquid, viscous liquid or wax.

In some embodiments, the cartridge can be filled with non-hydroscopic solvents and/or be substantially air tight so as to avoid absorption of water in the cartridge. In certain embodiments, the pod contains loose leaf material. In certain embodiments, the pod contains solid material. In certain embodiments, the pod contains tobacco. In certain embodiments, the pod contains a tobacco stick. In certain embodiments, the pod contains a cigarette or the like.

Temperature Sensor

As described above, any of the vaporizer apparatuses described herein, such as devices 60, 100, 210 in FIGS.

1A-1C, can include one or more temperature sensors, such as temperature sensor 250. In certain embodiments, the temperature sensor is configured to measure the temperature of the heating element. The temperature sensor may include software and hardware for measuring the resistance that may be integral with (or separate from) any of the controller and/or processors described herein. In certain embodiments, the temperature sensor is configured to measure the temperature of a vaporization chamber housing the heating element. In certain embodiments, the temperature sensor is configured to measure the temperature of an oven chamber heated by the heating element. In certain embodiments, the temperature sensor measures heat in degrees Celsius. In certain embodiments, the temperature sensor measures heat in degrees Fahrenheit. In certain embodiments, the temperature sensor measures heat in degrees Kelvin. In certain embodiments, the temperature sensor is a thermocouple. In certain embodiments, the temperature sensor is a thermistor. In certain embodiments, the temperature sensor is an infrared temperature sensor. In certain embodiments, the temperature sensor is a relative resistance gradient measurement system. In certain embodiments, the temperature sensor is the heater coil used to heat the vaporizable material.

In certain embodiments, the temperature sensor measures a temperature to an accuracy of ±0.1 degrees Celsius. In certain embodiments, the temperature sensor measures a temperature to an accuracy of ±0.2 degrees Celsius. In certain embodiments, the temperature sensor measures a temperature to an accuracy of ±0.3 degrees Celsius. In certain embodiments, the temperature sensor measures a temperature to an accuracy of ±0.4 degrees Celsius. In certain embodiments, the temperature sensor measures a temperature to an accuracy of ±0.5 degrees Celsius.

It should be noted that the accuracy of the measured temperature may be as poor as ±25° C. (e.g., less than 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., etc.).

In certain embodiments, the temperature sensor measures temperature indirectly by measuring the resistance of the heating element. In certain embodiments, resistance is measured in Ohms. In certain, embodiments, the temperature sensor is capable of measuring a temperature profile, which is a change in temperature over time.

Electronic Delivery Devices, Apparatuses and Methods

Figure 4:
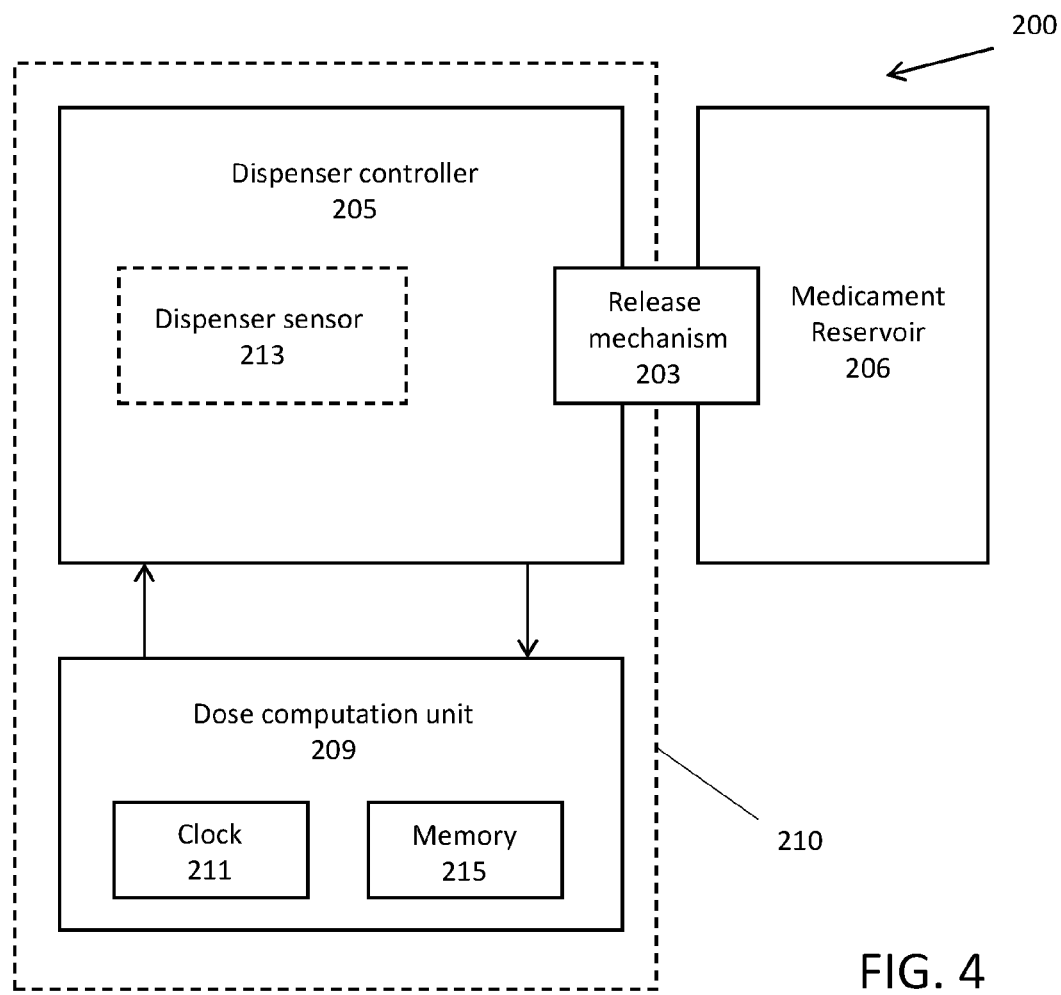
FIG. 4 is a schematic of an electronic (medicament) delivery device including a dose computation unit, a dispenser controller, a release mechanism, and optionally a dispensing sensor.

FIG. 4 is a schematic illustration of one example of an electronic delivery device (for example, an electronic medicament delivery device) 200, including a dose computation unit 209. In general, any of the electronic delivery apparatuses described herein may include a dispenser controller 205, a release mechanism 203, a source of material to be delivered (reservoir or tank) 206, a power source (e.g., battery, not shown), a dose computation unit 209. The dose computation unit 209 may include a clock 211 and/or a memory (memory unit) 215, or these elements may be part of an overall circuitry including a processor 210 which communicates with the dose computation unit.

The release mechanism may be any appropriate release mechanism, such as an electronic controlled valve or the like. The release mechanism (e.g., an electronic controlled valve) is typically coupled to the dispenser controller so that the dispenser controller applies power (e.g., from the power source) to the release mechanism. The dispenser controller may include regulatory control logic or system to regulate the voltage and/or the current and/or the power of the release mechanism by adjusting the applied power. The dispenser controller may include a dedicated or general-purpose processor, circuitry, or the like and is generally connected to the power source and may receive input from the power source to regulate the applied power to the release mechanism, and it may receive input from the dose computation unit to obtain instructions about the power values to be applied to the release mechanism. The controller forming or including the dispenser controller may also include additional controllers/processors and executing logic 210, such as the dose computation unit, or these components may be separate.

Any a source of deliverable material may be used, including a reservoir (e.g., well, pod, cartridge, or the like), which includes the material or the medicinal or substance to be delivered or administered. The material to be delivered may include one or more active ingredients. In certain embodiments, more than one reservoir may be present (not shown).

In certain embodiments, the electronic delivery device may include (optionally) a dispenser sensor 213, configured to measure a physical quantity related to the quantity of substance released during the delivering of a dose (e.g., the position of a release valve stem) and to transmit such a value to the dispenser controller, in order to precisely control the quantity of medicament to be delivered. The dispenser sensor may be any suitable sensor configured to measure the actual quantity of material which is being delivering, such as a flow meter, or a valve stem position sensor or the like. As will be apparent when described in greater detail below, the dispenser sensor is not necessary. For example, the dispenser sensor may not be necessary if a calibrated dispenser mechanism is adopted as release mechanism 203 in the electronic delivery device (for example if a calibrated valve in which a relationship or a look up table between the opening time and the volume of material released by the valve is employed, then the dispenser sensor is not necessary).

In general, the dispenser controller may be configured to control the size of the valve opening or of the release mechanism in order to precisely control the quantity of medicament or substance released during each moment in time.

In general, the dose computation unit is configured to compute the doses to be delivered in successive and sequential administration trials, at groups or at sequences of a given number of doses (or trials/doses). Each of the sequences of doses that have to be computed by the dose computation unit are also termed "stage" herein. For example, a stage can comprise 12 doses to be computed and delivered, or a stage can comprise 10 doses, etc.

In certain embodiments a stage can include only one dose.

The dose computation unit generally bases the calculation on few settable or predetermined parameters: the average cumulative dose to be delivered (expressed as $\bar{\mu}$ in the following) which can vary between stages, the minimum and the maximum values that a dose can assume, and/or the minimum and the maximum value that a dose difference can take, for computing a sequence of successive doses to be delivered in the next trials and their order within the sequence, as will be described in greater detail below.

Figure 5:
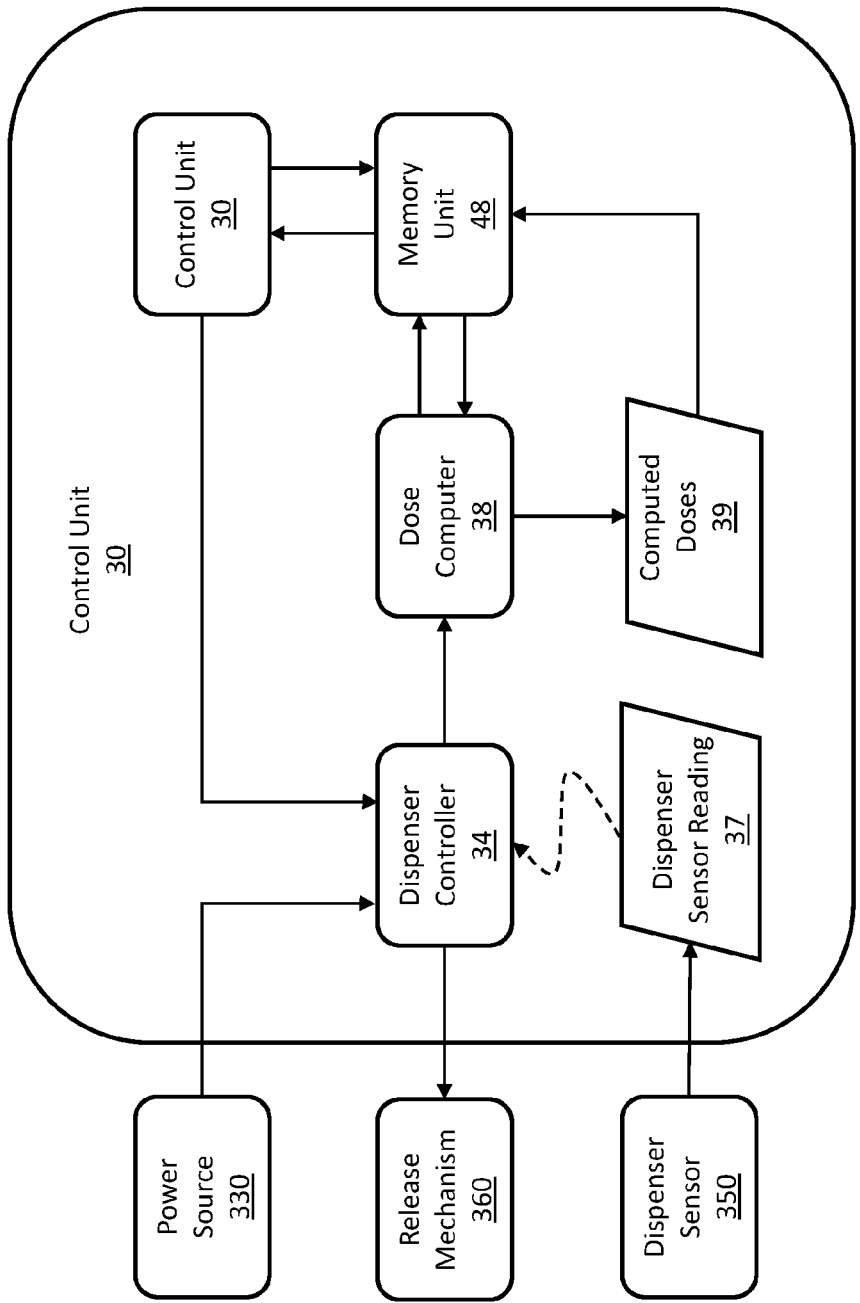
FIG. 5 is an example of an exemplary apparatus able to increase the physiological effects produced by active ingredients (or material, or drug, or substance) delivered by the device.

FIG. 5 shows a flowchart that represents an exemplary electronic medicament delivery apparatus capable of dynamically computing and delivering a sequence of successive doses within the apparatus, comprising: a) computing a sequence of doses to be sequentially delivered in the next trials; b) delivering the computed amount of material within the apparatus. As shown, the power source 330, release mechanism 360, (optional) dispenser sensor 350 are communicatively coupled to a control unit 30 (which can be part of one or more printed circuit board(s) within the apparatus).

The control unit 30 can include a dispenser controller 34, a dose computer (or dose computation unit, which may be a type of dose computation unit) 38 and a related memory unit 48.

To compute a dose or a sequence of successive doses (e.g., a stage of doses involving a given number or batch of doses in sequence) to deliver to a user, the dose computation unit 38 can base the computations on the input from the dispenser controller 34, for example to know when a dose has been delivered, and on the input from the memory unit 48, so that the dose computation unit 38 can calculate a (or some) dose(s) to be delivered, named herein "computed doses to be delivered" 39. In certain embodiments the dose computation unit relays the computed dose(s) 39 and/or some results obtained through computational processing of them, to the memory unit 48. In certain embodiments, the dose computation unit 38 relays the computed doses to be delivered 39 to the memory unit 48, and to the dispenser controller 34, which may control the release mechanisms 360 to deliver the computed dose to be delivered for the actual administration/trial.

To deliver a dose of medicament or material to a user, the control unit 30 can relay (optionally) the dispenser sensor reading 37 to the dispenser controller, which also on the basis of the input from the computed doses to be delivered 39, and/or input from the memory unit 48 can control the power signal (or voltage or current signal) to be applied to the release mechanism (e.g., an electronic controller valve) in order to precisely control the quantity of medicament or substance released during a trial.

Computation of the Doses to be Sequentially Delivered in Successive Trials

In a certain embodiment, the amount of medicament (or material or dose) to be delivered in a given number of successive administration trials, within an electronic delivery device, such as device 200, can be computed from the previous delivered dose(s) (e.g., from the last delivered dose), and from certain values and constraints set up by the producer in the factory, or by the user, or by an algorithm (in particular, the needed values and/or constraints which will be described in a greater detail hereinafter, may be set up automatically or manually, and may be set up at the factory, in some variations, the values may be set up by the user). More specifically, the doses to be delivered can be computed in batch of a given number of doses/trials, taking into account the dose(s) delivered immediately before, and specific constraints: the doses may be computed such that the average positive dose difference is greater in magnitude than the average negative dose difference, subject to the constraint that the average cumulative administered dose (i.e., the sum of the doses delivered over successive trials divided by the number of trials) is kept constant or equal to a predetermined value over time (or over successive trials) or it is reduced (or it is varied and set as desired), and subject to the constraint that each dose can take only values within a settable or predetermined range, and/or subject to the constraint that a dose difference can assume values within predetermined ranges, wherein a dose difference is defined as the difference between the dose of substance (including active ingredients and drugs) delivered in a given trial and the dose delivered in the trial immediately before, or as the difference between the dose delivered in a given trial and a liner combination of the doses delivered sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

In certain embodiments, the average dose difference has to be greater in magnitude (i.e., the absolute values have to be compared) than the average negative dose difference of about a 5% factor. In certain embodiments, the magnitude of the average dose difference has to be greater than the magnitude of the average negative dose difference of about a 10% factor. In certain embodiments, the magnitude of the average dose difference has to be greater than the magnitude of the average negative dose difference of about a 15% factor. In certain embodiments, the magnitude of the average dose difference has to be greater than the magnitude of the average negative dose difference of about a 20% factor. In certain embodiments, the magnitude of the average dose difference has to be greater than the magnitude of the average negative dose difference of about a 25% factor. In certain embodiments, the magnitude of the average dose difference has to be greater than the magnitude of the average negative dose difference of about a 30% factor. In certain embodiments, the magnitude of the average dose difference has to be greater than the magnitude of the average negative dose difference of about a 35% factor. In certain embodiments, the magnitude of the average dose difference has to be greater than the magnitude of the average negative dose difference of about a 40% factor. In certain embodiments, the magnitude of the average dose difference has to be greater than the magnitude of the average negative dose difference of a factor greater than a 40% (e.g., of a 50% factor, of a 200% factor, and so on).

The doses (or any quantity related to the dose, such as a temperature, a power, a time, etc.) can be computed and delivered sequentially in a random or pseudo-random or in a deterministic order.

The doses may be computed in the dose computation unit, or they can be pre-computed externally and upload into a memory unit of the dose computation unit or a memory unit of the electronic delivery device.

In a certain embodiment, an example of the methods of computing a batch (or a stage) of doses, may include performing the following steps (in such an embodiment, a dose difference is assumed to be the difference between the dose delivered (or to be delivered) in a given trial and a dose delivered in the trial immediately before):

1) In a generic stage with a settable or predetermined number of trials, named $\tilde{n}$, for which the doses have to be computed (and delivered), and given two settable or predetermined values for the number of positive doses differences and for the number of negative doses differences (e.g., set in the factory), named $n_+$ and $n_-$, respectively, and such that $\tilde{n}=n_++n_-$ (for a non-limiting example, $\tilde{n}=12$, $n_+=3$, $n_-=9$), determine the sequential positions of all the $\tilde{n}$ differences doses, for example in a random way (for example, in a certain embodiment wherein a stage involving 12 doses to be computed is considered, a randomly generated sequence of 9 negative and 3 positive doses differences, may appear as in the follows: $diff^-$, $diff^-$, $diff^-$, $diff^-$, $diff^+$, $diff^-$, $diff^-$, $diff^+$, $diff^-$, $diff^-$, $diff^-$, $diff^+$, where each term $diff^-$ represents a position of a negative dose difference and each term $diff^+$ represents a position of a positive dose difference). Without desired to be bound by any theory, it is preferable setting the very first dose of a given stage to be relatively "high", for neurophysiological reasons. In such a case, if the last delivered dose of the previous stage was higher than the average delivered dose (e.g., the last dose difference of the previous stage was a positive difference), then the first dose of the actual stage may be set equal to the last dose delivered in the previous stage, moreover, only the remaining $\tilde{n}-1$ doses differences positions have to be initialized. Conversely, if the last delivered dose in the previous stage was lower than the average delivered dose (e.g., the last dose difference of the previous stage was a negative difference), then the first position of the doses differences in the actual stage may be assigned to a positive dose difference, and the others $n_-$ negative and $n_+-1$ positive doses differences positions can be randomly assigned.

2) Initialize the values of the negative doses differences, for example, in a certain embodiment, this may be accomplished by generating $n_-$ values from a gaussian distribution with a given/settable mean, $\mu_-$, and a given/settable variance, $\sigma_-^2$. For instance, $\mu_-$ may be set in milligrams (mg) (for example $\mu_-=-0.1$, and $\sigma_-^2=0.1$), which means that a random generated value sampled from a gaussian distribution whose mean is equal to $-0.1$ mg and whose variance is equal to 0.1 represents a dose decrement in mg (i.e., a negative dose difference expressed in mg). The computed/initialized negative doses may be attributed to an active substance (in mg), such a medicament substance.

3) Compute the positive doses differences such that the average delivered dose in the actual stage will be equal to a settable or predetermined value, named $\bar{\mu}$, (for example, $\bar{\mu}$ can be set to be equal to the average value of the doses delivered in the previous stage, named $\mu_{PREC}$, or in general, it may be set to be equal to a predetermined value, such as the desired average mg of an active ingredient or drug, or it may be set as a time-varying value). In a certain embodiment, for computing the positive doses differences, the following equation can be solved:

$$\alpha_1 \cdot \text{diff}_1^- + \alpha_2 \cdot \text{diff}_2^- + \ldots + \alpha_{n_-} \cdot \text{diff}_{n_-}^- + \beta_1 \cdot \text{diff}_1^+ + \beta_2 \cdot \text{diff}_2^+ + \ldots \beta_{n_+} \cdot \text{diff}_{n_+}^+ = (\bar{\mu} - D_{-1}) \cdot \tilde{n}$$

while imposing the following condition:

$$\text{diff}_1^+ = \text{diff}_2^+ = \ldots = \text{diff}_{n_+}^+ = \text{diff}^+,$$

where, $D_{-1}$ represents the last delivered dose in the previous stage, $\alpha_i$ ($\beta_i$) $i\in[1,n_-]$ ($i\in[1,n_+]$) represents the numerical value corresponding to the position, in a reverse order, of the i-th negative (positive) dose difference $\text{diff}_i^-$ ($\text{diff}_i^+$) within the full sequence of $\tilde{n}$ doses differences. For instance, if $\text{diff}_1^-$ occupies the first position within the full sequence of doses differences, then $\alpha_1 = \tilde{n}$. Hence, each positive dose difference may be obtained computing the equation 1.

4) Compute, sequentially, the $\tilde{n}$ doses to be delivered, starting from the last delivered dose in the previous stage (named $D_{-1}$), and summing recursively the doses differences of the initialized sequence, in the actual stage. More precisely, the first dose ($D_1$) can be computed as the sum between $D_{-1}$ and the dose difference in the first position of the sequence; then, the second dose ($D_2$) can be computed as the sum between $D_1$ and the dose difference in the second position, and so on.

In practice, compute $D_i = D_{i-1} + \text{diff}_i^-$ where $D_i$ represents the dose to be deliver at the i-th trial and represents the dose to be delivered at the (i−1)-th trial, if the i-th dose difference within the sequence is a negative dose difference, or compute $D_i = D_{i-1} + \text{diff}_i^+$ if the i-th dose difference within the sequence is a positive dose difference.

5) If the computed doses are within a settable or predetermined range (e.g., each dose is within a range delimited by a minimum and a maximum predetermined value, $\min \leq D_i \leq \max$), then go to the next point. Conversely, if one of the computed doses in the actual stage is out of range, then perform a new initialization, restarting from point 1).

For a non-limiting example, in a certain embodiment, the minimum value that a delivered dose of a given drug can take may be equal to 0.6 mg and the maximum value may be equal to 1.5 mg.

6) Deliver the computed doses, sequentially, for the actual computation stage whenever a dose administration is requested (e.g., automatically with a given timing, requested from the user by pushing a button, etc.). Furthermore, after that all the computed doses in the actual stage have been delivered, go to point 1), for the beginning of a new computation stage.

Figure 10:
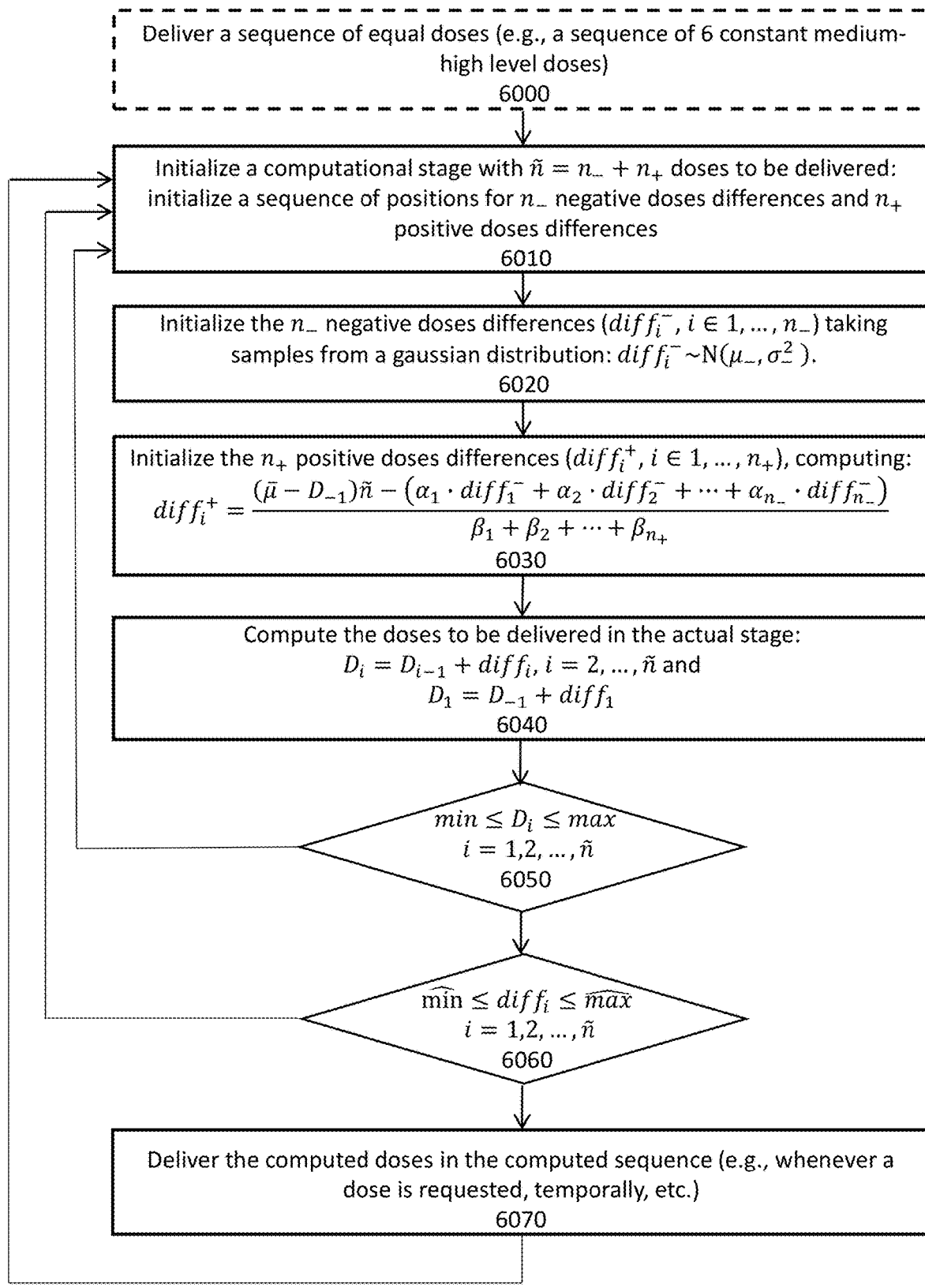
FIG. 10 schematically illustrates one method of computing a sequence of successive doses to be delivered in an electronic controlled delivery device, as described herein.

FIG. 10 illustrates this exemplary method of computing a batch (i.e., a given number) of doses to be delivered during each successive administration trial within a given stage, wherein a stage comprises a batch (or a sequence) of trials. For example, in FIG. 10 (optionally) a first sequence of a predetermined number (for example 6) constant doses of a given substance (or active ingredients such as, for example lidocaine, or morphine, etc.), may be delivered to establish pharmacotherapeutic conditioning 6000. After that, a first initialization may occur, in which a computational stage comprising $\tilde{n} = n_- + n_+$ doses (where $\tilde{n}$ represents the total dose to be delivered, or the total number of doses differences to be computed/initialized; $n_-$ represents the number of negative doses differences to be computed within the actual stage, and $n_+$ represents the number of positive doses differences to be computed within the actual stage) is initialized, such that a sequence of positions for $n_-$ negative doses differences and $n_+$ positive doses differences is determined (e.g., randomly) 6010. For instance a sequence of randomly positive and negative doses differences may result as follows: $\text{diff}^-$, $\text{diff}^-$, $\text{diff}^-$, $\text{diff}^-$, $\text{diff}^+$, $\text{diff}^-$, $\text{diff}^-$, $\text{diff}^+$, $\text{diff}^-$, $\text{diff}^-$, $\text{diff}^-$, $\text{diff}^+$, in such a non-limiting example we have $\tilde{n} = n_- + n_+ = 12$, $n_- = 9$ and $n_+ = 3$. In general, given a fixed $\tilde{n}$ of doses differences to be computed, it may be necessary to have $n_- > n_+$ so that the magnitude of the resulting positive doses differences will be greater than the negative doses differences, as it will be described in a greater detail hereinafter.

Afterwards, the values of the negative doses differences may be initialized. This may be accomplished by generating $n_-$ values from a gaussian distribution with a settable or predetermined mean, $\mu_-$, and a settable or predetermined variance, $\sigma_-^2$. For instance, $\mu_-$ may be set in milligrams (mg) (for example $\mu_- = -0.2$, and $\sigma_-^2 = 0.1$), which means that a random generated value sampled from a gaussian distribution whose mean is equal to $-0.2$ mg and whose variance is equal to 0.1 represents a dose decrement in mg (i.e., a negative dose difference expressed in mg). The computed/initialized negative doses may be attributed to an active substance (in mg), such as nicotine, anesthetic or other drugs, etc. 6020.

At this point, the apparatus may compute the positive doses differences, such that the average dose to be delivered in the actual stage is equal to a settable or predetermined value, named $\bar{\mu}$, (for example, $\bar{\mu}$ can be set to be equal for all the stages and it may be set to be equal to a predetermined value, such as the desired average dose, in mg, of drug, or it may be set as a time-varying value for successive stages, such as a decreasing function of mg of active ingredient as the number of stages increases). The positive doses differences may be set all equals between each other in a given stage (or batch of doses), and their magnitude ($\text{diff}_i^+$) may be computed adopting equation 1, already shown herein and rewritten in the following for clarity (6030):

$$diff_i^+ = \frac{(\bar{\mu} - D_{-1}) \cdot \tilde{n} - (\alpha_1 \cdot diff_1^- + \alpha_2 \cdot diff_2^- + \ldots + \alpha_{n_-} \cdot diff_{n_-}^-)}{\beta_1 + \beta_2 + \ldots + \beta_{n_+}} \quad \text{(equation 1)}$$

where, $D_{-1}$ represents the delivered dose in the last administration trial of the previous stage, $\alpha_1$ ($\beta_i$) i∈[1,n_] (i∈[1,n_+]) represents the numerical value corresponding to the position, in a reverse order, of the i-th negative (positive) dose difference $diff_i^-$ ($diff_i^+$) within the full sequence of doses differences. For instance, if $diff_1^-$ occupies the first position within the full sequence of doses differences, then $\alpha_1 = \tilde{n}$; if $diff_1^-$ occupies the last but one position then $\alpha_1 = \acute{n}-1$, and so on.

The electronic delivery device may further compute the sequence of doses to be delivered (within the actual stage) sequentially during each successive administration trial. Such a computation may start from the last delivered dose in the previous stage (indicated with $D_{-1}$), and summing recursively the doses differences of the initialized sequence, in the actual stage. More precisely, the first dose ($D_1$) may be computed as the sum between $D_{-1}$ and the dose difference in the first position of the computed sequence; then, the second dose ($D_2$) may be computed as the sum between $D_1$ and the dose difference in the second position, and so on. In formulae, the computation of the sequence of the doses to be delivered may be expressed as follows: $D_i = D_{i-1} + diff_i$, where $D_i$ represents the dose in the i-th position within the sequence of doses, and $diff_i$ represents the dose difference (either positive or negative) corresponding to the i-th position within the computed sequence 6040.

At the end of the doses computations, the apparatus may check to see if each of the computed doses is comprised between a predetermined (settable) minimum (min) and maximum (max) value. For a non-limiting example, the min value may be set equal to 1 mg of a given active ingredient, and the max value equal to 2.5 mg of the considered active ingredient 6050. If not, then the system may move onto step 6010 and restart the doses computation anew (i.e., performing a new stage initialization etc.). Optionally, the apparatus may check to see if each of the computed doses differences is comprises between a predetermined (settable) minimum and a predetermined (settable) maximum value 6060, if this is not the case the system may move onto step 6010. If each of the computed doses fall within said range (and optionally even the doses differences), then the system may deliver sequentially the successive doses, whenever requested (e.g., by button pressure, or temporally, etc.) within the computed sequence of doses (e.g., the dose computation unit may transmit the actual computed dose to the dispenser controller which, in turn, may control the release mechanism to deliver the computed dose) 6070. Then, the apparatus may perform a new computational stage and a new initialization for all the doses differences, restarting from the state 6010.

It is worth noting, that other methods for computing a sequence of doses (or amounts of ingredient(s)) that satisfy the constraints and the features described above (e.g., the feature that the average positive dose difference is greater in magnitude than the average negative dose difference, the constraint that the average cumulative delivered dose is kept constant over time or it is reduced or it is imposed/set as desired, the constraint that a dose can only assume values within a predetermined range delimited by a predetermined maximum value and a predetermined minimum value, and, optionally the constraint that each dose difference can only take values within predetermined ranges), can be adopted with the present invention.

Addiction Reduction and Treatment, Methods and Apparatuses

In some embodiments, disclosed herein are methods and apparatuses that allow or facilitate a user in drug use cessation or in reducing a given substance addiction. In particular, in some embodiments, a method for drug use reduction or drug addiction reduction and treatment may include: calculating and delivering successive and varying doses of drug (or material or active ingredients) sequentially over successive drug administration trials, such that, the average positive dose difference is greater in magnitude than the average negative dose difference, subject to the constraint that the average cumulative administered dose (i.e., the sum of the doses delivered over successive trials divided by the number of trials) of active drug or of active physiological principle or of active ingredients is gradually reduced (e.g., by reducing the concentration of the active ingredients), and subject to the constraint that a dose can only assume values within a given range delimited by a settable or predetermined maximum value and a settable or predetermined minimum value, and, optionally, subject to the constraint that a dose difference can assume values within predetermined or settable ranges; wherein a dose difference is defined as the difference between the dose (including active ingredients) delivered in a given trial and the dose delivered in the trial immediately before, or as the difference between the dose delivered in a given trial and a liner combination of the doses sequentially delivered in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

Without desiring to be bound by theory, it is argued that increasing the reactive contributions (i.e., the neurophysiological effects due to classical conditioning or reinforcement and/or unconditioned stimulus revaluation) while reducing the active contributions (i.e., by reducing the active drug or ingredient to reduce the effects provoked by the active ingredients) may determine a reduction in the physical addiction. Moreover, in certain embodiments, after the accomplishment of the abovementioned procedure, a decreasing of the reactive contributions may be employed, in order to extinguish the reactive responses/effects (which, in general, may be resistant-to-extinction, so that it could not be sufficient to extinguish them by simply performing a progressive reduction of the active delivered doses without accomplishing a proper schedule for the reactive contributions reduction), and such a method may include: calculating and delivering varying doses of substance (e.g., active ingredients) over sequential trials, such that, starting from a given (predetermined) trial, the average positive dose difference is smaller in magnitude than the average negative dose difference, subject to the constraint that the average cumulative delivered dose (i.e., the sum of the doses delivered over successive trials divided by the number of trials) of active drug or of active physiological principle or of active ingredients is kept constant or gradually reduced (or set up as desired), subject to the constraint that a dose can only assume values within a predetermined range delimited by a settable or predetermined maximum value and a settable or predetermined minimum value, and subject to the constraint that a dose difference can assume values within predetermined ranges; wherein a dose difference is defined as the difference between the dose delivered in a given trial and the dose delivered in the trial immediately before, or as the difference between the dose delivered in a given trial and a liner combination of the doses sequentially delivered in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

Figure 9:
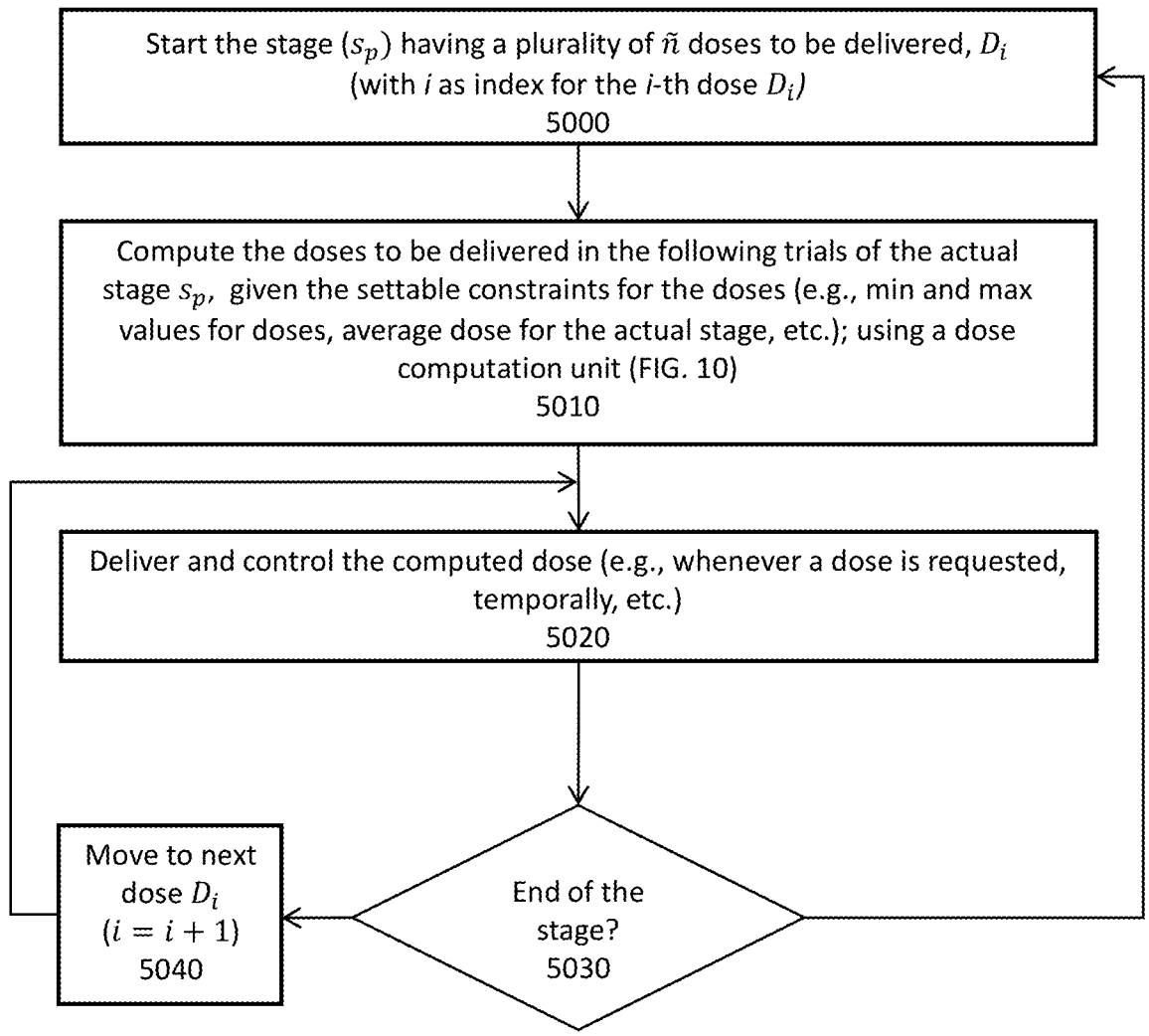
FIG. 9 schematically illustrates one method of computing and delivering a sequence of doses of a substance (e.g., an active drug), in order to increase the neuropsychophysiological or physiological effects of the delivered substance(s) in an electronic controlled delivery device, as described herein.

FIG. 9 illustrates a method of computing and delivering successive doses of drug or active ingredients to a user, in order to increase the neuropsychophysiological or physiological effects of the delivered substance(s), as described herein. For example, in FIG. 9 the trial number (or equivalently the dose number) within a given stage (comprising a settable number of trials/doses indicated as ñ) for determining/computing and delivering the dose $D_i$ (relative to the i-th trial within the considered stage $s_p$) may be initially set or started 5000. The start of the stage may be triggered by the user, physician or other party (e.g., manually) or it may automatically start, e.g., when a user presses a button on the electronic delivery device (e.g., activating the dispenser controller which, in turn, controls the release mechanism).

The number of the trials/doses within a given stage can be predetermined (e.g. 10, 12, or 100, etc.), or it may be variable.

The apparatus may compute the doses to be delivered within the actual stage, for example adopting the methods disclosed herein, using a dose computation unit 5010. In certain embodiments, one method to compute the doses to be delivered in the trials of a given stage is described herein in detail and it is depicted in FIG. 10.

After the computation of the doses to be delivered sequentially over successive and sequential administration trials, the apparatus may deliver one dose at a time 5020. The dose delivery, or the dose administration, may be triggered by the physician, or by the user (e.g., by pressing a button), or automatically (e.g., with a preset timing of dose delivery or of dose administration). In certain embodiments, the apparatus may control the release mechanism (for example an electronic controlled release valve) to deliver the computed dose. In certain embodiments, the apparatus may control the release mechanism through the dispenser controller 205. In certain embodiments, the dispenser controller may control the release mechanism on the basis of the feedback provided by the dispenser sensor 213.

At the end of each delivered dose, the apparatus may check to see if the end of the stage has been reached, either because of a predetermined number of trials/doses ñ has been reached (i=ñ) or because of some other triggering event (e.g., the end of treatment session, etc.), or both 5030. If not, then the system may move onto the next dose to be delivered within the sequence of doses computed of the actual stage (i.e., $D_i$), incrementing the index of the dose position within the sequence (i.e., i=i+1) 5040. Once the end has been reached, the apparatus may start a new computational stage (comprising the initialization and the computation of ñ doses to be delivered).

CONCLUSION, RAMIFICATIONS, AND SCOPE

The methods and devices herein are useful for the therapeutic delivery of nicotine for smoking cessation, harm reduction and/or substitution. Furthermore, the devices and methods herein are useful as an alternative, general nicotine delivery system in place of tobacco combustion or high temperature (over 150 degrees C.) products. In addition, the methods and devices herein are useful for the therapeutic delivery of a drug, for reducing the cumulative drug dose while increasing the physiological effects. Moreover, the devices and methods herein are useful for addiction treatment or reduction.

In some embodiments, the reactive contributions associated with the administration of a dose of a given substance (including drugs or active ingredients) may be enhanced adopting the methods and the apparatuses disclosed herein.

In certain embodiments, the reactive contributions, and hence, the neurophysiological and/or the physiological effects associated to a given drug may be enhanced through dynamically varying the administered doses over successive administration trials (or puffs/trials), as disclosed herein. In certain embodiments, other quantities related to the delivered dose, such as a temperature, a frequency, a power, a time, etc., may be computed and varied over successive administration trials, such that, starting from a given trial the average positive dose difference is greater in magnitude than the average negative dose difference, subject to the constraint that the average cumulative administered or inhaled dose (i.e., the sum of the doses delivered over successive puffs/trials divided by the number of trials) is kept constant or equal to a predetermined value over time (or over successive puffs/trials) or it is reduced (or it is varied and set as desired), and subject to the constraint that a dose difference can assume values within predetermined ranges, and/or subject to the constraint that each dose can take only values within a settable or predetermined range, wherein a dose difference is defined as the difference between the dose of vapor or material (including active ingredients) delivered or inhaled in a given trial and the dose delivered or inhaled in the trial immediately before, or as the difference between the dose delivered or inhaled in a given trial and a liner combination of the doses delivered or inhaled sequentially in some of the trials immediately before, and wherein a positive (negative) dose difference is defined as a dose difference whose value is greater (smaller) than zero, and wherein the average positive (negative) dose difference is defined as the sum of the values of the positive (negative) doses differences divided by the number of such positive (negative) doses differences.

In certain embodiments, a predetermined (or settable) value of the cumulative dose of vapor or substance to be delivered is considered in place of a predetermined (or settable) value of the average dose to be delivered.

In some variants, the puff duration predictor unit described in great details herein, may be configured to predict the puff volume, and/or other puffing features in place of the puff duration, without departing from the spirit and the scope of the invention.

The foregoing disclosure and description of the invention are illustrative and explanatory thereof and various adaptations may be made without departing from the spirit of the invention.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item includes the possibility that there are a plurality of the same items present. More specifically, as used herein and in the appended claims, the singular forms "a," "and," "said", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly" on another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or under lie the adjacent feature.

It will be further understood that the terms "comprises" and/or "comprising" when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately", even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to the value", "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of computing and delivering a plurality of sequential doses of an active substance to a user of a medicament delivery device over a stage of trials, wherein the stage of trials comprises a plurality of sequential administration trials and wherein the medicament delivery device includes a release mechanism device, a medicament reservoir, a dose computation unit, a dispenser controller, the method comprising:
    a. determining the values of the plurality of sequential doses in the dose computation unit, so that the sum of the differences between each administrated dose and the dose administered in the immediately preceding trial, divided by the number of the plurality of the sequential administration trials of said stage of trials, is greater than zero, and so that the number of differences between the dose administered in a trial and the dose administered in the immediately preceding trial that are less than zero is greater than the number of differences between the dose administered in a trial and the dose administered in the immediately preceding trial that are greater than zero;
    b. transmitting the values of the plurality of sequential doses from the dose computation unit to the dispenser controller;
    c. delivering the plurality of sequential doses of the active substance from the medicament reservoir, wherein the release mechanism delivers the plurality of sequential doses of the active substance over the sequential administration trials,
    whereby the physiological effects associated with the active substance will be increased.

2. The method of claim 1 wherein determining the values of the plurality of sequential doses in the dose computation unit further including the constraint that the sum of the values of the differences between the dose administered in a trial and the dose administered in the immediately preceding trial that are greater than zero is substantially double the sum of the additive inverse of the values of the differences between the dose administered in a trial and the dose administered in the immediately preceding trial that are less than zero.

3. The method of claim 1 wherein the dispenser controller comprises a dispenser sensor.

4. The method of claim 1 wherein the computation unit comprises a memory unit, wherein the memory unit contains predetermined values for the plurality of sequential doses.

5. The method of claim 1 wherein the computation unit comprises a memory unit, wherein the memory unit contains predetermined parameters.

6. The method of claim 1 wherein determining the values of the plurality of sequential doses in the dose computation unit further including the constraint that the sum of the quantities of the sequential doses administered in each stage decreases over a sequence of successive stages, whereby drug addiction disorders will be reduced.

7. A method of delivering a plurality of sequential doses of an active substance to a user over a stage of trials, wherein the stage of trials comprises a plurality of sequential administration trials, the method comprising:
    a. determining the values of the plurality of sequential doses to be delivered, so that the sum of the differences between each administrated dose and the dose administered in the immediately preceding trial, divided by the number of the plurality of the sequential administration trials of said stage of trials, is greater than zero, and so that the number of differences between the dose administered in a trial and the dose administered in the immediately preceding trial that are less than zero is greater than the number of differences between the dose administered in a trial and the dose administered in the immediately preceding trial that are greater than zero; and
    b. delivering the plurality of sequential doses of the active substance over the sequential administration trials,
    whereby the physiological effects associated with the active substance will be increased.

8. The method of claim 7, wherein determining the values of the plurality of sequential doses further including the constraint that the sum of the quantities of the sequential doses administered in each stage decreases over a sequence of successive stages, whereby drug addiction disorders will be reduced.

9. The method of claim 7 wherein determining the values of the plurality of sequential doses to be delivered further including the constraint that the sum of the values of the differences between the dose administered in a trial and the dose administered in the immediately preceding trial that are greater than zero is substantially double the sum of the additive inverse of the values of the differences between the dose administered in a trial and the dose administered in the immediately preceding trial that are less than zero.

10. A method of delivering a plurality of sequential doses of a vaporizable material to a user of a vaporizing device over a stage of puffs, wherein the stage of puffs comprises a plurality of sequential administration puffs, and wherein the vaporizing device includes a heater controller, a heater, a source of the vaporizable material, a dose computation unit, a dose delivery unit, a puff duration predictor unit, the method comprising:
  a. calculating the values of the plurality of sequential doses in the dose computation unit, so that the sum of the differences between each administrated dose and the dose administered in the immediately preceding puff, divided by the number of the plurality of the sequential administration puffs of said stage of puffs, is greater than zero, and so that the number of differences between the dose administered in a puff and the dose administered in the immediately preceding puff that are less than zero is greater than the number of differences between the dose administered in a puff and the dose administered in the immediately preceding puff that are greater than zero;
  b. transmitting the value of the plurality of sequential doses from the dose computation unit to the dose delivery unit;
  c. predicting the puff topography features of a incoming puff in the puff duration predictor unit;
  d. transmitting the puff topography features from the puff duration predictor unit to the dose delivery unit;
  e. calculating, for the time duration of the incoming puff a power profile in the dose delivery unit;
  f. delivering the power profile from the heater controller to the heater for vaporizing the vaporizable material in the source of the vaporizable material over the time duration of the incoming puff;
  g. computing a total delivered dose of vapor in the dose delivery unit;
  h. transmitting the value of the total delivered dose of vapor from the dose delivery unit to the dose computation unit,
  i. whereby the physiological effects associated with the vaporizable material will be increased.

11. The method of claim 10, wherein the time duration of each of the plurality of sequential puffs comprises a plurality of sequential time intervals and further including calculating, for each of the plurality of sequential time intervals, a power in the dose delivery unit.

12. The method of claim 10, wherein the vaporizable material is a liquid.

13. The method of claim 10, wherein the puff duration predictor unit comprises a puff sensor.

14. The method of claim 10, wherein calculating the values of the plurality of sequential doses in the dose computation unit further including the constraint that the sum of the quantities of the sequential doses administered in each stage of puffs decreases over a sequence of successive stages, whereby drug addiction disorders will be reduced.

15. The method of claim 10, wherein calculating the values of the plurality of sequential doses in the dose computation further including the constraint that the sum of the values of the differences between the dose administered in a puff and the dose administered in the immediately preceding puff that are greater than zero is substantially double the sum of the additive inverse of the values of the differences between the dose administered in a puff and the dose administered in the immediately preceding puff that are less than zero.

16. The method of claim 10, wherein the vaporizable material comprises a tobacco-based material.

17. The method of claim 10, wherein the vaporizable material comprises a nicotine compound.

18. The method of claim 10, wherein the vaporizable material is selected from the group consisting of the cetirizine, ibuprofen, naproxen, omeprazole, doxylamine, diphenhydramine, melatonin, meclizine and combinations thereof.

19. The method of claim 10, wherein the vaporizable material comprises a cannabinoid.

20. The method of claim 10, wherein the vaporizable material is selected from the group consisting of the albuterol, levalbuterol, pirbuterol, salmeterol, formoterol, atropine sulfate, ipratropium bromide, fluticasone, budesonide, mometasone, montelukast, zafirlukast, theophylline, fluticasone and salmeterol, budesonide and formoterol, mometasone and formoterol, and combinations thereof.

* * * * *